US012715868B2

(12) United States Patent
Banerjee et al.

(10) Patent No.: US 12,715,868 B2
(45) Date of Patent: Aug. 25, 2026

(54) SMARCA2-VHL DEGRADERS

(71) Applicant: AMGEN INC., Thousand Oaks, CA (US)

(72) Inventors: Abhisek Banerjee, Bangalore (IN); Victor J. Cee, Thousand Oaks, CA (US); Ning Chen, Thousand Oaks, CA (US); Xiaofen Li, Thousand Oaks, CA (US); Ryan Paul Wurz, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 887 days.

(21) Appl. No.: 17/788,272

(22) PCT Filed: Jan. 8, 2021

(86) PCT No.: PCT/US2021/012683

§ 371 (c)(1),
(2) Date: Jun. 22, 2022

(87) PCT Pub. No.: WO2021/142247

PCT Pub. Date: Jul. 15, 2021

(65) Prior Publication Data

US 2023/0091042 A1 Mar. 23, 2023

Related U.S. Application Data

(60) Provisional application No. 62/959,502, filed on Jan. 10, 2020.

(51) Int. Cl.
*C07D 417/14* (2006.01)

(52) U.S. Cl.
CPC .................................. *C07D 417/14* (2013.01)

(58) Field of Classification Search
CPC ............................... C07D 417/14; A61P 35/00
See application file for complete search history.

(56) References Cited

U.S. PATENT DOCUMENTS

2019/0300521 A1* 10/2019 Crew ..................... A61K 47/55

FOREIGN PATENT DOCUMENTS

WO 2019/123367 A1 6/2019
WO WO-2019207538 A1 * 10/2019 ......... C07K 5/06052
WO 2019/213005 A1 11/2019

OTHER PUBLICATIONS

Farnaby W, Koegl M, Roy MJ, Whitworth C, Diers E, Trainor N, et al. BAF complex vulnerabilities in cancer demonstrated via structure-based PROTAC design. Nat Chem Biol. 2019; 15:672-80 (Year: 2019).*

Zugazagoitia et al., Clin. Ther. 2016;38(7):1551-66 at p. 1564. (Year: 2016).*

Guerrero-Martínez JA, Reyes JC. Sci Rep. Feb. 1, 2018;8(1):2043. doi: 10.1038/s41598-018-20217-3. (Year: 2018).*

Hoffman et al., "Functional epigenetics approach identifies BRM/SMARCA2 as a critical synthetic lethal target in BRG1-deficient cancers", Proceedings of the National Academy of Sciences, vol. 111(8), pp. 3128-3133(2014).

Hohmann et al., "A rationale to target the SWI/SNF complex for cancer therapy", Trends in Genetics, vol. 30(8), pp. 1-8(2014).

Intention to grant received for European Patent Application No. 21702829.9, mailed on Jan. 23, 2026, 6 pages.

International Preliminary Report on Patentability received for PCT Patent Application No. PCT/US2021/012683, mailed on Jul. 21, 2022, 09 pages.

International Search Report and Written Opinion received for PCT Patent Application No. PCT/US2021/012683, mailed on May 3, 2021, 12 pages.

Jeanmougin et al., "The bromodomain revisited", Trends in biochemical sciences, vol. 22(5), pp. 151-153(1997).

Muller et al., "Bromodomains as therapeutic targets", Expert reviews in Molecular medicine, vol. 13;e29, pp. 1-21 (2011).

Oike et al., "A synthetic lethality-based strategy to treat cancers harboring a genetic deficiency in the chromatin remodeling factor BRG1", Cancer Research, vol. 73(17), pp. 5508-5518(2013).

Prinjha et al., "Place your BETs: the therapeutic potential of bromodomains", Trends in pharmacological sciences, vol. 33(3), pp. 146-153(2012).

(Continued)

*Primary Examiner* — Clinton A Brooks
*Assistant Examiner* — Izabela Schmidt
(74) *Attorney, Agent, or Firm* — Elsa D. Lemoine

(57) ABSTRACT

The present invention provides a compound of formula (I) or a pharmaceutically acceptable salt thereof, pharmaceutical compositions comprising a compound of the invention, a method for manufacturing compounds of the invention and therapeutic uses thereof.

(I)

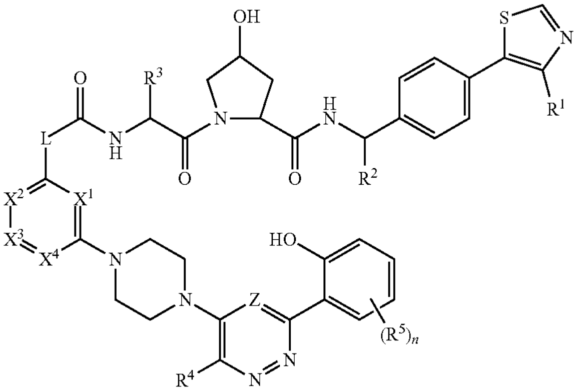

4 Claims, No Drawings

(56) References Cited

OTHER PUBLICATIONS

Struhl K., "Histone acetylation and transcriptional regulatory mechanisms", Genes & development, vol. 12(5), pp. 599-606(1998).

Tamkun et al., "brahma: a regulator of Drosophila homeotic genes structurally related to the yeast transcriptional activator SNF2/SWI2", Cell, vol. 68(3), pp. 561-572(1992).

* cited by examiner

SMARCA2-VHL DEGRADERS

CROSS REFERENCES TO RELATED APPLICATIONS

This application is a National Stage Application under 35 U.S.C. § 371 of International Application No. PCT/US21/12683, having an international filing date of Jan. 8, 2021, which was published on Jul. 15, 2021, as WO 2021/142247, which claims priority from U.S. Provisional Application No. 62/959,502, having a filing date of Jan. 10, 2020.

The present invention relates generally to a class of substituted 3-pyridazinyl-2-phenols and 6-(1,2,4-triazinyl)-2-phenols which bind to the Switch/Sucrose Non-Fermentable (SWI/SNF) complex and to von Hippel-Lindau (VHL) E3 ligase complex, in particular, to substituted 3-pyridazinyl-2-phenols and 6-(1,2,4-triazinyl)-2-phenol compounds which bind to SWI/SNF Related, Matrix Associated, Actin Dependent Regulator of Chromatin, Subfamily A, Members 2 and 4 (SMARCA2 and/or SMARCA4) and to VHL, uses thereof, processes for the preparation thereof and compositions comprising said compounds. In certain aspects, the compounds described herein bind to SMARCA2 and VHL contemporaneously to facilitate ubiquination of SMARCA2 and subsequent targeted degradation of SMARCA2. These compounds have utility in a variety of therapeutic areas including in the treatment of solid tumor cancer.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin state is controlled by a series of post-translational modifications to histone proteins, notably histones H3 and H4, and most commonly within the "histone tails" which extend beyond the core nucleosome structure. Histone tails are sites of protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translation modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.,* 1989, 12, 5, 599-606).

Bromodomains, which are approximately 110 amino acids long, are formed in a large number of chromatin-associated proteins and have been identified in approximately 70 human proteins, often adjacent to other protein motifs (Jeanmougin F., et al., *Trends Biochem. Sci.,* 1997, 22, 5, 151-153; and Tamkun J. W., et al., *Cell,* 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.,* 33(3):146-153 (2012) and Muller et al., *Expert Rev.,* 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immune-inflammation, neurological disorders, and metabolic diseases. Bromodomains reside within key chromatin modifying complexes that serve to control distinctive disease-associated transcriptional pathways. An example of such a complex is the SWI/SNF chromatin-remodeling complex, which has been reported to be involved in gene regulation, cell lineage specification and development, and comprises a number of bromodomain containing subunits, including SMARCA4 (also known as BRG1), SMARCA2 (also known as BRM) and PB1 (also known as PBRM1) (see, Hohmann et al., *Trends in Genetics,* 30(8):356-363 (2014)). Inactivating mutations in SWI/SNF subunits have been reported to be found in nearly 20% of human cancers and recent studies have revealed synthetic lethal interactions between certain subunits (id). For example, SMARCA2 has been identified as a synthetic lethal target in SMARCA4-deficient cancers (Hoffman et al., *PNAS,* 111(8):3128-3133 (2014); Oike et al., *Cancer Research,* 73(17):5508-5518 (2013)). Additionally, other studies have shown that certain cancers lacking SWI/SNF mutations are sensitive to SMARCA2 inhibition. Hence, the selective inhibition of certain SWI/SNF subunits, including SMARCA2, SMARCA4 and PB1, creates varied opportunities for the development of novel therapeutic agents for the treatment of human dysfunction, including cancer.

The present disclosure describes bispecific compounds which function to recruit endogenous proteins to an E3 ubiquitin ligase for degradation, and methods of using the same. In particular, the present disclosure provides bispecific or proteolysis targeting chimeric (PROTAC) compounds, which find utility as modulators of targeted ubiquitination of a variety of polypeptides and other proteins, which are then degraded and/or otherwise inhibited by the bispecific compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds described herein for the treatment or amelioration of a disease condition, such as cancer, e.g., SMARCA4-mutated/deficient cancer, such as lung cancer or non-small cell lung cancer.

Thus, new approaches are needed to modulate SMARCA2, SMARCA4 and PB1 activity in the prevention and/or treatment of cancer and more particularly solid cancers such as carcinoma diseases. There remains a need for agents that exploit different mechanisms of action and may have better outcomes in terms of relief of symptoms, safety, and patient mortality, both short-term and long-term.

SUMMARY OF THE INVENTION

The present invention provides compounds which bind to bromodomain proteins, and more specifically bind to or inhibit SMARCA2 and/or SMARCA4. The present invention provides, in one aspect, substituted 3-pyridazinyl-2-phenols and 6-(1,2,4-triazinyl)-2-phenols which bind to SMARCA2 and/or SMARCA4. Certain compounds provided herein provide selective binding to SMARCA2 and/or SMARCA4 compared to binding association with other bromodomains including polybromo1 (known as PB1 and PBRM1) and the BET family of bromodomain proteins (e.g., BRD2, BRD3, BRD4 etc.). Certain compounds provided by the specification at least 10 fold greater binding affinity for SMARCA2 AND/OR SMARCA4 compared to other bromodomain containing proteins as measured by $IC_{50}$. In certain aspects, the compounds of the invention are at least 20 fold or 50 fold selective binders of SMARCA2 AND/OR SMARCA4 compared to other bromodomain containing proteins. Inhibition of SMARCA2 and/or SMARCA4 activity may be desirable in the treatment or prevention of a variety of diseases including cancer, particularly solid tumors, i.e., carcinomas. Inhibition of SMARCA2 and/or SMARCA4 activity may be particularly desirable in the treatment or prevention of a variety of diseases including lung, pancreatic, prostate, colon, breast, uterine, cervical, esophageal, renal carcinomas and rhabdoid cancers.

The invention provides, in one aspect, substituted 3-pyridazinyl-2-phenols and 6-(1,2,4-triazinyl)-2-phenols compounds which bind to bromodomains and more particularly bind to SMARCA2 or SMARCA4. Preferably, the substituted 3-pyridazinyl-2-phenols and 6-(1,2,4-triazinyl)-2-phenols compounds of the invention are SMARCA2 or SMARCA4 inhibitors.

The substituted pyridazine compounds of the invention are compounds and salts according to Formula (I):

(I)

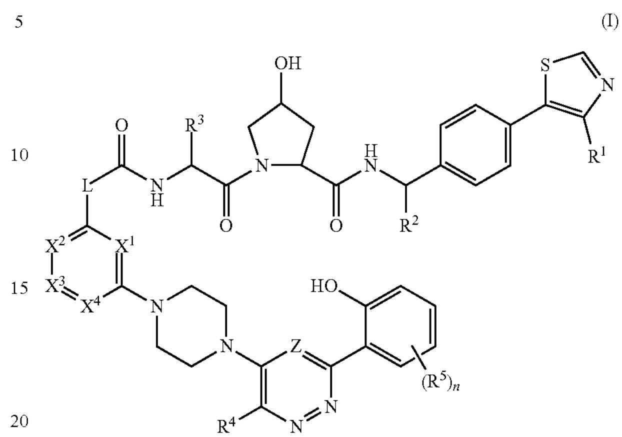

Also provided is a pharmaceutical composition comprising a pharmaceutically acceptable excipient, carrier or adjuvant and at least one compound of Formula (I) or subformulae thereof. Pharmaceutical compositions provided by the invention are suitable for use in the treatment of disease modulated by SMARCA2 AND/OR SMARCA4 activity. In certain aspects the pharmaceutical compositions of the invention are suitable for use in the treatment of diseases associated with changes in either chromatin silencing or chromatin remodeling, including cancers such as lung, pancreatic, prostate, colon, breast, uterine, cervical, esophageal, renal carcinomas and rhabdoid cancers.

Also provided is a packaged pharmaceutical composition, comprising a pharmaceutical composition comprising a pharmaceutically acceptable excipient, carrier or adjuvant and at least one compound of formula (I) or subformulae thereof, and instructions for using the composition to treat a patient suffering from a disease mediated by chromatin silencing or chromatin remodeling and that are dependent on the activity SMARCA2 and/or SMARCA4 activity. In certain instances, the patient is suffering from cancer or more particularly a solid tumor, e.g., rhabdoid cancers or a carcinoma of lung, pancreatic, prostate, colon, breast, uterine, cervical, esophageal, renal carcinomas. In certain aspects, a packaged pharmaceutical composition is provided for the treatment of adenocarcinoma of the lung, the composition comprising a pharmaceutical composition comprising a pharmaceutically acceptable excipient, carrier or adjuvant and at least one compound of formula (I) or subformulae thereof, and instructions for using the composition to treat a patient suffering from an adenocarcinoma of the lung.

Also provided is a method of treating or preventing disease in a mammal which method comprises administering to a mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof.

Also provided is a method for modulating SMARCA2 and/or SMARCA4 activity in a mammal, which method comprises administering to the mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof. Another aspect of the invention relates to a method of treating a SMARCA4 deficient or mutated disease or disorder, the method comprising administering a SMARCA2 and/or SMARCA4 inhibitor of the invention to a patient in need of therapy. In certain embodiments, the SMARCA4 mutated or deficient disease or disorder is selected from the group consisting of a lung, pancreatic, prostate, colon, breast, uterine, cervical, esophageal, renal carcinomas and rhabdoid cancers.

Also provided is the use, in the manufacture of a medicament for treating or preventing disease mediated by SMARCA2 and/or SMARCA4 activity, of at least one compound of formula I or subformulae thereof.

Also provided are methods of preparing compounds formula I or subformulae thereof.

Other aspects and embodiments will be apparent to those skilled in the art form the following detailed description.

DETAILED DESCRIPTION OF THE INVENTION

The invention related generally to compounds of Formula I and salts and tautomers thereof which bind to SMARCA2 and/or SMARCA4, more particularly that modulate SMARCA2 and/or SMARCA4 activity and in certain aspects inhibit SMARCA2 and/or SMARCA4 activity. In particular, the invention relates to compounds which selectively block SMARCA2 and/or SMARCA4 activity. Certain compounds provided herein selectively inhibit SMARCA2 and/or SMARCA4 activity in comparison to activity against other bromodomain proteins such as BRD7/9 that also associate with the SWI/SNF remodeling complex and other chromatin readers such as BRD4 and its closely related homologs. Certain compounds provided herein offer at least 10 fold selectivity for SMARCA2 and/or SMARCA4 inhibition compared to other bromodomain proteins. Other compounds provided herein offer at least 20 fold, 50 fold or 100 fold selectivity for SMARCA2 and/or SMARCA4 inhibition compared to other bromodomain proteins. While not wishing to be bound by theory, it is believed that selective inhibition of SMARCA2 and/or SMARCA4 activity may be particularly desirable for the treatment of diseases or disorders associated with either changes in SWI/SNF mediated chromatin remodeling or with altered activity of the poly comb repressive complex (PRC).

In a first embodiment compounds and salts thereof are provided, which compounds are represented by Formula (I):

(I)

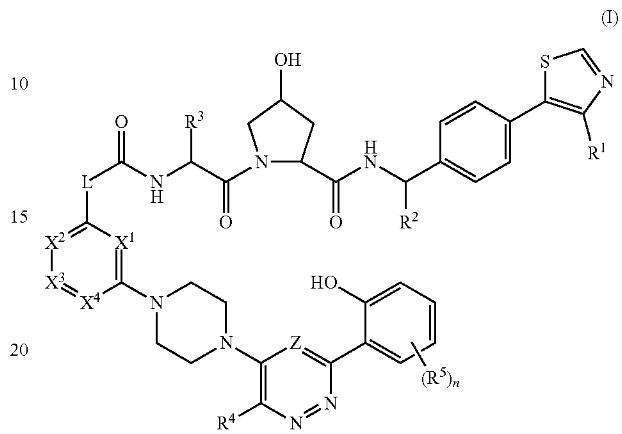

Wherein $R^1$ is hydrogen, halogen, $C_1$-$C_6$alkyl, hydroxy$C_1$-$C_6$alkyl, or $C_3$-$C_6$cycloalkyl;

$R^2$ is hydrogen, $C_1$-$C_6$alkyl, hydroxy$C_1$-$C_6$alkyl, or halo$C_1$-$C_6$alkyl;

$R^3$ is $C(CH_3)_2R^{3a}$ or $C_3$-$C_6$cycloalkyl wherein the cycloalkyl is optionally substituted with 0, 1, or 2 groups independently selected from the group consisting of halogen, hydroxy, hydroxy$C_1$-$C_6$alkyl, halo$C_1$-$C_6$alkyl, $C_1$-$C_6$alkoxy, and halo$C_1$-$C_6$alkoxy;

$R^{3a}$ is hydrogen, $C_1$-$C_6$alkyl, hydroxy$C_1$-$C_6$alkyl, or halo$C_r$$C_6$alkyl;

L is a bond or a divalent $C_1$-$C_6$alkanediyl linker;

$R^4$ is hydrogen or amino;

$R^5$ is independently selected at each occurrence from hydrogen and halogen;

n is 0, 1, 2 or 3;

$X^1$ is CH, N, O or S;

$X^2$ is CH, N, O or S, wherein 0 or 1 of $X^1$ and $X^2$ is an oxygen or sulfur atom;

$X^3$ is CH, N or absent;

$X^4$ is CH or N wherein $X^3$ is absent when $X^1$ or $X^2$ is O or S, and wherein at least two of $X^1$, $X^2$, $X^3$, and $X^4$ are CH or absent; or $X^1$ is —C(H)═C(H)—;

$X^2$ is CH or N;

$X^3$ is CH or N;

$X^4$ is absent; and

Z is CH or N.

In a second embodiment, a compound and salts thereof of the first embodiment is provided which compounds are represented by Formula II:

(II)

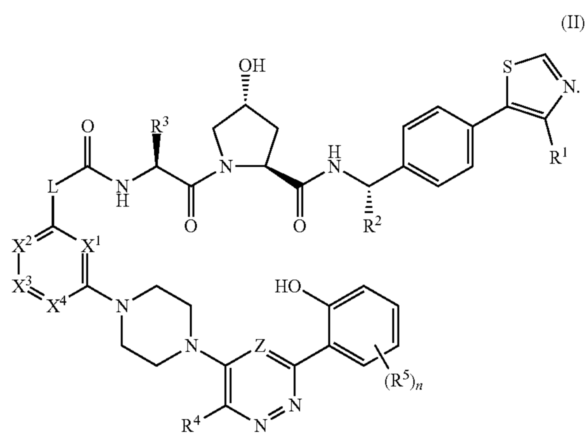

In a third embodiment, a compound or salt thereof of the first or second embodiment is provided in which $R^1$ is hydrogen, fluoro, chloro, methyl or ethyl.

In a fourth embodiment, a compound or salt thereof of the first or second embodiment is provided in which $R^1$ is hydrogen or methyl. In certain aspects of the third or fourth embodiment, a compound or salt thereof is provided in which $R^1$ is hydrogen. In other aspects of the third or fourth embodiment, a compound or salt thereof is provided in which $R^1$ is methyl.

In a fifth embodiment, a compound or salt thereof of any one of the first to fourth embodiments is provided in which $R^2$ is hydrogen, methyl or ethyl.

In a sixth embodiment, a compound or salt thereof of any one of the first to fifth embodiments is provided in which $R^3$ is isopropyl, tert-butyl, cyclopropyl, cyclobutyl, cyclopentyl, 1-methylcyclopropyl, 1-methylcyclobutyl or 1-methylcyclopentyl.

In a seventh embodiment, a compound or salt thereof of the sixth embodiment is provided in which $R^3$ is isopropyl or tert-butyl. In certain aspects of the sixth or seventh embodiment, a compound or salt thereof is provided in which $R^3$ is isopropyl. In other aspects of the sixth or seventh embodiment, a compound or salt thereof is provided in which $R^3$ is tert-butyl.

In an eighth embodiment, a compound or salt thereof of any one of the first to seventh embodiments is provided in which L is a bond, methylene ($—CH_2—$) or ethylene ($—CH_2CH_2—$).

In a ninth embodiment, a compound or salt thereof of the eighth embodiment is provided in which L is a bond.

In a tenth embodiment, a compound or salt thereof of the eighth embodiment is provided in which L is methylene ($—CH_2—$).

In an eleventh embodiment, a compound or salt thereof of any one of the first to tenth embodiments is provided in which $R^4$ is amino.

In a twelfth embodiment, a compound or salt thereof of any one of the first to eleventh embodiments is provided in which n is 0.

In a thirteenth embodiment, a compound or salt thereof of any one of the first to eleventh embodiments is provided in which n is 1 and $R^5$ is fluoro.

In a fourteenth embodiment, a compound or salt thereof of any one of the first to thirteenth embodiments is provided in which Z is CH.

In a fifteenth embodiment, a compound or salt thereof of any one of the first to fourteenth embodiments is provided in which each of $X^1$, $X^2$, $X^3$ and $X^4$ is CH.

In a sixteenth embodiment, a compound or salt thereof of any one of the first to fourteenth embodiments is provided in which each of $X^1$ is CH or N; and $X^2$, $X^3$ and $X^4$ are CH.

In a seventeenth embodiment, a compound or salt thereof of any one of the first to fourteenth embodiments is provided in which each of $X^1$ is N; and $X^2$, $X^3$ and $X^4$ are CH.

In an eighteenth embodiment, a compound or salt thereof of any one of the first to fourteenth embodiments is provided in which each of $X^4$ is CH or N; and $X^1$, $X^2$ and $X^3$ are CH.

In a nineteenth embodiment, a compound or salt thereof of any one of the first to fourteenth embodiments is provided in which each of $X^4$ is N; and $X^1$, $X^2$ and $X^3$ are CH.

In a twentieth embodiment, a compound or salt thereof of any one of the first to fourteenth embodiments is provided in which $X^1$ is CH, N or S; $X^2$ is CH; $X^3$ is absent; $X^4$ is CH or S, where at least one of $X^1$ and $X^4$ is not CH and at least one of $X^1$ and $X^4$ is not S.

In a twenty first embodiment, a compound or salt thereof of the twentieth embodiment is provided in which $X^1$ is N; $X^2$ is CH; $X^3$ is absent and $X^4$ is S.

In a twenty second embodiment, a compound or salt thereof of the twentieth embodiment is provided in which $X^1$ is S; $X^2$ and $X^4$ are each CH; and $X^3$ is absent In a twenty third embodiment, a compound or salt thereof of the first or second embodiment is represented by formula III:

(III)

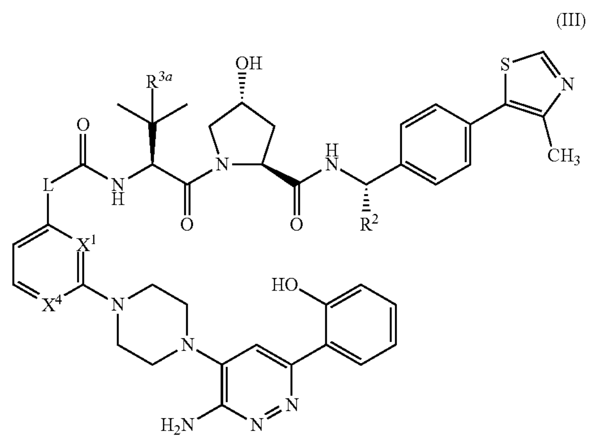

Wherein $R^2$ is hydrogen or methyl;

L is a bond or divalent methandiyl;

$R^{3a}$ is hydrogen or methyl;

$X^1$ is CH or N;

$X^4$ is CH or N, wherein at least one of $X^1$ and $X^4$ is CH.

In a twenty fourth embodiment, a compound or salt thereof of the first embodiment is provided which compound is selected from the group consisting of -continued
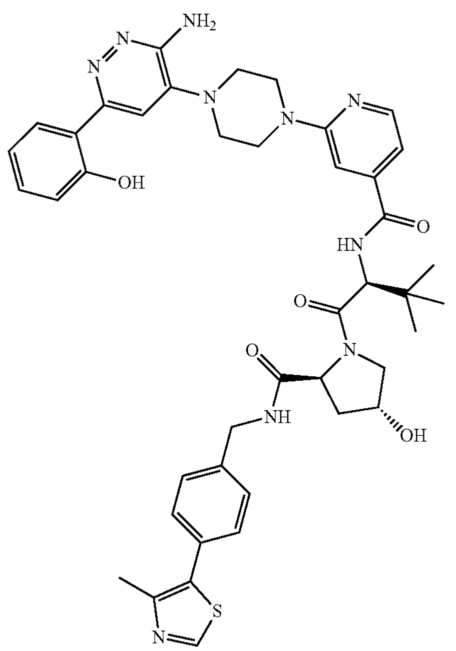
,
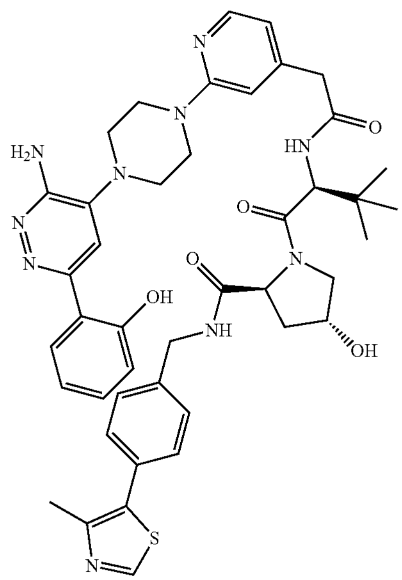
,
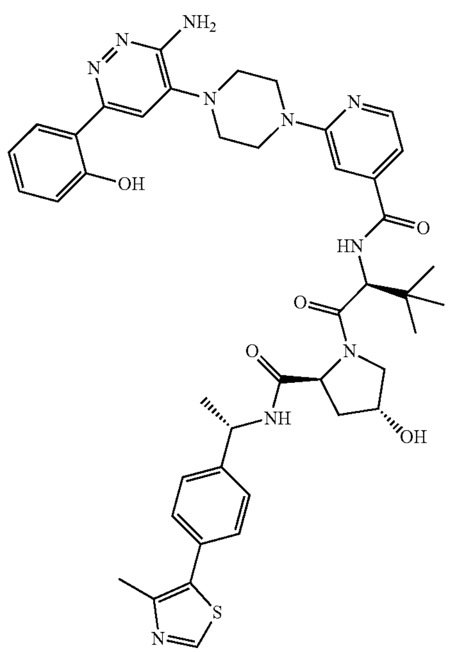
,
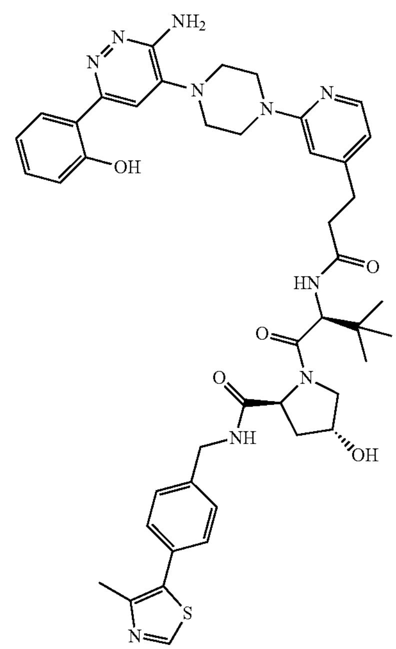
, -continued
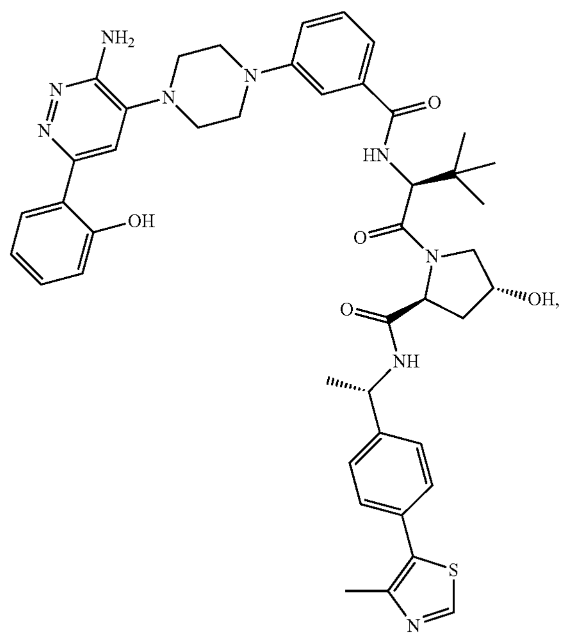
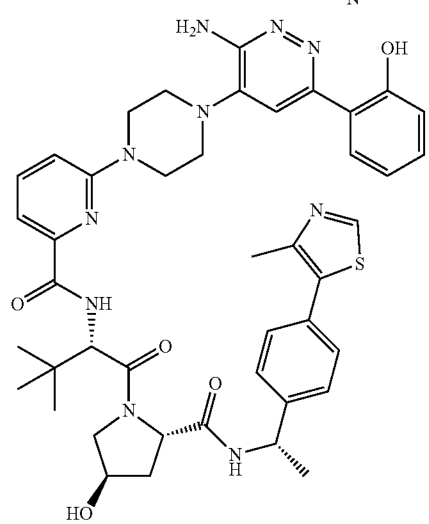
,
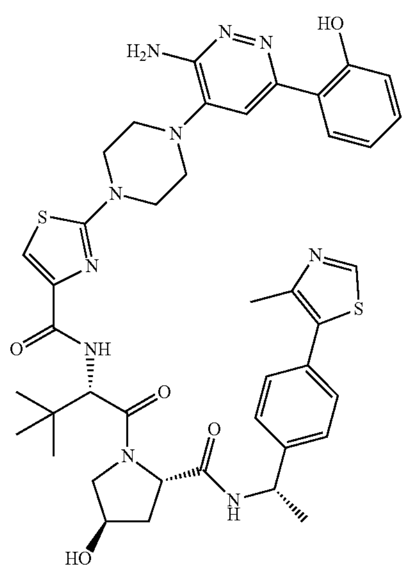
,
-continued
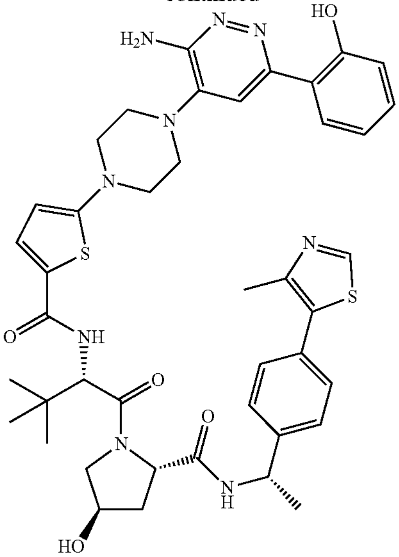
,
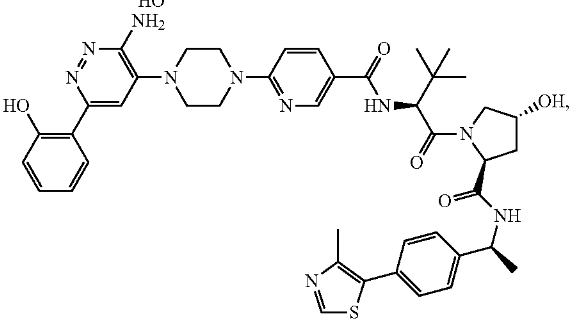
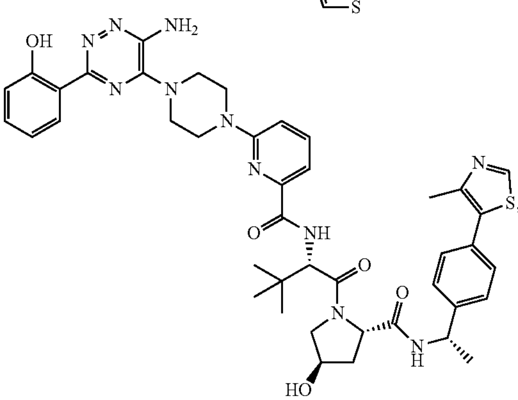
and
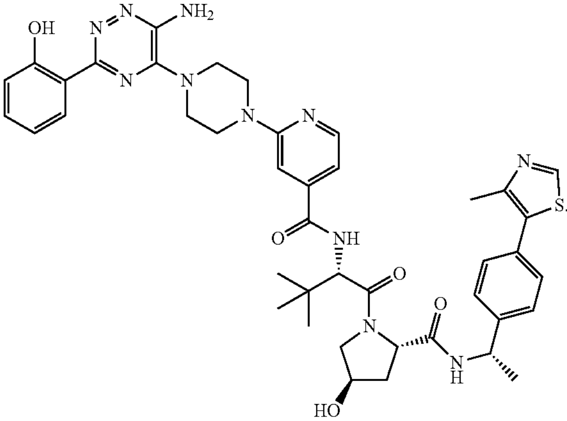
In another embodiment, pharmaceutical compositions are provided which comprise one or more pharmaceutically acceptable carriers and a therapeutically effective amount of a compound of any one of formulae I or a subformulae thereof. In some aspects, the composition is formulated in a form selected from the group consisting of an injectable fluid, an aerosol, a tablet, a pill, a capsule, a syrup, a cream, a gel and a transdermal patch. In certain aspects, the composition is preferably formulated in a form of an injectable fluid. Preferred injectable fluids are suitable for infusion administration, intravenous administration or subcutaneous administration.

In another embodiment, combinations, in particular pharmaceutical combinations, are provided which comprise a therapeutically effective amount of the compound any one of formulae I or a subformulae thereof.

In another embodiment, methods of modulating SMARCA2 and/or SMARCA4 activity in a subject are provided which comprise administering to the subject a therapeutically effective amount of Formula I or a subformulae thereof. In preferred aspects of the embodiment, methods of inhibiting SMARCA2 and/or SMARCA4 activity in a subject are provided, which comprise administering to the subject a therapeutically effective amount of a compound of Formula I or subformulae thereof. In certain aspects of the embodiment, method of inhibiting SMARCA2 and/or SMARCA4 activity in a subject are provided, which comprise administering to the subject a therapeutically effective amount of a compound of Formula I or subformulae thereof.

In yet other embodiments, methods of treating a disorder or a disease in a subject mediated by SMARCA2 and/or SMARCA4 activity are provided. The methods comprise administering to the subject a therapeutically effective amount of the compound of Formula I or a subformulae thereof.

In another embodiment, methods of treating or preventing a disease or disorder are provided where the disease or disorder is mediated by SMARCA2 and/or SMARCA4. In certain aspects, the disease or disorder is a SMARCA4 deficient or mutated disease or disorder. In certain aspects of the embodiment the disease or disorder is selected from lung, pancreatic, prostate, colon, breast, uterine, cervical, esophageal, renal carcinomas and rhabdoid cancers. In certain specific aspects of the embodiment, the disease or disorder is selected from the group consisting of lung, pancreatic, prostate, colon, breast, uterine, cervical, esophageal and renal carcinomas which method comprises the step of administering to a subject in need of therapy a therapeutically effective amount of a compound or salt of Formula I or a subformulae thereof. In certain aspects of this embodiment, the method comprises treating a disease or disorder selected from lung, pancreatic, prostate, colon, breast, uterine, cervical, esophageal, renal carcinomas and rhabdoid cancers. In certain instances, the treatment methods and/or the prevention methods are suitable for the treatment and or prevention of lung adenocarcinomas.

In another aspect, the invention provides for the use of compounds of Formula I or a subformulae thereof for use in the preparation of a medicament or for use in the manufacture of a medicament for the treatment of a disorder or disease in a subject mediated by SMARCA2 and/or SMARCA4. In certain aspects, the disease or disorder is a SMARCA4 deficient or mutated disease or disorder. In certain other aspects, the invention provides for the use of a compound according to formula I or a subformulae thereof in the treatment of a disease or disorder mediated by SMARCA2 and/or SMARCA4. In certain uses of the embodiment, the disease or disorder is selected from lung, pancreatic, prostate, colon, breast, uterine, cervical, esophageal, renal carcinomas and rhabdoid cancers. More particularly, the use of compounds of Formula I in the preparation of a medicament or in use in the manufacture of a medicament for treatment of a disease or disorder selected from human carcinomas and more particularly in the treatment of lung, pancreatic, prostate, colon, breast, uterine, cervical, esophageal, renal carcinomas and rhabdoid cancers. In certain instances, the invention provides for the use of compounds of Formula I or a subformulae thereof for use in the preparation of a medicament or for use in the manufacture of a medicament or the treatment of a disease or disorder in a subject selected from cancers such as lung, pancreatic, prostate, colon, breast, uterine, cervical, esophageal, renal carcinomas and rhabdoid cancers. In certain instances, the invention provides for the use of compounds of Formula I or a subformulae thereof for use in the preparation of a medicament or for use in the manufacture of a medicament or the treatment of SMARCA4 mutant adenocarcinoma of the lung.

For purposes of interpreting this specification, the following definitions will apply and whenever appropriate, terms used in the singular will also include the plural and vice versa.

As used herein, the term "PROTAC" refers to a bispecific molecule comprised of a ligand for a target protein, a linker, and a ligand for an E3 ligase. A target protein is a protein to receive ubiquitins by a PROTAC thereby tagging said target protein for destruction by the ubiquitin proteasome system (UPS) such as the 26S proteasome of the ubiquitin proteasome system. A "linker" refers to the spacer used to separate the ligand for the target protein from the ligand for the E3 ligase in the PROTAC molecule.

As used herein, the term "alkyl" refers to a fully saturated branched or unbranched hydrocarbon moiety having up to 20 carbon atoms. Unless otherwise provided, alkyl refers to hydrocarbon moieties having 1 to 20 carbon atoms, 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. Unless otherwise provided, alkylene refers to moieties having 1 to 20 carbon atoms, 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, which is substituted with one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "hydroxy alkyl" refers to an alkyl as defined herein which is substituted with one or more hydroxy groups. The term "hydroxy cycloalkyl-alkyl" refers to an alkyl group that is substituted with a cycloalkyl group, as defined herein, and further substituted with a hydroxy group. The hydroxy group can be on the alkyl group, the cycloalkyl group, or on each of the alkyl and cycloalkyl groups.

The term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl, naphthyl or tetrahydronaphthyl, each of which may optionally be substituted with 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

The term "aralkyl" refers to an alkyl group substituted with an aryl group or a heteroaryl group. Furthermore, the term "aralkyl" refers to alkyl groups having 1 to 4 carbon atoms and one or two aryl or heteroaryl groups attached to one or two carbon atoms of the alkyl group. Non-limiting examples of aralkyl include methyl, ethyl, or propyl substituted with one or two aryl or heteroaryl groups selected from phenyl, 1- or 2-naphthyl, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, and 5-pyrimidinyl. Certain preferred aralkyl groups include benzyl and naphthylmethyl. As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocycle," "heterocycloalkyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocycloalkyl can include fused or bridged rings as well as spirocyclic rings. Examples of heterocycles include tetrahydrofuran, dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, azetidine, thiazolidine, morpholine, and the like.

As used herein, the term "cycloalkyl" refers to saturated or partially unsaturated monocyclic, bicyclic or tricyclic hydrocarbon groups of 3-12 carbon atoms. For the avoidance of doubt, cycloalkyl is not intended to include aromatic groups such as naphthylene or phenyl. Unless otherwise provided, cycloalkyl refers to cyclic hydrocarbon groups having between 3 and 9 ring carbon atoms or between 3 and 7 ring carbon atoms, each of which can be optionally substituted with one, or two, or three, or more substituents independently selected from the group consisting of alkyl, halo, oxo, hydroxy, alkoxy, alkyl-C(O)—, acylamino, carbamoyl, alkyl-NH—, $(alkyl)_2N$—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl. 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. The term "hydroxy cycloalkyl" refers specifically to a cycloalkyl group substituted with one or more hydroxy groups.

As used herein, the term "heteroaryl" refers to a 5-14 membered monocyclic- or bicyclic- or tricyclic-aromatic ring system, having 1 to 8 heteroatoms selected from N, O and S. In certain preferred aspects, the heteroaryl is a 5-10 membered ring system (e.g., 5-7 membered monocycle or an 8-10 membered bicycle) or a 5-7 membered ring system. Exemplary monocyclic heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, and 5-pyrimidinyl. Exemplary bicyclic heteroaryl groups include 1-, 3-, 4-, 5-, 6-, 7-, or 8-isoquinolinyl, 2-, 3-, 4-, 5-, 6-, 7-, or 8-quinolinyl, 1-, 3-, 4-, 5-, 6-, 7-, or 8-isoquinolinyl, 1-, 2-, 4-, 5-, 6-, 7-, or 8-benzimidazolyl and 1-, 2-, 3-, 4-, 5-, 6-, 7-, or 8-indolyl.

The term "heteroaryl" also refers to a group in which a heteroaromatic ring is fused to one or more aryl, cycloaliphatic, or heterocyclyl rings, where the radical or point of attachment is on the heteroaromatic ring.

As used herein, the term "halogen" or "halo" refers to fluoro, chloro, bromo, and iodo.

As used herein, the term "optionally substituted" unless otherwise specified refers to a group that is unsubstituted or is substituted with one or more, typically 1, 2, 3 or 4, suitable non-hydrogen substituents. If the identity of the "optional substituent" is not clearly defined in context of the optionally substituted group, then each optional substituent is independently selected from the group consisting of: alkyl, hydroxy, halogen, oxo, amino, alkylamino, dialkylamino, alkoxy, cycloalkyl, $CO_2H$, heterocycloalkyloxy (which denotes a heterocyclic group bonded through an oxygen bridge), —$CO_2$alkyl, mercapto, nitro, cyano, sulfamoyl, sulfonamide, aryl, —OC(O)alkyl, —OC(O)aryl, aryl-S—, aryloxy; alkylthio, formyl (i.e., HC(O)—), —C(O)$NH_2$, aralkyl (alkyl substituted with aryl), aryl and aryl substituted with alkyl, cycloalkyl, alkoxy, hydroxy, amino, alkyl-C(O)—NH—, alkylamino, dialkylamino or halogen. It is understood that where a group is indicated to be optionally substituted, the disclosure includes embodiments in which the group is unsubstituted as well as embodiments in which the group is substituted.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The use of "rel" indicates that the diastereomeric orientation is known but the absolute stereochemistry is not. In cases where the absolute stereochemistry has not been determined the optical rotation and/or chiral chromatography conditions will indicate which isomer is present.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line or retention time on chiral chromatography separation. Certain of the compounds described herein contain one or more asymmetric centers or axes and may thus give rise to enantiomers, diastereomers, and other stereoisomeric forms that may be defined, in terms of absolute stereochemistry, as (R)- or (S)-, or with the (+) or (−) sign. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

It is understood that for any compound provided herein, including any compound of Formula (I), or any embodiment thereof, or a salt of any of the foregoing, the compound may exist in any stereochemical form, such as a single enantiomer, diastereomer, or tautomer or a mixture of one or more enantiomers, diastereomers, and tautomers in any ratio.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper. In certain other embodiments, the salts are selected from ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds as disclosed herein in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds as disclosed herein in $C_1$-$C_4$alkyl sulfonic acid, benzenesulfonic acid or mono-, di- or tri-$C_1$-$C_4$alkyl substituted benzene sulfonic acid addition salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{124}I$, $^{125}I$ respectively. The invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has at least 50% deuterium incorporation at each designated deuterium atom, 60% deuterium incorporation, at least 75% deuterium incorporation, at least 90% deuterium incorporation, at least 95% deuterium incorporation, at least 99% deuterium incorporation, or at least 99.5% deuterium incorporation.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (i) mediated by SMARCA2 and/or SMARCA4 activity, or (ii) associated with SMARCA2 and/or SMARCA4 activity; or (2) inhibiting the activity of SMARCA2 and/or SMARCA4. In another non-limiting embodiment, the term "a therapeutically effective amount" refers to the amount of the compound of the present invention that, when administered to a cell, or a tissue, or a non-cellular biological material, or a medium, is effective to at least partially inhibit SMARCA2 and/or SMARCA4 activity.

As used herein, the term "subject" refers to an animal Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevent," "preventing" or "prevention" of any disease or disorder refers in one embodiment, to delay or avoidance of onset of the disease or disorder (i.e., slowing or preventing the onset of the disease or disorder in a patient susceptible to development of the disease or disorder).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I. Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Intermediates and final products can be worked up and/or purified according to standard methods, e.g. using chromatographic methods, distribution methods, (re-)crystallization, and the like.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any process steps disclosed herein can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methylcyclohexane, or mixtures of those solvents, for example aqueous solutions, unless otherwise indicated in the description of the processes. Such solvent mixtures may also be used in working up, for example by chromatography or partitioning.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp, 1289-1329). Except insofar as any conventional carrier is incompatible with the active ingredient, its use in the therapeutic or pharmaceutical compositions is contemplated.

Typically, the pharmaceutical compositions are tablets or gelatin capsules comprising the active ingredient together with one or more of: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners. Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin. Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives. As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds disclosed herein in free form or in pharmaceutically acceptable salt form, exhibit valuable pharmacological properties, e.g. SMARCA protein modulating properties and more particularly inhibition of SMARCA2 and/or SMARCA4 protein activity, e.g. as indicated in in vitro and in vivo tests as provided in the next sections and are therefore indicated for therapy.

The present invention provides methods of treating a disease or disorder associated with SMARCA2 and/or SMARCA4 activity by administering to a subject in need thereof an effective amount of a compound disclosed herein. In certain aspects, diseases and disorders associated with SMARCA4 deficiencies or mutations are suitable for therapy by administration of a compound of the invention. In certain aspects, the disease or disorder suitable for therapy by administration of the compound of the invention include, but are not limited to human carcinomas such as lung, pancreatic, prostate, colon, breast, uterine, cervical, esophageal, renal carcinomas and rhabdoid cancers. In certain aspects, methods of treating lung adenocarcinoma by administration of a compound of the invention to a patient are provided.

In a specific embodiment, the present invention provides a method of treating or preventing lung adenocarcinoma by administering to a subject in need thereof an effective amount of a compound disclosed herein.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

The activity of a compound according to the present invention can be assessed by in vitro & in vivo methods, such as those described in the examples below.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound disclosed herein and at least one other therapeutic agent as a combined preparation for simultaneous, separate or sequential use in therapy. In one embodiment, the therapy is the treatment of a disease or condition mediated by SMARCA2 and/or SMARCA4 activity. In preferred aspects, the therapy is a treatment for human carcinomas such as, but not limited to lung, pancreatic, prostate, colon, breast, uterine, cervical, esophageal, renal carcinomas and rhabdoid cancers, including, but not limited to, lung and uterine carcinomas.

Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In one embodiment, the invention provides a pharmaceutical composition comprising a compound as disclosed herein and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound as disclosed herein for treating a disease or condition mediated by SMARCA2 and/or SMARCA4 activity wherein the medicament is prepared for administration with another therapeutic agent. The invention also provides the use of another therapeutic agent for treating a disease or condition mediated by SMARCA2 and/or SMARCA4 activity, wherein the medicament is administered with a compound as disclosed herein. In another aspect, the invention provides the use of a compound as disclosed herein for treating a human carcinoma selected from lung, pancreatic, prostate, colon, breast, uterine, cervical, esophageal, renal carcinomas and rhabdoid cancers or in certain aspects from lung and uterine carcinomas, wherein the medicament is prepared for administration with another therapeutic agent. The invention also provides the use of another therapeutic agent for treating a disease or disorder selected from human carcinoma selected from lung, pancreatic, prostate, colon, breast, uterine, cervical, esophageal, renal carcinomas and rhabdoid cancers or in certain aspects from lung and uterine carcinomas wherein the medicament is administered with a compound as disclosed herein.

The invention also provides a compound as disclosed herein for use in a method of treating a disease or condition mediated by SMARCA2 and/or SMARCA4 activity wherein the compound is prepared for administration with another therapeutic agent. The invention also provides another therapeutic agent for use in a method of treating a disease or condition mediated by SMARCA2 and/or SMARCA4 activity, wherein the other therapeutic agent is prepared for administration with a compound as disclosed herein. The invention also provides a compound as disclosed herein for use in a method of treating a disease or condition mediated by SMARCA2 and/or SMARCA4 activity, wherein the compound is administered with another therapeutic agent. The invention also provides another therapeutic agent for use in a method of treating a disease or condition mediated by SMARCA2 and/or SMARCA4 activity, wherein the other therapeutic agent is administered with a compound as disclosed herein.

The invention also provides the use of a compound as disclosed herein for treating a disease or condition mediated by SMARCA2 and/or SMARCA4 activity wherein the patient has previously (e.g. within 24 hours) been treated with another therapeutic agent. The invention also provides the use of another therapeutic agent for treating a disease or condition mediated by SMARCA2 and/or SMARCA4 activity wherein the patient has previously (e.g. within 24 hours) been treated with a compound as disclosed herein.

The pharmaceutical compositions can be administered alone or in combination with other molecules known to have a beneficial effect in treatment of disease associated with SMARCA2 and/or SMARCA4 activity or more particularly in the treatment of human carcinomas. In certain aspects, the pharmaceutical compositions provided may be administered alone or in combination with other molecules known to have a beneficial effect in treatment of a human carcinomas, including but not limited to lung, pancreatic, prostate, colon, breast, uterine, cervical, esophageal, renal carcinomas and rhabdoid cancers. In certain aspects, the pharmaceutical composition has a beneficial effect in the treatment of a disease selected from lung and uterine carcinomas. A combination therapy regimen may be additive, or it may produce synergistic results (e.g., improvement in mitochondrial function which is more than expected for the combined use of the two agents). In some embodiments, the present invention provide a combination therapy for preventing and/or treating a SMARCA2 and/or SMARCA4 mediated disease or more particularly human carcinomas selected from lung, pancreatic, prostate, colon, breast, uterine, cervical, esophageal, renal carcinomas and rhabdoid cancers and more particularly selected from lung and uterine carcinomas or from lung adenocarcinoma with a compound of the invention and a second therapeutic agent.

In one embodiment, the invention provides a method of inhibiting the activity of SMARCA2 and/or SMARCA4, in a subject, wherein the method comprises administering to the subject a therapeutically effective amount of the compound according to the definition of Formula (I). The invention further provides methods of inhibiting the activity of SMARCA2 and/or SMARCA4 protein in a subject by administering a compound as disclosed herein, wherein the method comprises administering to the subject a therapeutically effective amount of the compound as disclosed herein.

In one embodiment, the invention provides a compound as disclosed herein, for use as a medicament.

In one embodiment, the invention provides the use of a compound as disclosed herein for the treatment of a disorder or disease in a subject characterized by the activity of SMARCA2 and/or SMARCA4. In particular, the invention provides the use of a compound as disclosed herein for the treatment of a disorder or disease mediated by the activity of SMARCA2 and/or SMARCA4, e.g., a human carcinoma, including but not limited to lung, pancreatic, prostate, colon, breast, uterine, cervical, esophageal, renal carcinomas and rhabdoid cancers and particularly to lung and uterine carcinomas. In certain preferred aspects, the invention provides for the use of a compound as disclosed herein for the treatment of lung adenocarcinoma.

In one embodiment, the invention provides the use of a compound as disclosed herein in the manufacture of a medicament for the treatment of a disorder or disease in a subject characterized by activity of SMARCA2 and/or SMARCA4. More particularly in the manufacture of a medicament for the treatment of a disease or disorder in a subject characterized by activity of SMARCA2 and/or SMARCA4, e.g., a human carcinoma, including but not limited to lung, pancreatic, prostate, colon, breast, uterine, cervical, esophageal, renal carcinomas and rhabdoid cancers and particularly to lung and uterine carcinomas. In certain preferred aspects, the invention provides the use of a compound as disclosed herein in the manufacture of a medicament for the treatment of lung adenocarcinoma.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. Unless otherwise stated, reactions were run at room temperature.

Commercially available materials were purchased from Millipore-Sigma, HDH Pharma, Pharmablock, Alfa Aesar, Enovation Chemicals, and Combi-Blocks.

Compound names, i.e., IUPAC names, for compounds described in the instant application were generated using ChemDraw compound naming software.

Abbreviations: The Following Abbreviations May be Used Herein

AcOH acetic acid
aq or aq. aqueous
BOC or Boc tert-butyloxycarbonyl
DCE 1,2-dichloroethane
DABCO 1,4-diazabicyclo[2.2.2]octane
DCM dichloromethane
DMAP 4-dimethylaminopyridine
DME 1,2-dimethoxyethane
DMF N,N-dimethylformamide
DMSO dimethyl sulfoxide
Dppf, DPPF or dppf 1,1'-bis(diphenylphosphino)ferrocene
eq or eq. or equiv. equivalent
ESI or ES electrospray ionization
Et ethyl
$Et_2O$ diethyl ether
EtOAc ethyl acetate
g gram(s)
h hour(s)
HBTU N,N,N'N'-tetramethyl-O-(1H-benzotriazol-1-yl) uronium hexafluorophosphate, O-(Benzotriazol-1-yl)-N,N,N'N'-tetramethyluronium hexafluorophosphate
HPLC high pressure liquid chromatography
iPr iso-propyl
$iPr_2NEt$ or DIPEA N-ethyl diisopropylamine (Hünig's base)
KHMDS potassium hexamethyldisilazide
KOAc potassium acetate
Lawesson's reagent 2,4-bis(4-methoxyphenyl)-2,4-dithioxo-1,3,2,4-dithiadiphosphetane, 2,4-bis-(4-methoxyphenyl)-1,3-dithia-2,4-diphosphetane 2,4-disulfide
LC MS, LCMS, LC-MS or LC/MS liquid chromatography mass spectroscopy
LG leaving group (e.g., halogen, mesylate, triflate)
LHMDS or LiHMDS lithium hexamethyldisilazide
m/z mass divided by charge
Me methyl
MeCN acetonitrile
MeOH methanol
mg milligrams
min minutes
mL milliliters MS mass spectra NaHMDS sodium hexamethyldisilazide NBS N-bromosuccinimide n-BuLi n-butyllithium NCS N-chlorosuccinimide NMR nuclear magnetic resonance $Pd_2(dba)_3$ tris(dibenzylideneacetone)dipalladium(0)

$Pd(dppf)Cl_2 \cdot DCM$, $Pd(dppf)Cl_2$ [1,1'-bis(diphenylphosphino)ferrocene]dichloropalladium(II), complex with dichloromethane $Pd(PPh_3)_4$ tetrakis(triphenylphosphine)palladium(0)

Ph phenyl

PR or PG or Prot. group protecting group rbf round-bottom flask

RP-HPLC reverse phase high pressure liquid chromatography

RT or rt or r.t. room temperature sat. or satd. saturated

SFC supercritical fluid chromatography

TBAF tetra-n-butylammonium fluoride t-BuOH tert-butanol

TEA or $Et_3N$ trimethylamine

TFA trifluoroacetic acid

THF tetrahydrofuran

UV ultraviolet (2S,4R)-1-(S)-2-Amino-3,3-dimethylbutanoyl)-4-hydroxy-N-(4-(4-methylthiazol-5-yl)benzyl)pyrrolidine-2-carboxamide Hydrochloride (Intermediate 1)

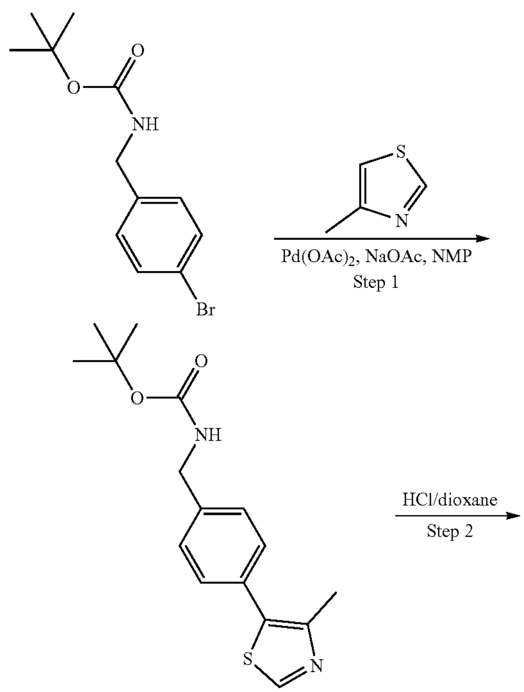

-continued

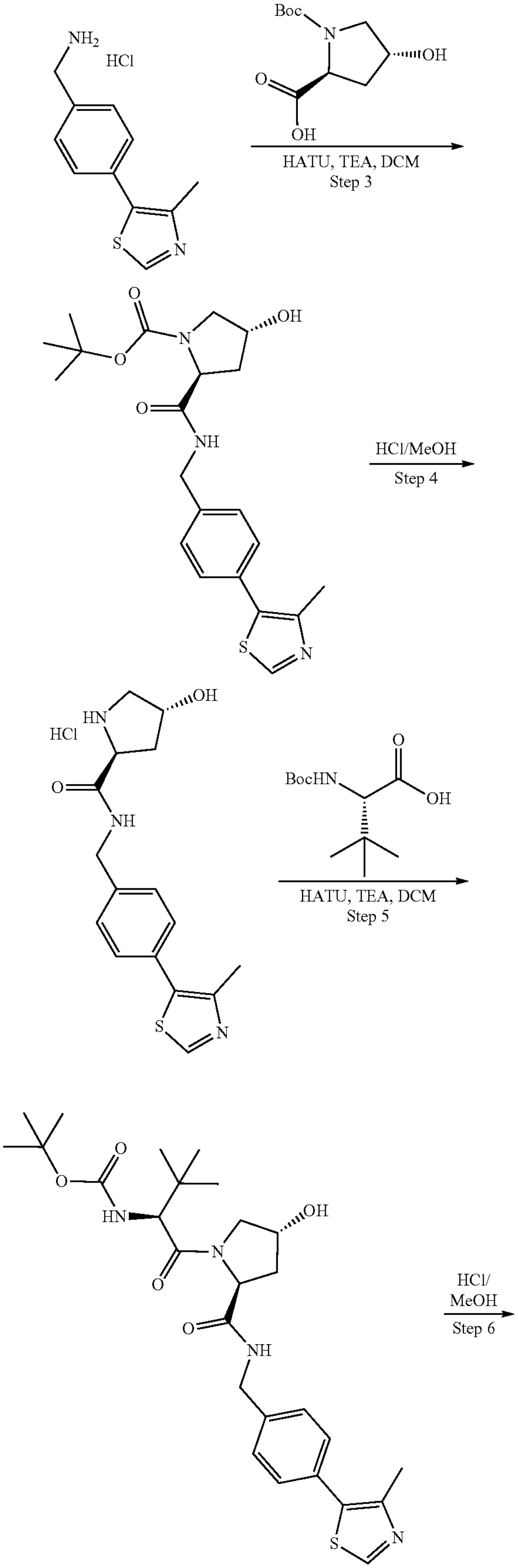

-continued

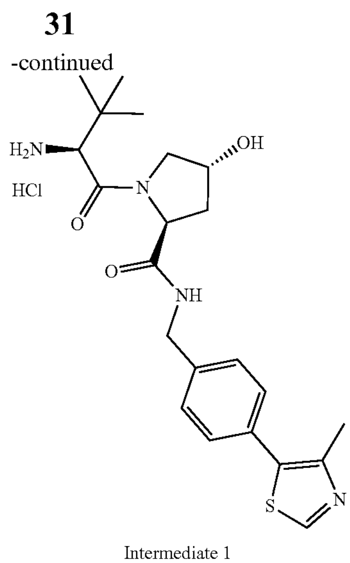

Intermediate 1

Step 1: tert-Butyl (4-(4-methylthiazol-5-yl)benzyl)carbamate. A mixture of tert-butyl (4-bromobenzyl)carbamate (100 g, 349 mmol), 4-methylthiazole (42 g, 419 mmol), $Pd(OAc)_2$ (784 mg, 3.49 mmol) and KOAc (69 g, 699 mmol) in NMP (600 mL) was stirred at 140° C. for 18 h under an atmosphere of nitrogen. The reaction mixture was diluted with $H_2O$ (1-L) and extracted with EtOAc (3×200 mL). The combined organic layers were washed with brine (3×200 mL), dried over anhydrous $Na_2SO_4$, filtered and concentrated under reduced pressure. The crude residue was purified by column chromatography on silica gel eluting with petroleum ether/EtOAc 50:1 to 2:1 to afford tert-butyl (4-(4-methylthiazol-5-yl)benzyl)carbamate (60 g, 197 mmol, 56% yield) as yellow solid.

Step 2: (4-(4-Methylthiazol-5-yl)phenyl)methanamine hydrochloride. To a solution of tert-butyl (4-(4-methylthiazol-5-yl)benzyl)carbamate (21 g, 69 mmol) in MeOH (200 mL) was added HCl/MeOH (4 M, 172 mL) drop-wise. After addition, the mixture was stirred at 15° C. for 2 h. The mixture was concentrated under reduced pressure (rotary evaporator) to afford crude (4-(4-methylthiazol-5-yl)phenyl) methanamine hydrochloride (17 g) as yellow solid.

Step 3: tert-Butyl (2S,4R)-4-hydroxy-2-((4-(4-methylthiazol-5-yl)benzyl)carbamoyl)pyrrolidine-1-carboxylate. To a solution of (4-(4-methylthiazol-5-yl)phenyl)methanamine hydrochloride (27 g, 112 mmol), (2S,4R)-1-(tert-butoxycarbonyl)-4-hydroxypyrrolidine-2-carboxylic acid (27 g, 118 mmol) and HATU (64 g, 168 mmol) in DCM (300 mL) was added $Et_3N$ (54 mL, 392 mmol) at 15° C. After addition, the mixture was stirred at 15° C. for 12 h. The reaction mixture was quenched with water (200 mL), the organic layer separated and the aqueous phase was extracted with DCM (2×100 mL). The combined organic phase was washed with brine (2×100 mL), dried over anhydrous $Na_2SO_4$, filtered and concentrated under reduced pressure (rotary evaporator). The crude residue was purified by column chromatography on silica gel eluting with 100:1-50:1 DCM in MeOH to afford tert-butyl (2S,4R)-4-hydroxy-2-((4-(4-methylthiazol-5-yl)benzyl)carbamoyl)pyrrolidine-1-carboxylate (23 g, 55 mmol, 49% yield) as white solid. $^1H$ NMR (400 MHz, $CDCl_3$) δ ppm 8.64 (s, 1H), 7.24-7.35 (m, 4H), 4.38-4.52 (m, 4H), 3.47-3.51 (m, 2H), 3.14-3.19 (m, 2H), 2.47 (s, 3H), 1.28-1.40 (m, 9H).

Step 4: (2S,4R)-4-Hydroxy-N-(4-(4-methylthiazol-5-yl)benzyl)pyrrolidine-2-carboxamide hydrochloride. To a solution of tert-butyl (2S,4R)-4-hydroxy-2-((4-(4-(4-methylthiazol-5-yl)benzyl)carbamoyl)pyrrolidine-1-carboxylate (23 g, 55 mmol) in MeOH (20 mL) was added HCl/MeOH (4 M, 137 mL), then the mixture was stirred at 15° C. for 2 h. The mixture was concentrated under reduced pressure (rotary evaporator) at 40° C. to give crude (2S,4R)-4-hydroxy-N-(4-(4-methylthiazol-5-yl)benzyl)pyrrolidine-2-carboxamide hydrochloride (17 g) as white solid. $^1H$ NMR (400 MHz, DMSO-$d_6$) δ ppm 9.07 (s, 1H), 7.45 (d, J=8.0 Hz, 2H), 7.36 (d, J=8.0 Hz, 2H), 4.30-4.40 (m, 4H), 3.30-3.35 (m, 1H), 2.95-3.05 (m, 3H), 2.43 (s, 3H).

Step 5: tert-Butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate. To a solution of (2S, 4R)-4-hydroxy-N-(4-(4-methylthiazol-5-yl)benzyl) pyrrolidine-2-carboxamide hydrochloride (14.5 g, 41 mmol) and (S)-2-((tert-butoxycarbonyl)amino)-3,3-dimethylbutanoic acid (10.4 g, 45 mmol) in DCM (200 mL) was added HATU (23.4 g, 61 mmol) followed by $Et_3N$ (28 mL, 20.7 g, 205 mmol). After addition, the mixture was stirred at 15° C. for 12 h. The mixture was diluted with DCM (200 mL), washed with water (2×200 mL), brine (200 mL), dried with $Na_2SO_4$, filtered and concentrated under reduced pressure (rotary evaporator). The residue was purified by column chromatography on silica gel eluting with 100:1 to 50:1 DCM in MeOH to afford tert-butyl ((S)-1-((2S,4R)-4-hydroxy-2-((4-(4-(4-methylthiazol-1-yl)benzyl)carbamoyl) pyrrolidin-1-yl)-3,3-dimethyl-1-oxobutan-2-yl)carbamate (14 g, 26.4 mmol, 64% yield) as white solid. $^1H$ NMR (400 MHz, $CDCl_3$) δ ppm 8.66 (s, 1H), 7.42-7.45 (m, 1H), 7.24-7.34 (m, 4H), 5.18-5.21 (m, 1H), 4.72 (t, J=8.0 Hz, 1H), 4.50-4.52 (m, 2H), 4.27-4.30 (m, 1H), 4.15 (d, J=9.2 Hz, 1H), 4.00-4.02 (m, 1H), 3.56-3.60 (m, 1H), 3.17-3.21 (m, 1H), 2.47 (s, 3H), 2.08-2.12 (m, 1H), 1.36 (s, 9H), 0.89 (s, 9H).

Step 6: (2S,4R)-1-(S)-2-Amino-3,3-dimethylbutanoyl)-4-hydroxy-N-(4-(4-methylthiazol-5-yl)benzyl)pyrrolidine-2-carboxamide hydrochloride (Intermediate 1). To a solution of tert-butyl ((S)-1-((2S,4R)-4-hydroxy-2-((4-methylthiazol-5-yl)benzyl)carbamoyl)pyrrolidin-1-yl)-3,3-dimethyl-1-oxobutan-2-yl)carbamate (14 g, 26 mmol) in MeOH (140 mL) was added HCl/MeOH (4 M, 66 mL) drop-wise. After addition, the mixture was stirred at 15° C. for 2 h. The mixture was concentrated under reduced pressure (rotary evaporator) at 40° C. to afford crude (2S,4R)-1-(S)-2-amino-3,3-dimethylbutanoyl)-4-hydroxy-N-(4-(4-methylthiazol-5-yl)benzyl)pyrrolidine-2-carboxamide hydrochloride (Intermediate 1, 13 g) as white solid. $^1H$ NMR (400 MHz DMSO-$d_6$) δ ppm 9.05 (s, 1H), 8.73 (t, J=5.6 Hz, 1H), 7.38 (s, 4H), 4.52-4.54 (m, 1H), 4.35-4.39 (m, 2H), 4.23-4.24 (m, 1H), 3.63-3.65 (m, 2H), 3.48-3.51 (m, 1H), 3.01-3.04 (m, 1H), 2.43 (s, 3H), 2.07-2.09 (m, 1H), 1.84-1.86 (m, 1H), 0.98 (s, 9H).

2-(4-(3-Amino-6-(2-hydroxyphenyl)pyridazin-4-yl)piperazin-1-yl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)isonicotinamide (Example 1)
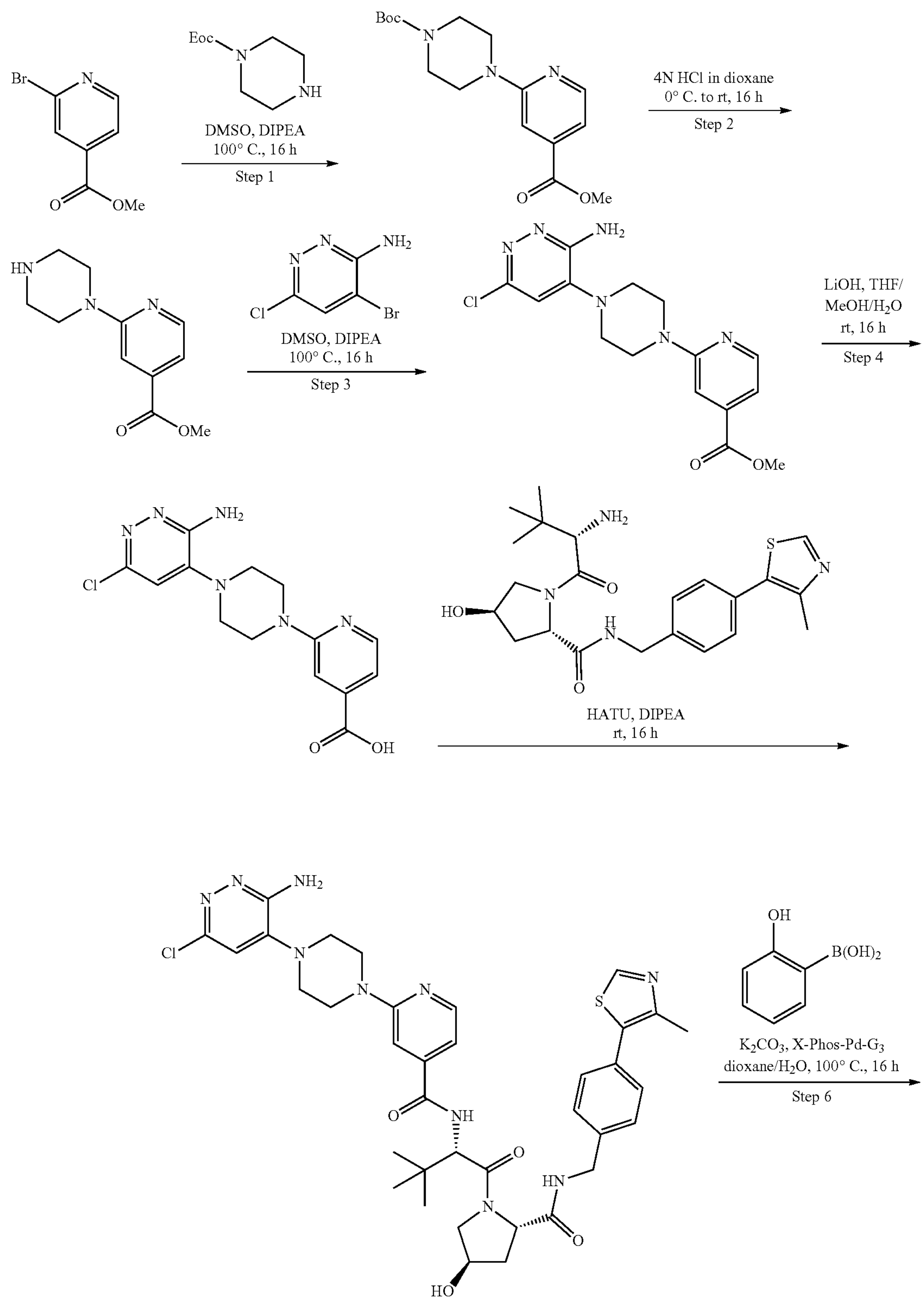

-continued

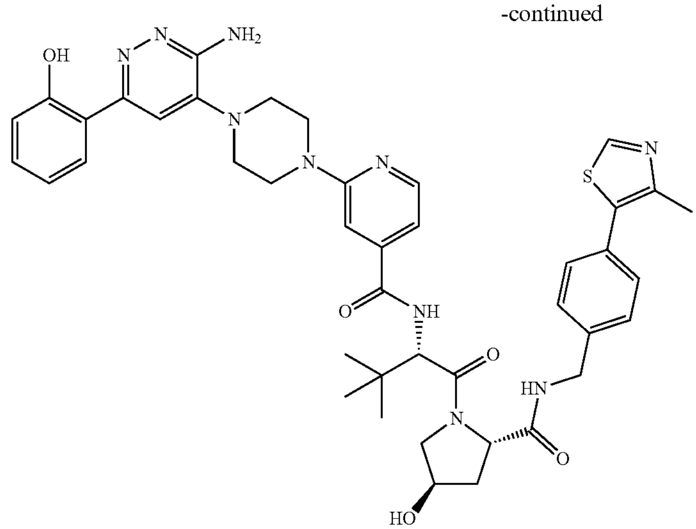

Example 1

Step 1: tert-Butyl 4-(4-(methoxycarbonyl)pyridin-2-yl) piperazine-1-carboxylate. To a solution of methyl 2-bromoisonicotinate (3.00 g, 13.89 mmol, Combi Blocks) and tert-butyl piperazine-1-carboxylate (3.88 g, 20.83 mmol, Spectrochem) in DMSO (30 mL) was added DIPEA (7.28 mL, 41.7 mmol). The reaction mixture was stirred at 100° C. for 16 h. The reaction mixture was quenched with ice-cold water and extracted with EtOAc and the combined organic extract was dried over sodium sulfate, filtered, concentrated under reduced pressure (rotary evaporator) and purified by column chromatography on silica gel using 0-20% EtOAc in petroleum ether to afford tert-butyl 4-(4-(methoxycarbonyl) pyridin-2-yl)piperazine-1-carboxylate (1.50 g, 4.67 mmol, 34% yield) as off-white solid. $^1$H NMR (400 MHz, DMSO-$d_6$): δ ppm 8.28 (d, J=5.1 Hz, 1H), 7.22 (s, 1H), 7.06 (dd, J=5.1, 1.3 Hz, 1H), 3.86 (s, 3H), 3.54 (dd, J=6.8, 3.8 Hz, 4H), 3.42 (dd, J=6.8, 3.8 Hz, 4H), 1.42 (s, 9H). m/z (ESI): 322 $(M+H)^+$.

Step 2: Methyl 2-(piperazin-1-yl)isonicotinate. To a solution of tert-butyl 4-(4-(methoxycarbonyl)pyridin-2-yl)piperazine-1-carboxylate (1.50 g, 4.67 mmol) in 1,4-dioxane (15 mL) was added 4 M HCl in dioxane (15 mL, 60 mmol) dropwise at 0° C. and stirred for 16 h at r.t. The reaction mixture was concentrated under reduced pressure (rotary evaporator) to afford crude (1.4 g) as off-white solid. The crude was directly taken forward to the next step. $^1$H NMR (300 MHz, DMSO-$d_6$): δ ppm 9.52 (s, 2H), 8.30 (d, J=5.2 Hz, 1H), 7.38 (s, 1H), 7.16 (dt, J=5.2, 1.1 Hz, 1H), 3.88 (s, 3H), 3.82-3.86 (m, 4H), 3.16-3.20 (m, 4H). m/z (ESI): 222 $(M+H)^+$.

Step 3: Methyl 2-(4-(3-amino-6-chloropyridazin-4-yl) piperazin-1-yl)isonicotinate. To a solution of methyl 2-(piperazin-1-yl)isonicotinate hydrochloride (1.40 g, 5.43 mmol) and 4-bromo-6-chloropyridazin-3-amine (1.25 g, 5.98 mmol, Combi Blocks) in DMSO (14 mL) was added DIPEA (4.74 mL, 27.2 mmol) and stirred at 100° C. for 16 h. The reaction mixture was quenched with ice-cold water and extracted with EtOAc. The combined organic layers were washed with brine, dried over anhydrous $Na_2SO_4$, concentrated under reduced pressure (rotary evaporator) and purified by column chromatography on silica gel eluting with 0-20% MeOH in DCM to afford methyl 2-(4-(3-amino-6-chloropyridazin-4-yl)piperazin-1-yl)isonicotinate (0.90 g, 2.58 mmol, 48% yield) as off white solid. $^1$H NMR (300 MHz, DMSO-$d_6$): δ ppm 8.32 (d, J=5.1 Hz, 1H), 7.28 (s, 1H), 7.09 (d, J=5.0 Hz, 1H), 6.95 (s, 1H), 6.26 (s, 2H), 3.88 (s, 3H), 3.75 (t, J=4.8 Hz, 4H), 3.10 (t, J=4.8 Hz, 4H). m/z (ESI): 349 $(M+H)^+$.

Step 4: 2-(4-(3-Amino-6-chloropyridazin-4-yl)piperazin-1-yl)isonicotinic acid. To a solution of methyl 2-(4-(3-amino-6-chloropyridazin-4-yl)piperazin-1-yl)isonicotinate (0.20 g, 0.57 mmol) in THF (2 mL), water (2 mL) and MeOH (2 mL) was added LiOH monohydrate (72 mg, 1.72 mmol) and stirred at r.t. for 16 h. The reaction mixture was concentrated and neutralized with 1.5N HCl. The precipitated solids were filtered, washed with water and dried under vacuum to afford 2-(4-(3-amino-6-chloropyridazin-4-yl)piperazin-1-yl)isonicotinic acid (150 mg, 0.45 mmol, 78% yield) as off-white solid. $^1$H NMR (300 MHz, DMSO-$d_6$): δ ppm 13.43 (s, 1H), 8.29 (d, J=5.1 Hz, 1H), 7.27 (s, 1H), 7.04-7.12 (m, 1H), 6.95 (s, 1H), 6.25 (s, 2H), 3.74 (d, J=5.6 Hz, 4H), 3.08-3.12 (m, 4H). m/z (ESI): 333 $(M-H)^-$.

Step 5: 2-(4-(3-Amino-6-chloropyridazin-4-yl)piperazin-1-yl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)isonicotinamide. To a solution of 2-(4-(3-amino-6-chloropyridazin-4-yl)piperazin-1-yl)isonicotinic acid (0.15 g, 0.45 mmol) in DCM (3 mL) was added DIPEA (0.39 mL, 2.24 mmol) dropwise at 0° C. followed by HATU (0.26 g, 0.67 mmol) and stirred for 10 min. Then (2S,4R)-1-(S)-2-amino-3,3-dimethylbutanoyl)-4-hydroxy-N-(4-(4-methylthiazol-5-yl)benzyl)pyrrolidine-2-carboxamide hydrochloride (Intermediate 1, 0.31 g, 0.67 mmol) was added portion-wise at 0° C. and stirred at r.t. for 16 h. The reaction mixture was washed with water and brine, dried over anhydrous $Na_2SO_4$, concentrated under reduced pressure (rotary evaporator) and purified by column chromatography on silica gel eluting with 0-20% MeOH in DCM to afford 2-(4-(3-amino-6-chloropyridazin-4-yl)piperazin-1-yl)-N—((S)-1-((2S,4R)-4-hydroxy-2-((4-(4-(4-methylthiazol-5-yl)benzyl)carbamoyl)pyrrolidin-1-yl)-3,3-dimethyl-1-oxobutan-2-yl)isonicotinamide (0.30 g, 0.22 mmol, 49% yield) as orange solid. m/z (ESI): 748 $(M+H)^+$.

Step 6: 2-(4-(3-Amino-6-(2-hydroxyphenyl)pyridazin-4-yl)piperazin-1-yl)-N—((S)-1-((2S,4R)-4-hydroxy-2-((4-(4-methylthiazol-5-yl)benzyl)carbamoyl)pyrrolidin-1-yl)-3,3- dimethyl-1-oxobutan-2-yl)isonicotinamide (Example 1, 3390123). A mixture of 2-(4-(3-amino-6-chloropyridazin-4-yl)piperazin-1-yl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)isonicotinamide (0.30 g, 0.40 mmol), (2-hydroxyphenyl)boronic acid (66 mg, 0.48 mmol) and potassium carbonate (0.11 g, 0.80 mmol) in 1,4-dioxane (5.4 mL) and water (1.8 mL) was degassed with nitrogen for 5 min. Then X-Phos-Pd-G3 (16 mg, 0.020 mmol, Strem Chemicals) was added to the reaction mixture and it was stirred at 100° C. for 16 h. The reaction mixture was filtered through a celite pad and washed with EtOAc. The filtrate was washed with water, brine, dried over anhydrous $Na_2SO_4$, concentrated under reduced pressure (rotary evaporator) and purified by column chromatography on silica gel using 0-20% MeOH in DCM to provide 2-(4-(3-amino-6-(2-hydroxyphenyl)pyridazin-4-yl)piperazin-1-yl)-N—((S)-1-((2S,4R)-4-hydroxy-2-((4-(4-(4-methylthiazol-5-yl)benzyl)carbamoyl)pyrrolidin-1-yl)-3,3-dimethyl-1-oxobutan-2-yl)isonicotinamide (Example 1, 0.10 g, 0.12 mmol, 31% yield) as pale yellow solid. $^1H$ NMR (400 MHz, DMSO-$d_6$) δ 14.22 (s, 1H), 8.99 (s, 1H), 8.60 (t, J=6.1 Hz, 1H), 8.39 (d, J=9.1 Hz, 1H), 8.25 (d, J=5.2 Hz, 1H), 7.94 (d, J=7.9 Hz, 1H), 7.58 (s, 1H), 7.50-7.34 (m, 4H), 7.34-7.19 (m, 2H), 7.06 (d, J=5.2 Hz, 1H), 6.89 (dd, J=7.8, 6.3 Hz, 2H), 6.42 (s, 2H), 5.18 (d, J=3.5 Hz, 1H), 4.82 (d, J=9.1 Hz, 1H), 4.48-4.40 (m, 3H), 4.27 (d, J=5.5 Hz, 1H), 3.82-3.76 (m, 5H), 3.25-3.14 (m, 4H), 2.45 (s, 3H), 2.05 (d, J=8.2 Hz, 1H), 1.92 (d, J=6.6 Hz, 1H), 1.05 (s, 9H). m/z (ESI): 806.3 $(M+H)^+$.

(2S,4R)-1-(S)-2-Amino-3,3-dimethylbutanoyl)-4-hydroxy-N—((S)-1-(4-(4-methylthiazol-5-yl)phenyl)ethyl)pyrrolidine-2-carboxamide bis(hydrochloride) Salt (Intermediate 2)

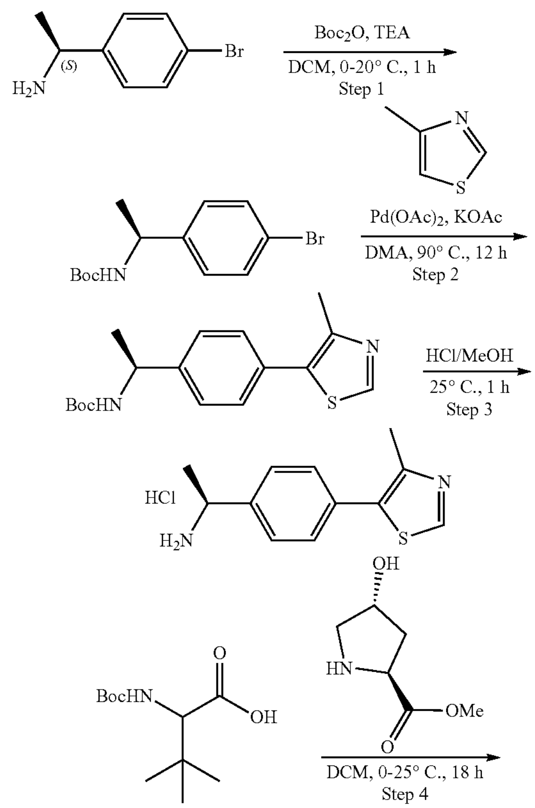

-continued

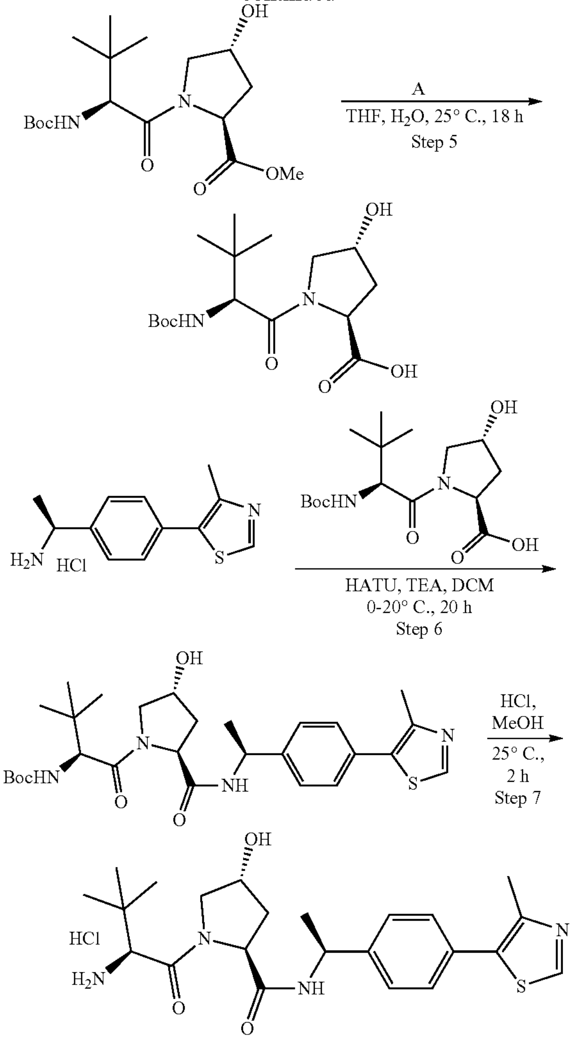

Intermediate 2

Step 1: tert-Butyl (S)-(1-(4-bromophenyl)ethyl)carbamate. To a solution of (S)-1-(4-bromophenyl)ethan-1-amine (50.0 g, 250 mmol) and $Et_3N$ (27.8 g, 275 mmol) in DCM (350 mL) was added $Boc_2O$ (57.3 g, 262 mmol) drop-wise at 0° C. and the mixture was stirred at 20° C. for 1 h. The mixture washed with water (2×150 mL), brine (150 mL), dried over $Na_2SO_4$, filtered and concentrated to give crude tert-butyl (S)-(1-(4-bromophenyl)ethyl)carbamate (65 g) as white solid. $^1H$ NMR (400 MHz, $CDCl_3$) δ ppm 7.46-7.43 (m, 2H), 7.19-7.16 (m, 2H), 4.74 (br s, 2H), 1.56 (s, 2H), 1.53 (s, 1H), 1.41 (s, 13H).

Step 2: tert-Butyl (S)-(1-(4-(4-methylthiazol-5-yl)phenyl)ethyl)carbamate. tert-Butyl (S)-(1-(4-bromophenyl)ethyl)carbamate (11.0 g, 36.6 mmol), 4-methylthiazole (7.27 g, 73.3 mmol), KOAc (7.19 g, 73.3 mmol) and $Pd(OAc)_2$ (82 mg, 366 μmol) in DMA (30 mL) was degassed and then heated to 90° C. for 12 h under nitrogen. The reaction mixture was diluted with water (80 mL) and extracted with DCM (3×80 mL). The combined organic layers were washed with brine (2×80 mL), dried over $Na_2SO_4$, filtered and concentrated under reduced pressure (rotary evaporator). The crude residue was purified by column chromatography on silica gel eluting with 30:1 to 3:1 petroleum ether/EtOAc to afford tert-butyl (S)-(1-(4-(4-methylthiazol-5-yl)phenyl)ethyl)carbamate (19.0 g, 59.7 mmol, 41% yield) as white solid.

Step 3: (S)-1-(4-(4-Methylthiazol-5-yl)phenyl)ethan-1-amine hydrochloride. A mixture of tert-butyl (S)-(1-(4-(4-methylthiazol-5-yl)phenyl)ethyl)carbamate (19.0 g, 56.7 mmol) and HCl/MeOH (4 M, 142 mL) in MeOH (140 mL) was stirred at 25° C. for 1 h. The mixture was concentrated under reduced pressure (rotary evaporator) to afford crude (S)-1-(4-(4-methylthiazol-5-yl)phenyl)ethan-1-amine hydrochloride (18.0 g) as white solid.

Step 4: Methyl (2S,4R)-1-(S)-2-((tert-butoxycarbonyl) amino)-3,3-dimethylbutanoyl)-4-hydroxypyrrolidine-2-carboxylate. To a solution of (S)-2-((tert-butoxycarbonyl) amino)-3,3-dimethylbutanoic acid (15.7 g, 86.5 mmol) and HATU (36.2 g, 95.1 mmol) in DCM (140 mL) was added methyl (2S,4R)-4-hydroxypyrrolidine-2-carboxylate (20.0 g, 86.5 mmol) and $Et_3N$ (30.6 g, 302 mmol) at 0° C. The mixture was stirred at 25° C. for 18 h then the reaction mixture was quenched with water (400 mL) at 25° C., and extracted with EtOAc (3×200 mL). The combined organic layers were washed with 5% citric acid (2×140 mL), sat'd $NaHCO_3$ solution (2×140 mL), and brine (2×140 mL) and dried over $Na_2SO_4$, filtered and concentrated under reduced pressure (rotary evaporator). The crude residue was purified by column chromatography on silica gel eluting with 30:1 to 3:1 petroleum ether/EtOAc to afford methyl (2S,4R)-1-((S)-2-((tert-butoxy carbonyl)amino)-3,3-dimethylbutanoyl)-4-hydroxypyrrolidine-2-carboxylate (24.0 g, 67.0 mmol, 77% yield) as white solid. $^1H$ NMR (400 MHz, $CDCl_3$) δ ppm 5.27 (d, J=9.2 Hz, 1H), 4.67 (t, J=8.4 Hz, 1H), 4.50 (br s, 1H), 4.18 (d, J=9.6 Hz, 1H), 4.11 (d, J=7.2 Hz, 1H), 3.76 (s, 4H), 3.0 (br s, 1H), 2.37-2.32 (m, 1H), 1.40 (s, 9H), 1.1 (s, 9H), 1.0 (s, 1H).

Step 5: (2S,4R)-1-((S)-2-((tert-Butoxycarbonyl)amino)-3,3-dimethylbutanoyl)-4-hydroxypyrrolidine-2-carboxylic acid. A mixture of methyl (2S,4R)-1-((S)-2-((tert-butoxycarbonyl)amino)-3,3-dimethylbutanoyl)-4-hydroxypyrrolidine-2-carboxylate (7.00 g, 19.53 mmol), LiOH monohydrate (2.34 g, 97.65 mmol) in THF (34 mL) and water (10 mL) was purged with nitrogen, and then the mixture was stirred at 25° C. for 18 h. The THF was removed under reduced pressure (rotary evaporator) and the residue was diluted with ice water (35 mL) and the pH was slowly adjusted to pH 2-3 with 3N HCl (ca. 20 mL). The resulting suspension was filtered and washed with water (2×30 mL) to give (2S,4R)-1-((S)-2-((tert-butoxy carbonyl)amino)-3,3-dimethylbutanoyl)-4-hydroxypyrrolidine-2-carboxylic acid (5.36 g, 15.6 mmol, 80% yield) as white solid.

Step 6: tert-Butyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate. A mixture of (S)-1-(4-(4-methylthiazol-5-yl)phenyl)ethan-1-amine hydrochloride (4.9 g, 19.2 mmol), (2S,4R)-1-((S)-2-((tert-butoxycarbonyl)amino)-3,3-dimethylbutanoyl)-4-hydroxypyrrolidine-2-carboxylic acid (7.4 g, 19.2 mmol), HATU (8.0 g, 21.2 mmol), $Et_3N$ (9.3 mL, 67.3 mmol) in DCM (100 mL) was purged with nitrogen, and then the mixture was stirred at 0-25° C. for 20 h. The reaction mixture was quenched with water (50 mL) and extracted with EtOAc (3×100 mL). The combined organic layers were washed with 5% citric acid (2×70 mL), sat'd $NaHCO_3$ solution (2×70 mL), and brine (2×70 mL) and dried over $Na_2SO_4$, filtered and concentrated under reduced pressure (rotary evaporator). The crude residue was purified by reverse phase column chromatography to afford tert-butyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate (5.9 g, 10.2 mmol, 53% yield) as white solid.

Step 7: (2S,4R)-1-((S)-2-Amino-3,3-dimethylbutanoyl)-4-hydroxy-N—((S)-1-(4-(4-methylthiazol-5-yl)phenyl) ethyl)pyrrolidine-2-carboxamide bis(hydrochloride) salt (Intermediate 2). A mixture of ((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl)carbamate (4.1 g, 7.5 mmol), HCl/MeOH (4 M, 18.8 mL) in MeOH (30 mL) was purged with nitrogen, and then the mixture was stirred at 25° C. for 2 h. The mixture was concentrated to give the crude product. The residue was purified by reverse phase column chromatography to afford (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide bis(hydrochloride) salt (Intermediate 2, 5.1 g, 9.8 mmol, 92% yield) as yellow solid. $^1H$ NMR (400 MHz, DMSO-$d_6$) δ ppm 9.16 (s, 1H), 8.65 (d, 1H), 8.17 (s, 3H), 7.48-7.44 (m, J=8.7, 3, 2H), 7.41-7.38 (m, 2H), 5.96 (br s, 1H), 4.91 (t, J=7.2, 1H), 4.54 (t, J=8.0 Hz, 1H), 4.30 (s, 1H), 3.74 (d, J=7.2, 1H), 3.50-3.46 (m, 1H), 2.47 (s, 3H), 2.11 (t, J=4.8 Hz, 1H), 1.77-1.72 (m, 1H), 2.35-2.38 (m, 1H), 1.37 (s, J=8.0 Hz, 3H), 1.02 (s, 9H).

6-(4-(3-Amino-6-(2-hydroxyphenyl)pyridazin-4-yl) piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)picolinamide (Example 2)

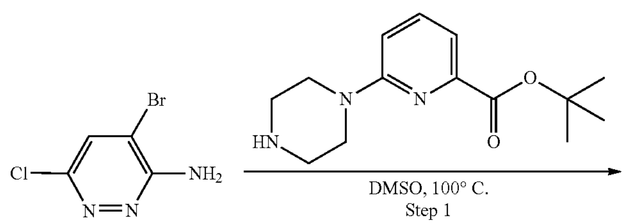

-continued

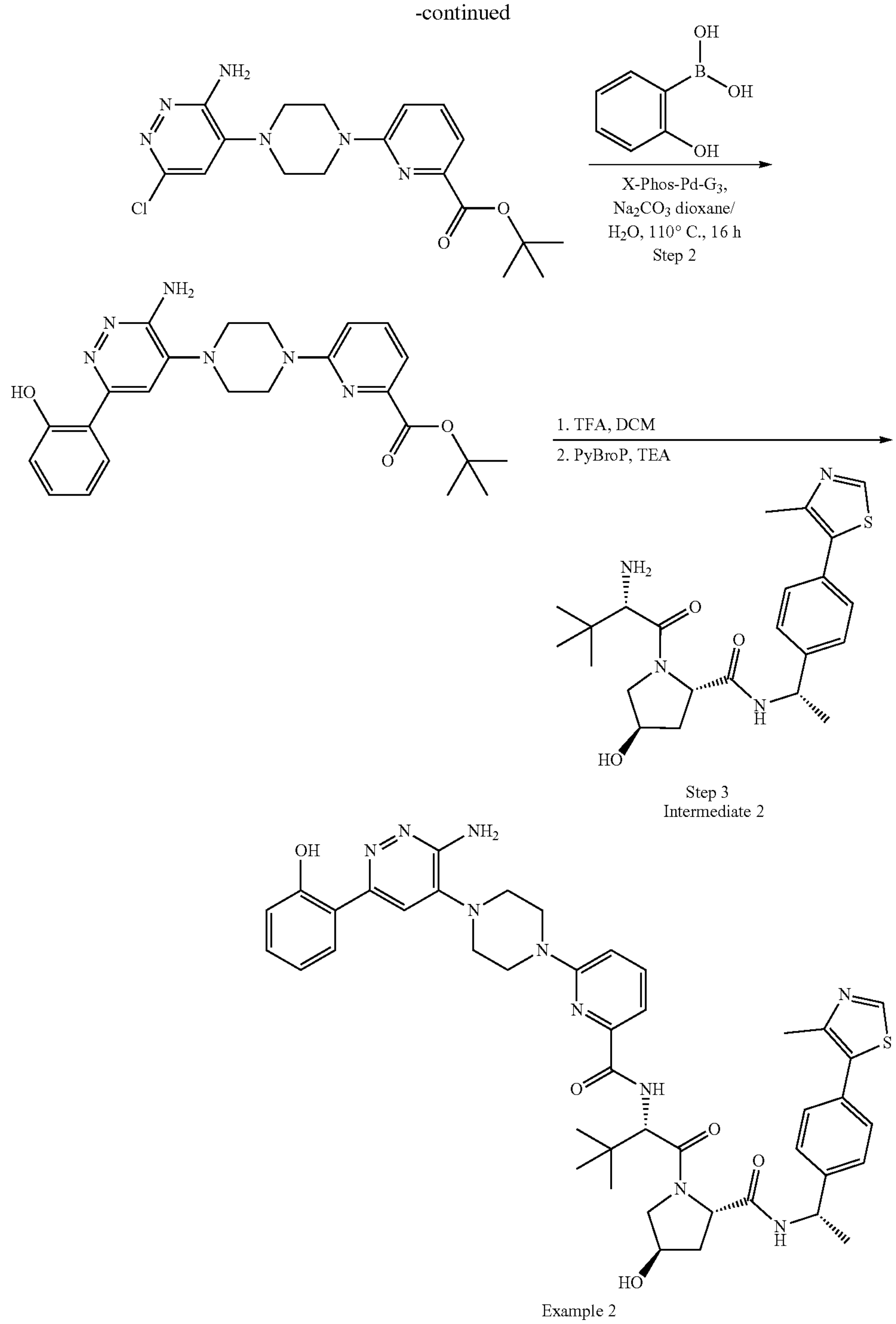

Intermediate 2

Example 2

Step 1: tert-Butyl 6-(4-(3-amino-6-chloropyridazin-4-yl) piperazin-1-yl)picolinate. To a solution of tert-butyl 6-(piperazin-1-yl)picolinate (2.00 g, 7.59 mmol, Aurum Pharmatech) in DMSO (25.3 mL) was added 3-amino-4-bromo-6-chloropyridazine (1.90 g, 9.11 mmol, Combi Blocks), followed by DIPEA (2.94 g, 22.78 mmol) dropwise. The reaction mixture was stirred at 100° C. for 18 h. The reaction mixture was diluted with water and extracted with ethyl acetate (100 mL). The aqueous layer was separated and back-extracted with EtOAc (3×). The organic layer was dried over $Na_2SO_4$ and concentrated and purified using column chromatography on silica gel eluting with 0-60% EtOH/EtOAc (3:1) in heptane to afford tert-butyl 6-(4-(3-amino-6-chloropyridazin-4-yl)piperazin-1-yl)picolinate (2.14 g, 5.47 mmol, 72% yield) as tan solid.

Step 2: tert-Butyl 6-(4-(3-amino-6-(2-hydroxyphenyl) pyridazin-4-yl)piperazin-1-yl)picolinate. A mixture of tert-butyl 6-(4-(3-amino-6-chloropyridazin-4-yl)piperazin-1-yl) picolinate (0.53 g, 1.36 mmol), 2-hydroxybenzeneboronic acid (0.28 g, 2.04 mmol, Oakwood Products, Inc.), (2-dicyclohexylphosphino-2',4',6'-triisopropyl-1,1'-biphenyl) [2-(2'-amino-1,1'-biphenyl)]palladium (II) methanesulfonate (0.12 g, 0.14 mmol, Sigma-Aldrich Corporation), and sodium carbonate (0.36 g, 3.40 mmol) in 1,4-dioxane (5 mL) and water (2 mL) was purged with argon, capped and heated to 110° C. for 2 h. The reaction mixture was diluted with water and extracted with EtOAc (2×). The combined organic layers was concentrated and the residue purified by column chromatography on silica gel eluting with 0-80% EtOH/EtOAc (3:1) in heptane to afford the title compound (0.47 g, 1.05 mmol, 77% yield). m/z (ESI, +ve ion): 449.2 $(M+H)^+$.

Step 3: 6-(4-(3-Amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)picolinamide (Example 2). TFA (1.4 mL, 18.5 mmol) was added to a solution of tert-butyl 6-(4-(3-amino-6-(2-hydroxyphenyl)pyridazin-4-yl)piperazin-1-yl)picolinate (0.17 g, 0.37 mmol) in DCM (2 mL). The reaction was stirred at r.t. for 2 h and concentrated to dryness under reduced pressure (rotary evaporator). The crude residue was treated with (2S,4R)-1-((S)-2-amino-3,3-dimethylbutanoyl)-4-hydroxy-N-((5)-1-(4-(4-methylthiazol-5-yl)phenyl)ethyl)pyrrolidine-2-carboxamide (Intermediate 2, 165 mg, 0.370 mmol), bromotri(1-pyrrolidinyl)phosphonium hexafluorophosphate (0.26 g, 0.56 mmol, Sigma-Aldrich Corporation), and TEA (0.26 mL, 1.85 mmol) in DCM (2 mL). The resulting solution was stirred at r.t. for 2 h, diluted with water and extracted with EtOAc (2×). The combined organic layers was concentrated under reduced pressure (rotary evaporator) and the crude residue was purified by column chromatography on silica gel, eluting with a gradient of 0-20% MeOH in DCM to afford 6-(4-(3-amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)picolinamide (Example 2, 29 mg, 0.035 mmol, 10% yield). $^1$H NMR (400 MHz, $CDCl_3$) δ 8.64 (s, 1H), 8.53 (br d, J=8.50 Hz, 1H), 7.48-7.70 (m, 4H), 7.27-7.39 (m, 6H), 7.05 (br d, J=8.09 Hz, 1H), 6.85-6.94 (m, 2H), 4.99-5.20 (m, 3H), 4.77 (br t, J=7.57 Hz, 1H), 4.68 (br d, J=8.50 Hz, 1H), 4.54 (br s, 1H), 4.24 (br d, J=11.20 Hz, 1H), 3.75 (br s, 4H), 3.67 (br d, J=10.78 Hz, 2H), 3.24 (br s, 4H), 2.98-3.13 (m, 1H), 2.49 (s, 4H), 1.99-2.14 (m, 1H), 1.48 (br d, J=6.84 Hz, 3H), 1.15 (s, 9H). m/z (ESI, +ve ion): 819.2 $(M+H)^+$.

2-(4-(3-Amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)isonicotinamide (Example 3)

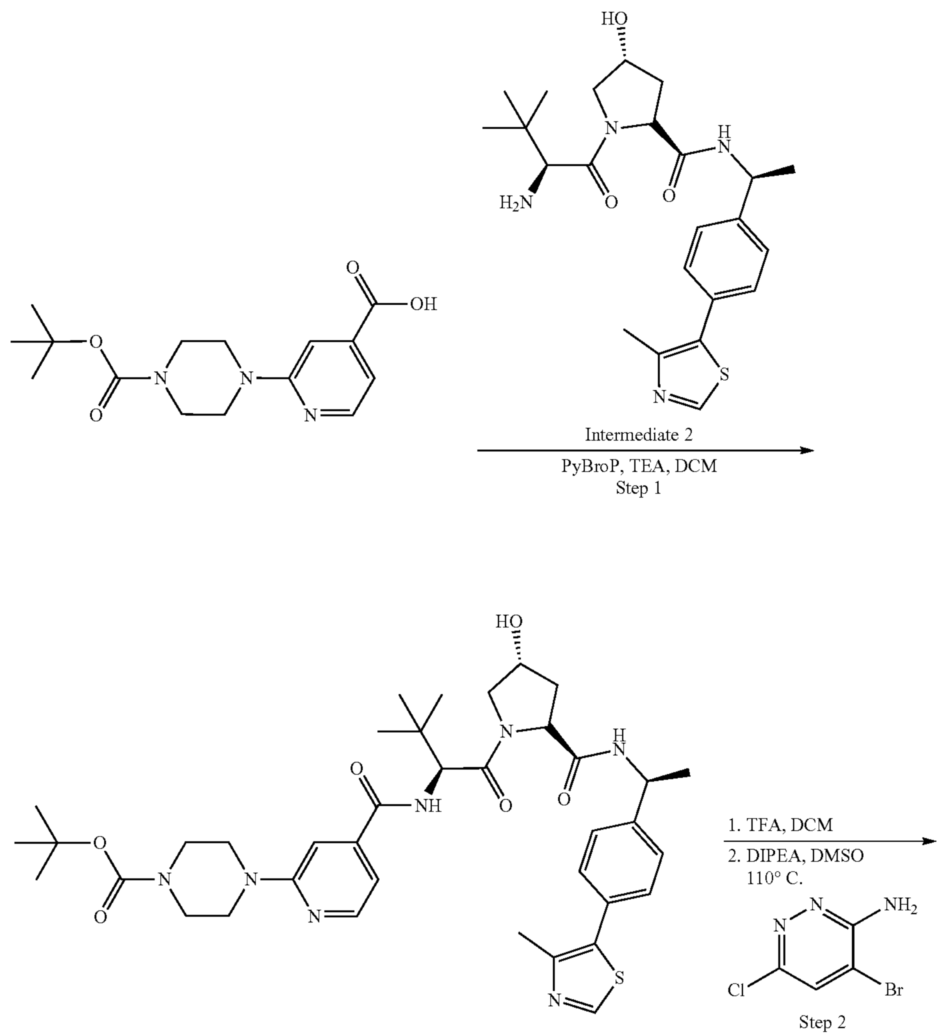

-continued

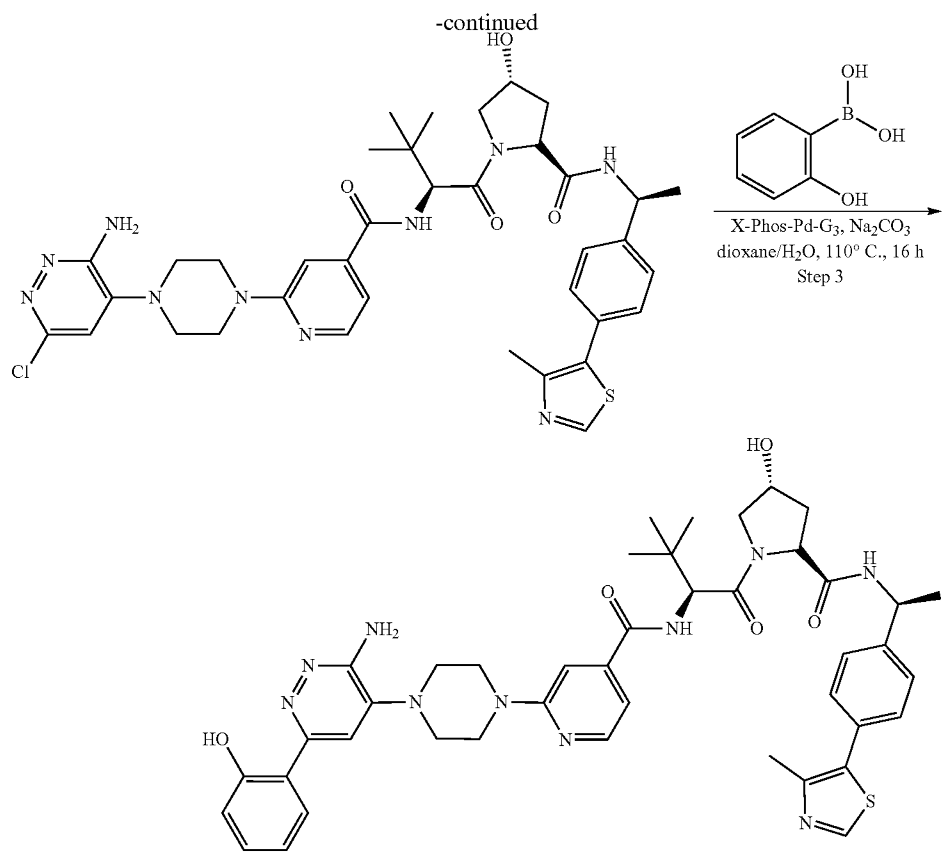

Example 3

Step 1: tert-Butyl 4-(4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamoyl)pyridin-2-yl)piperazine-1-carboxylate. A mixture of 2-(4-[(tert-butoxy)carbonyl]piperazin-1-yl)pyridine-4-carboxylic acid (1.73 g, 5.63 mmol, Enamine), (2S,4R)-1-((5)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 2, 2.71 g. 5.63 mmol), bromotri(pyrrolidin-1-yl)phosphonium hexafluorophosphate(V) (2.89 g, 6.19 mmol, Sigma-Aldrich Corporation), and $Et_3N$ (2.4 mL, 16.9 mmol) in DCM (20 mL) was stirred at r.t. for 2 h. The reaction mixture was diluted with water and extracted with DCM (2×). The organic layer was concentrated under reduced pressure (rotary evaporator) and the crude residue purified by column chromatography on silica gel eluting with 0-10% MeOH in DCM to afford the title compound (3.19 g, 4.35 mmol, 77% yield). m/z (ESI, +ve ion): 734.3 $(M+H)^+$.

Step 2: 2-(4-(3-Amino-6-chloropyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)isonicotinamide. TFA (7.54 mL, 97.80 mmol) was added to a solution of tert-butyl 4-(4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamoyl)pyridin-2-yl)piperazine-1-carboxylate (3.59 g, 4.89 mmol) in DCM (20 mL). The solution was stirred at r.t. for 2 h and concentrated under reduced pressure (rotary evaporator). The crude residue was dissolved in DMSO (10 mL) and treated with 3-amino-4-bromo-6-chloropyridazine (1.02 g, 4.89 mmol, Combi-Blocks) and DIPEA (8.54 mL, 48.9 mmol) and heated to 100° C. for 18 h. The reaction mixture was cooled, diluted with water and extracted with DCM (2×). The organic layer was concentrated under reduced pressure (rotary evaporator) and the crude residue purified by column chromatography on silica gel eluting with a gradient of 0-20% MeOH in DCM to afford the title compound (2.02 g, 2.65 mmol, 54% yield). m/z (ESI, +ve ion): 761.1/762.3 $(M+H)^+$.

Step 3: 2-(4-(3-Amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)isonicotinamide (Example 3). A mixture of 2-(4-(3-amino-6-chloropyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)isonicotinamide (1.60 g, 2.10 mmol), 2-hydroxybenzeneboronic acid (0.58 g, 4.20 mmol, Oakwood Products, Inc.), (2-dicyclohexylphosphino-2',4',6'-triisopropyl-1,1'-biphenyl)[2-(2'-amino-1,1'-biphenyl)]palladium (II) methanesulfonate (0.18 g, 0.21 mmol, Sigma-Aldrich Corporation), and sodium carbonate (0.67 g, 6.30 mmol) in 1,4-dioxane (15 mL) and water (10 mL) was heated to 110° C. for 1 h. The reaction mixture was diluted with water and extracted with DCM (3×). The organic layer was concentrated under reduced pressure (rotary evaporator) and the crude residue purified by column chromatography on silica gel eluting with a gradient of 0-20% MeOH in DCM. The product was further purified via preparative SFC using a Princeton MSA (250×21 mm, 5 mm) with a mobile phase of 65% liquid $CO_2$ and 35% MeOH using a flowrate of 70 mL/min to afford the title compound (Example 3, 0.70 g, 0.86 mmol, 41% yield). $^1$H NMR (DMSO-$d_6$, 400 MHz) δ 14.21 (br s, 1H), 8.99 (br s, 1H), 8.41 (br d, 1H, J=7.0 Hz), 8.2-8.4 (m, 2H), 7.94 (br d, 1H, J=6.8 Hz), 7.58 (br s, 1H), 7.3-7.5 (m, 4H), 7.2-7.3 (m, 2H), 7.0-7.1 (m, 1H), 6.90 (br d, 2H, J=6.8 Hz), 6.40 (br s, 2H), 5.1-5.2 (m, 1H), 4.9-5.0 (m, 1H), 4.80 (br d, 1H, J=9.1 Hz), 4.47 (br t, 1H, J=7.6 Hz), 4.33 (br s, 2H), 3.83 (br s, 4H), 3.68 (br s, 2H), 3.2-3.3 (m, 4H), 2.5-2.5 (m, 2H), 1.9-2.1 (m, 1H), 1.82 (br s, 1H), 1.39 (br d, 3H, J=6.4 Hz), 1.05 (br s, 9H). m/z (ESI, +ve ion): 819.3 $(M+H)^+$.

(2S,4R)-1-((S)-2-(3-(4-(3-Amino-6-(2-hydroxyphenyl)pyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide (Example 4)

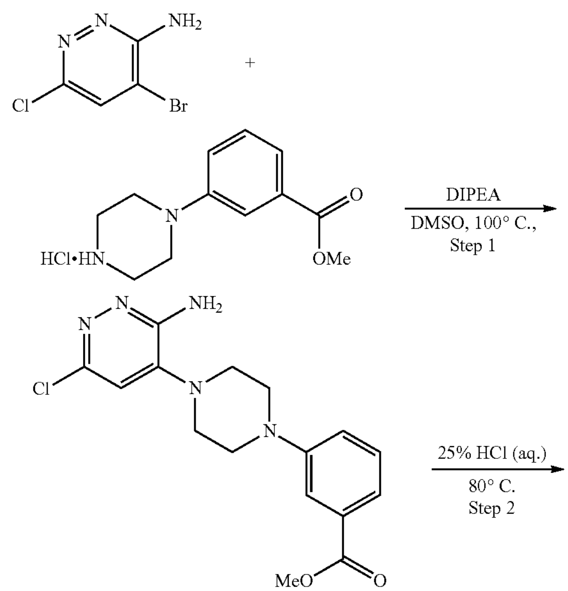

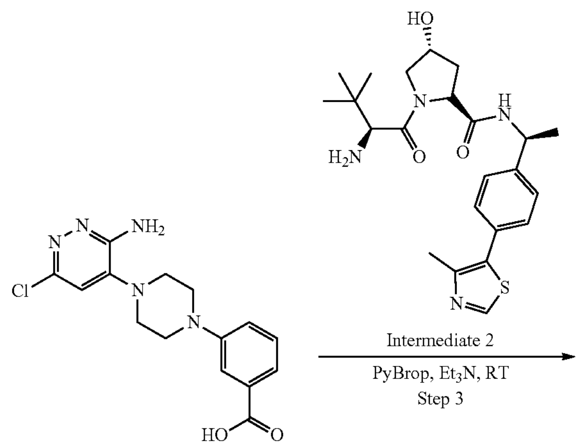

-continued

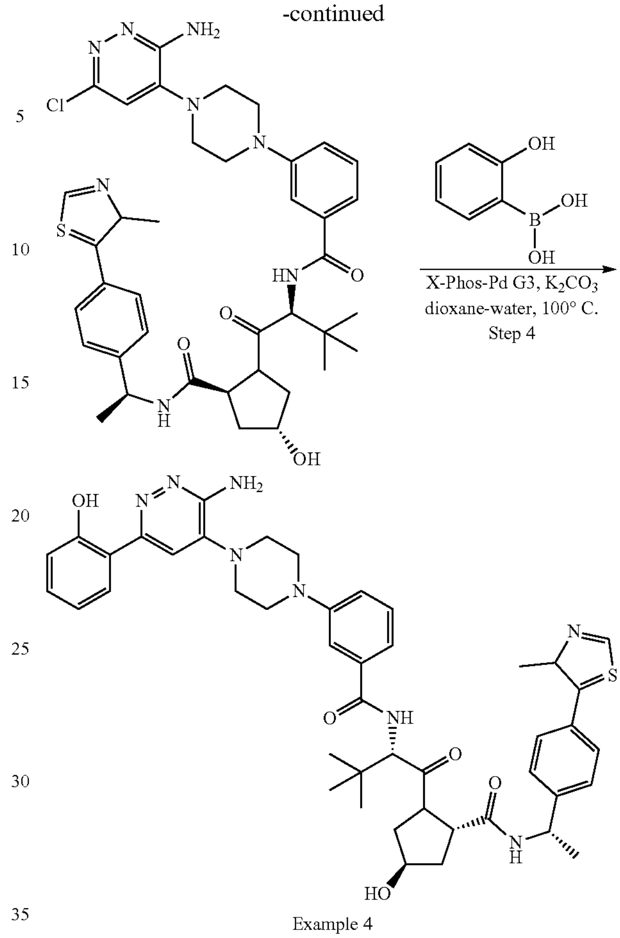

Example 4

Step 1: Methyl 3-(4-(3-amino-6-chloropyridazin-4-yl)piperazin-1-yl)benzoate. To a solution of methyl 3-(piperazin-1-yl)benzoate hydrochloride (2.04 g, 7.95 mmol, Zerenex) in DMSO (27 mL) was added 3-amino-4-bromo-6-chloropyridazine (1.99 g, 9.54 mmol, Combi Blocks Inc.), followed by DIPEA (5.6 mL, 31.8 mmol) dropwise. The reaction mixture was stirred at 100° C. for 18 h. After cooling to r.t., the reaction mixture was diluted with water and extracted with EtOAc (100 mL). The aqueous layer was separated and back-extracted with EtOAc (3×). The combined organic layer was dried over sodium sulfate and concentrated under reduced pressure (rotary evaporator) and the crude product was purified by column chromatography on silica gel using a gradient of 0-60% EtOAc/EtOH (3:1) in heptane to afford methyl 3-(4-(3-amino-6-chloropyridazin-4-yl)piperazin-1-yl)benzoate (1.4 g, 4.0 mmol, 51% yield) as yellow solid. $^1$H NMR (400 MHz, $CDCl_3$) δ ppm 7.64 (s, 1H), 7.59 (d, J=7.67 Hz, 1H), 7.36 (t, J=7.98 Hz, 1H), 7.16 (dd, J=8.19, 1.97 Hz, 1H), 6.81 (s, 1H), 4.82 (br s, 2H), 3.92 (s, 3H), 3.36-3.43 (m, 4H), 3.21-3.28 (m, 4H). m/z (ESI, +ve ion): 348.2 $(M+H)^+$.

Step 2: 3-(4-(3-Amino-6-chloropyridazin-4-yl)piperazin-1-yl)benzoic acid. The suspension of methyl 3-(4-(3-amino-6-chloropyridazin-4-yl)piperazin-1-yl)benzoate (0.7 g, 2.0 mmol) in 25% hydrochloric acid (2.4 mL, 20 mmol) was stirred at 80° C. for 18 h. After cooling to r.t., the reaction mixture was neutralized with 5 N NaOH to pH 6-7. The resulting precipitate was collected by filtration, washed with water, dried in a vacuum oven at 60° C. to afford 3-(4-(3-amino-6-chloropyridazin-4-yl)piperazin-1-yl)benzoic acid (0.68 g, 2.00 mmol, 100% yield) as tan solid. $^1$H NMR (400 MHz, DMSO-$d_6$) δ ppm 7.51 (br s, 2H), 7.33-7.44 (m, 2H), 7.27 (br d, J=7.05 Hz, 1H), 7.20 (s, 1H), 3.36-3.44 (m, 4H), 3.24 (br s, 4H). m/z (ESI, +ve ion): 334.1 $(M+H)^+$.

Step 3: (2S,4R)-1-((S)-2-(3-(4-(3-Amino-6-chloropyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide. A mixture of 3-(4-(3-amino-6-chloropyridazin-4-yl)piperazin-1-yl)benzoic acid (0.20 g, 0.60 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (Intermediate 2, 0.67 g, 1.50 mmol), triethylamine (0.25 mL, 1.8 mmol), and bromotri(1-pyrrolidinyl)phosphonium hexafluorophosphate (0.31 g, 0.66 mmol, Sigma-Aldrich Corporation) in DCM (4 mL) was stirred at r.t. for 16 h. The reaction mixture was warmed to 40° C. and stirred for another 36 h. After cooling to r.t., the reaction mixture was diluted with brine and extracted with EtOAc (3×). The organic layers were combined, dried ($MgSO_4$) and concentrated under reduced pressure (rotary evaporator). The crude residue was purified by column chromatography on silica gel, eluting with a gradient of 0-90% EtOAc/EtOH (3:1) in heptane, to provide 2-(4-(3-amino-(2S,4R)-1-((S)-2-(3-(4-(3-amino-6-chloropyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide (0.14 g, 0.19 mmol, 32% yield) as off-white solid. $^1$H NMR (400 MHz, $CDCl_3$) δ ppm 8.67 (s, 1H), 7.30-7.45 (m, 8H), 7.19 (d, J=7.46 Hz, 1H), 7.10 (dd, J=8.29, 2.07 Hz, 1H), 6.77-6.83 (m, 1H), 5.09 (quin, J=7.15 Hz, 1H), 4.87 (br s, 2H), 4.71-4.79 (m, 2H), 4.57 (br s, 1H), 4.19 (br d, J=11.40 Hz, 1H), 3.67 (dd, J=11.30, 3.63 Hz, 1H), 3.19-3.25 (m, 8H), 2.52 (s, 3H), 1.49 (d, J=7.05 Hz, 3H), 1.39 (t, J=7.36 Hz, 2H), 1.13 (s, 9H). m/z (ESI, +ve ion): 760.3 $(M+H)^+$.

Step 4: (2S,4R)-1-((S)-2-(3-(4-(3-Amino-6-(2-hydroxyphenyl)pyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide (Example 4). A mixture of (2S,4R)-1-((S)-2-(3-(4-(3-amino-6-chloropyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide (0.14 g, 0.19 mmol), 2-hydroxybenzeneboronic acid (52 mg, 0.38 mmol, Oakwood Products, Inc.), X-Phos Pd G3 (16 mg, 0.019 mmol, Sigma-Aldrich Corporation) and potassium carbonate (65 mg, 0.47 mmol) were flushed with nitrogen and treated with 1,4-dioxane (710 μL) and water (240 μL). The reaction mixture was heated at 100° C. for 20 h. After cooling to r.t., the reaction mixture was partitioned between EtOAc and brine. The aqueous layer was back-extracted with EtOAc (3×) and the combined organic layers was dried ($MgSO_4$) and concentrated under reduced pressure (rotary evaporator). The crude residue was purified by column chromatography on silica gel eluting with a gradient of 0-100% EtOAc/EtOH (3:1) in heptane, to provide (2S,4R)-1-((S)-2-(3-(4-(3-amino-6-(2-hydroxyphenyl)pyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide (Example 4, 37 mg, 0.045 mmol, 24% yield) as off-white solid. $^1$H NMR (400 MHz, $CDCl_3$) δ ppm 8.61 (s, 1H), 8.10 (s, 1H), 7.41-7.54 (m, 2H), 7.32-7.38 (m, 6H), 7.24-7.32 (m, 3H), 6.82 (br d, J=8.09 Hz, 1H), 5.28-5.38 (m, 1H), 4.64 (t, J=8.60 Hz, 1H), 4.58 (dd, J=8.81, 4.66 Hz, 1H), 4.46 (d, J=8.71 Hz, 1H), 4.35-4.43 (m, 3H), 4.02-4.10 (m, 2H), 4.01-4.04 (m, 1H), 3.60-3.72 (m, 3H), 3.56 (dd, J=15.45, 9.23 Hz, 1H), 3.20-3.33 (m, 2H), 3.11-3.20 (m, 1H), 2.47 (s, 3H), 1.63 (s, 3H), 1.18-1.23 (m, 2H), 0.98 (s, 9H). m/z (ESI, +ve ion): 818.3 $(M+H)^+$.

2-(4-(3-Amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)thiazole-4-carboxamide (Example 5)

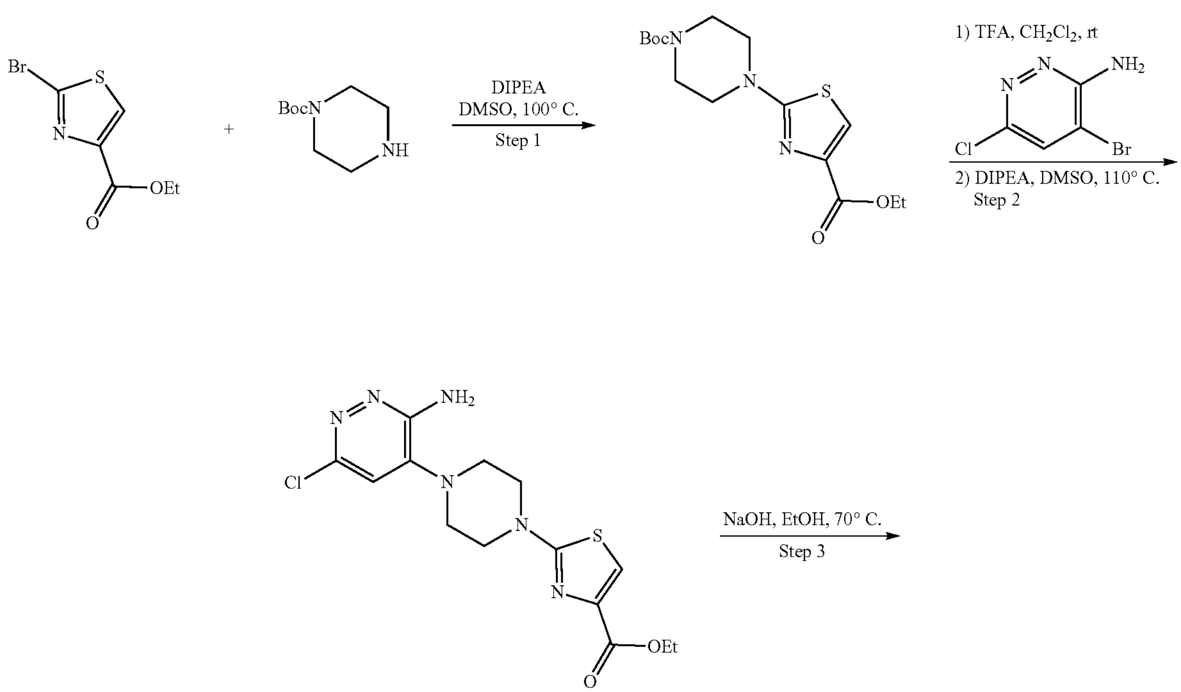

-continued

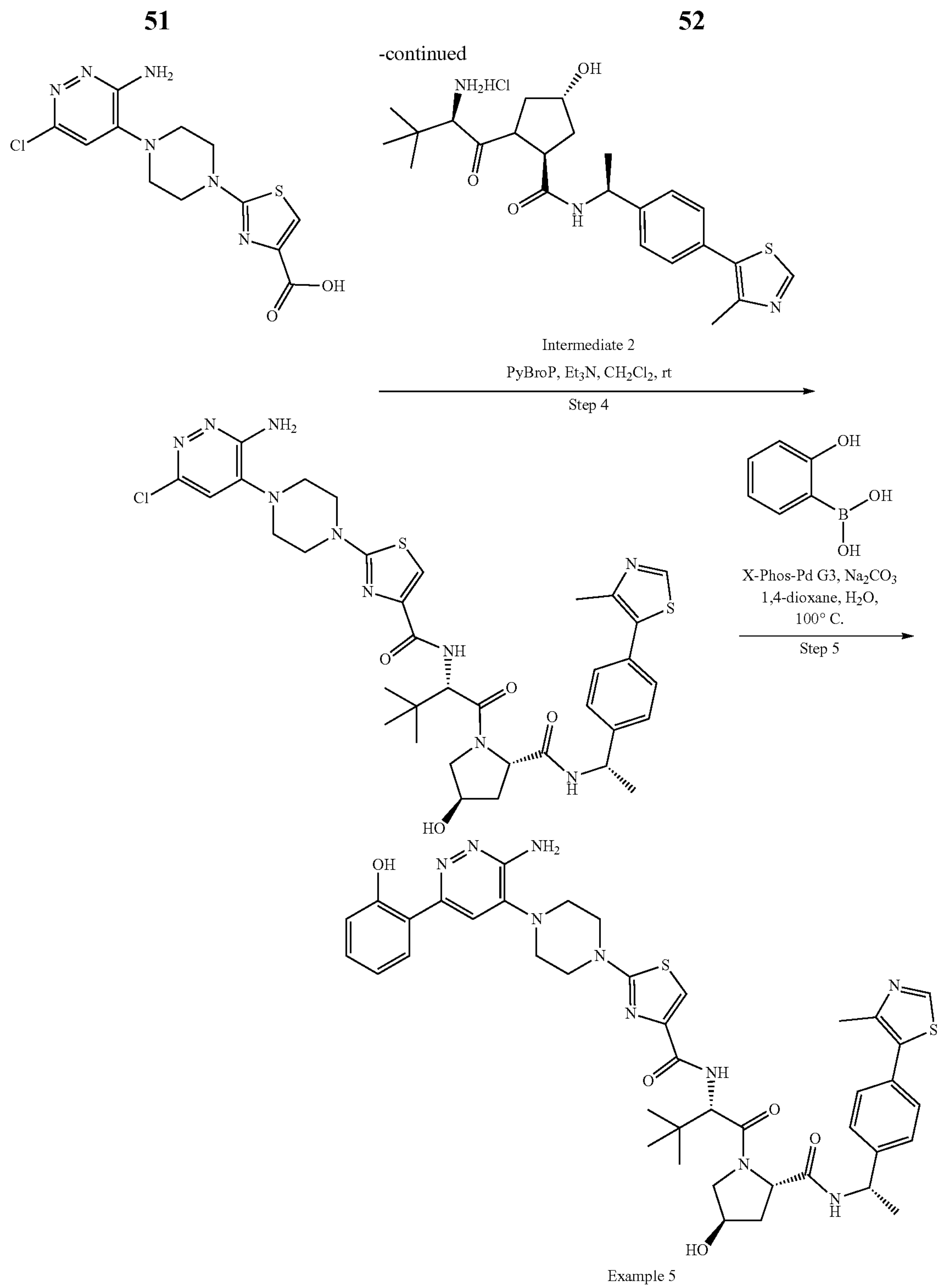

Example 5

Step 1: Ethyl 2-(4-(tert-butoxycarbonyl)piperazin-1-yl) thiazole-4-carboxylate. To a solution of 1-(tert-butoxycarbonyl)-piperazine (1.41 g, 7.57 mmol) and ethyl 2-bromothiazole-4-carboxylate (2.14 g, 9.08 mmol) in DMSO (5 mL) was added DIPEA (2.6 mL, 15.1 mmol). The resulting mixture was stirred at 100° C. for 16 h, cooled to r.t. then the reaction mixture was diluted with DCM and washed with $H_2O$. The organic layer was concentrated under reduced pressure (rotary evaporator) and purified by column chromatography on silica gel, eluting with a gradient of 0-40% EtOAc/heptane to afford the title compound (2.07 g, 80% yield) as yellow solid. $^1H$ NMR (400 MHz, $CDCl_3$) δ ppm 7.43-7.49 (m, 1H), 4.32-4.40 (m, 2H), 3.48-3.60 (m, 8H), 1.48 (s, 9H), 1.34-1.41 (m, 3H). m/z (ESI, +ve ion): 342 $(M+H)^+$.

Step 2: Ethyl 2-(4-(3-amino-6-chloropyridazin-4-yl)piperazin-1-yl)thiazole-4-carboxylate. Ethyl 2-(4-(tert-butoxycarbonyl)piperazin-1-yl)thiazole-4-carboxylate (2.07 g, 6.06 mmol) in DCM (10 mL) was treated with TFA (5.0 mL, 67.1 mmol) and stirred at r.t. for 2 h. The reaction mixture was concentrated to dryness under reduced pressure (rotary evaporator), then dissolved in DMSO (10 mL) and treated with DIPEA (5.29 mL, 30.3 mmol) at 0° C., followed by 3-amino-4-bromo-6-chloropyridazine (1.52 g, 7.28 mmol). The resulting mixture was heated at 110° C. for 16 h, cooled to r.t., then the reaction mixture was diluted with DCM and washed with $H_2O$ and the organic layer was dried over $MgSO_4$, filtered and concentrated under reduced pressure (rotary evaporator). The crude residue was purified by column chromatography on silica gel, eluting with a gradient of 0-10% MeOH in DCM to afford the title compound (1.08 g, 48% yield) as orange solid. m/z (ESI, +ve ion): 369 $(M+H)^+$.

Step 3: 2-(4-(3-Amino-6-chloropyridazin-4-yl)piperazin-1-yl)thiazole-4-carboxylic acid. To a stirred suspension of ethyl 2-(4-(3-amino-6-chloropyridazin-4-yl)piperazin-1-yl) thiazole-4-carboxylate (0.56 g, 1.52 mmol) in EtOH (15 mL) was added 5N sodium hydroxide solution (2 mL, 107 mmol) in water (2 mL). The resulting mixture was stirred at 70° C. for 1 h then the reaction mixture was concentrated under reduced pressure (rotary evaporator), the residue was dissolved in $H_2O$ and neutralized with aqueous HCl. The precipitate was collected by filtration and washed with heptane to afford the title compound (0.47 g, 91% yield) as yellow solid. $^1H$ NMR (400 MHz, DMSO-$d_6$) δ ppm 7.59-7.76 (m, 1H), 6.97 (s, 1H), 6.26 (s, 2H), 3.58-3.68 (m, 4H), 3.08-3.16 (m, 4H). m/z (ESI, +ve ion): 341 $(M+H)^+$.

Step 4: 2-(4-(3-Amino-6-chloropyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)thiazole-4-carboxamide. A mixture of 2-(4-(3-amino-6-chloropyridazin-4-yl)piperazin-1-yl)thiazole-4-carboxylic acid (40 mg, 0.12 mmol), (2S, 4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 2, 57 mg, 0.12 mmol), bromotripyrrolidinophosphonium hexafluorophosphate (0.11 g, 0.24 mmol), and $Et_3N$ (62 μL, 0.44 mmol) in DCM (2 mL) was stirred at r.t. for 2 h. The reaction mixture was purified by column chromatography on silica gel, eluting with a gradient of 0-10% MeOH in DCM to afford the title compound (Example 5, 65 mg, 72% yield) as yellow solid. $^1H$ NMR (400 MHz, $CDCl_3$) δ ppm 8.59 (s, 1H), 7.73 (d, J=8.9 Hz, 1H), 7.43 (d, J=7.7 Hz, 1H), 7.28-7.36 (m, 4H), 6.71 (s, 1H), 5.01 (t, J=7.3 Hz, 1H), 4.94 (s, 2H), 4.68 (t, J=7.8 Hz, 1H), 4.60 (d, J=8.9 Hz, 1H), 4.47 (br s, 1H), 4.08 (br d, J=11.4 Hz, 1H), 3.57-3.60 (m, 4H), 3.33-3.38 (m, 1H), 3.12 (br s, 4H), 2.30-2.62 (m, 5H), 1.41 (d, J=7.0 Hz, 3H), 1.04 (s, 9H). m/z (ESI, +ve ion): 767 $(M+H)^+$.

Step 5: 2-(4-(3-Amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)thiazole-4-carboxamide (Example 5). 2-(4-(3-Amino-6-chloropyridazin-4-yl)piperazin-1-yl)-N—((S)-1-((2S,4R)-4-hydroxy-2-(((S)-1-(4-(4-methylthiazol-5-yl)phenyl)ethyl) carbamoyl)pyrrolidin-1-yl)-3,3-dimethyl-1-oxobutan-2-yl) thiazole-4-carboxamide (65 mg, 0.085 mmol), 2-hydroxyphenylboronic acid (35 mg, 0.25 mmol), X-Phos Pd G3 (7.2 mg, 8.47 μmol) and sodium carbonate (22 mg, 0.21 mmol) were flushed with nitrogen and treated with 1,4-dioxane (2 mL) and water (1 mL). The reaction mixture was heated at 100° C. for 2 h and concentrated under reduced pressure (rotary evaporator). The crude residue was purified by column chromatography on silica gel, eluting with a gradient of 0-10% MeOH in DCM to afford the title compound (Example 5, 22 mg, 32% yield) as off-white solid. $^1H$ NMR (400 MHz, $CDCl_3$) δ ppm 8.65 (s, 1H), 7.80 (br d, J=8.9 Hz, 1H), 7.58 (br d, J=7.5 Hz, 1H), 7.46-7.52 (m, 1H), 7.42-7.45 (m, 1H), 7.26-7.40 (m, 7H), 6.91 (br t, J=7.5 Hz, 1H), 5.00-5.16 (m, 1H), 4.87-5.00 (m, 1H), 4.76 (br t, J=7.8 Hz, 1H), 4.66 (br d, J=8.7 Hz, 1H), 4.54 (br s, 1H), 4.21 (br d, J=11.0 Hz, 1H), 3.57-3.79 (m, 5H), 3.12-3.35 (m, 4H), 2.45-2.58 (m, 4H), 2.01-2.12 (m, 1H), 1.45-1.52 (m, 4H), 1.06-1.18 (m, 9H). m/z (ESI, +ve ion): 825.2 $(M+H)^+$.

(2S,4R)-1-((S)-2-(5-(4-(3-Amino-6-(2-hydroxyphenyl)pyridazin-4-yl)piperazin-1-yl)thiophene-2-carboxamido)-3,3-dimethylbutanoyl)-4-hydroxy-N—((S)-1-(4-(4-methylthiazol-5-yl)phenyl)ethyl) pyrrolidine-2-carboxamide (Example 6)

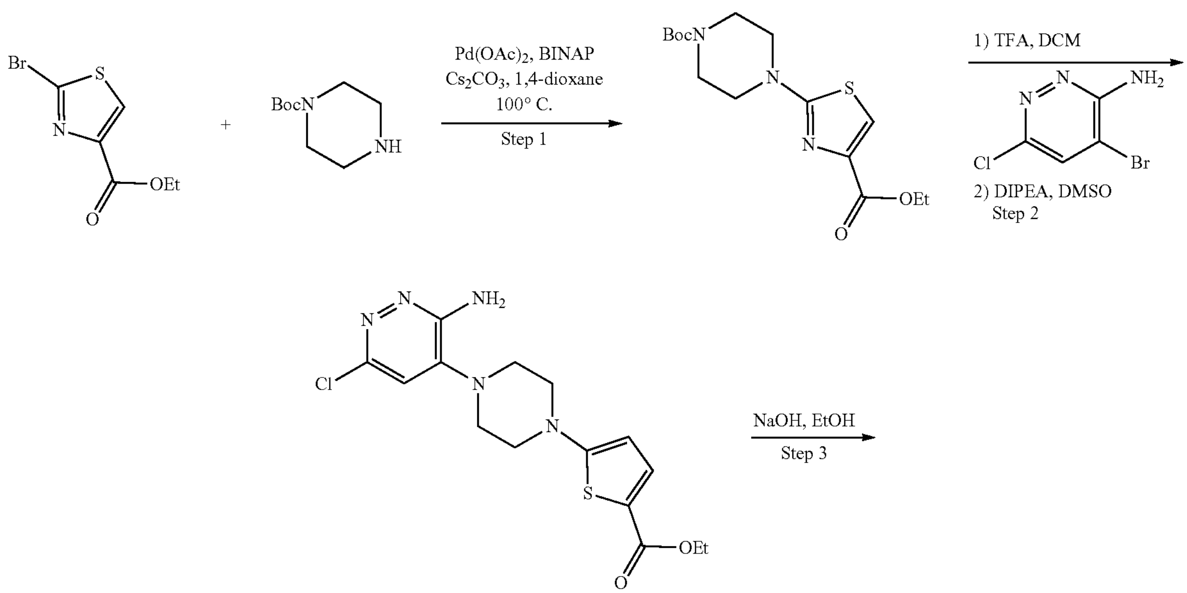

-continued

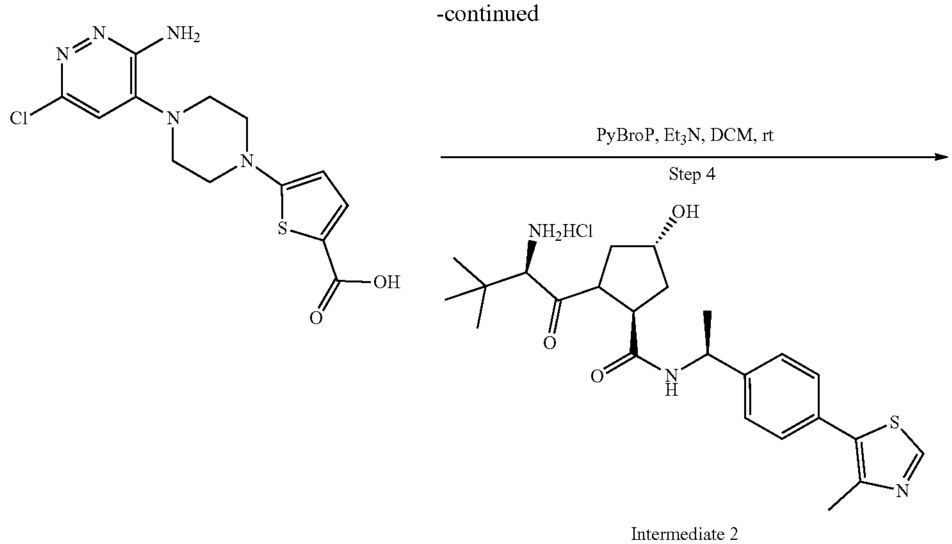

Intermediate 2

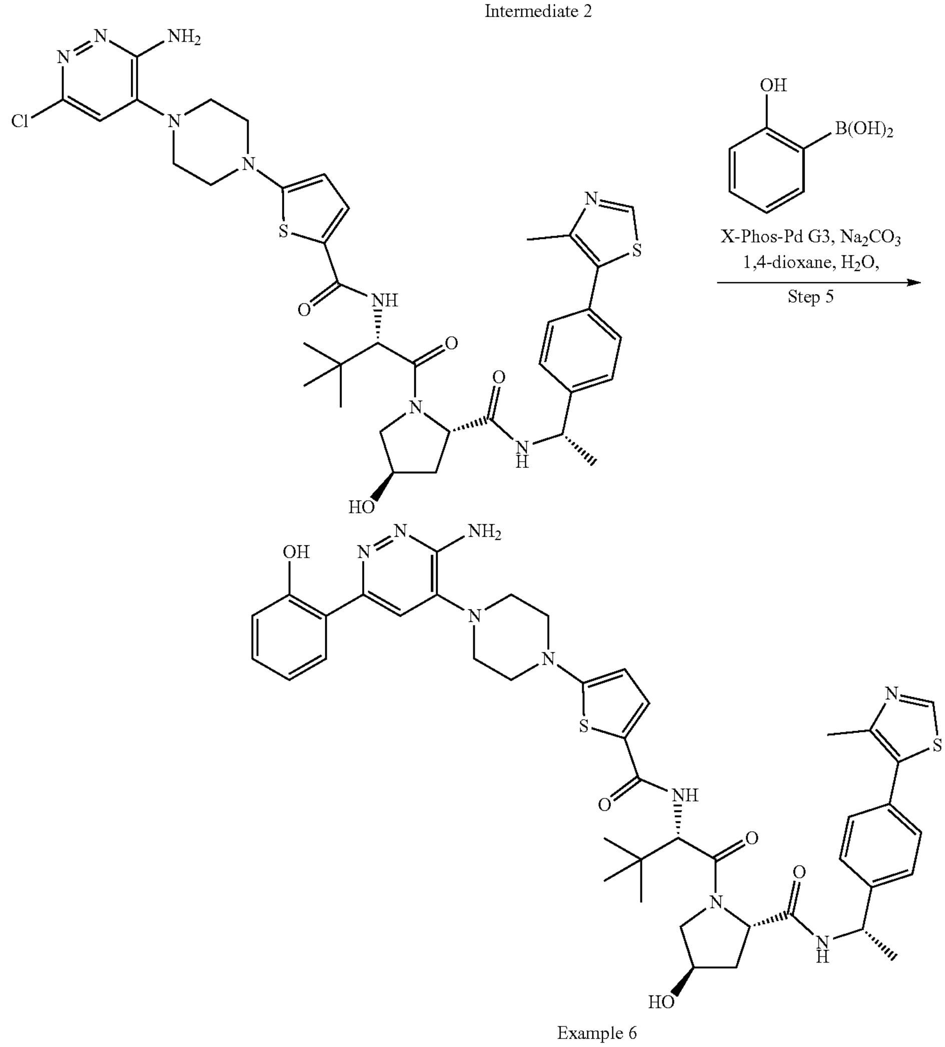

Example 6

Step 1: tert-Butyl 4-(5-(ethoxycarbonyl)thiophen-2-yl) piperazine-1-carboxylate. A mixture of ethyl 5-bromothiophene-2-carboxylate (1.00 g, 4.25 mmol), 1-(tert-butoxycarbonyl)-piperazine (0.79 g, 4.25 mmol), palladium (II) acetate (0.19 g, 0.85 mmol), rac-2,2-bis(diphenylphosphino)-1,1-binaphthyl (0.53 g, 0.85 mmol), and cesium carbonate (2.08 g, 6.38 mmol) was stirred in 1,4-dioxane (20 mL) at 100° C. for 16 h. The reaction mixture was filtered through celite and washed with EtOAc. The filtrate was concentrated under reduced pressure (rotary evaporator) and purified by column chromatography on silica gel, eluting with a gradient of 0-40% EtOAc in heptane to afford the title compound (0.56 g, 1.63 mmol, 38% yield) as yellow solid. $^1$H NMR (400 MHz, $CDCl_3$) δ ppm 7.52 (d, J=4.4 Hz, 1H), 6.02 (d, J=4.4 Hz, 1H), 4.26 (q, J=7.2 Hz, 2H), 3.51-3.59 (m, 4H), 3.15-3.23 (m, 4H), 1.45 (s, 9H), 1.31 (t, J=7.0 Hz, 3H). m/z (ESI, +ve ion): 341 $(M+H)^+$.

Step 2: Ethyl 5-(4-(3-amino-6-chloropyridazin-4-yl)piperazin-1-yl)thiophene-2-carboxylate. tert-Butyl 4-(5-(ethoxycarbonyl)thiophen-2-yl)piperazine-1-carboxylate (0.61 g, 1.79 mmol) in DCM (10 mL) was treated with TFA (2 mL, 26.8 mmol) and stirred at r.t. for 2 h. The reaction mixture was concentrated to dryness under reduced pressure (rotary evaporator), dissolved in DMSO (10 mL) and treated with DIPEA (1.56 mL, 8.96 mmol) at 0° C., followed by 3-amino-4-bromo-6-chloropyridazine (0.45 g, 2.15 mmol). The resulting mixture was heated at 110° C. for 16 h then the reaction mixture was diluted with DCM and washed with $H_2O$. The organic layer was dried over $MgSO_4$, filtered and concentrated under reduced pressure (rotary evaporator) and the crude residue was purified by column chromatography on silica gel, eluting with a gradient of 0-10% MeOH in DCM to afford the title compound (0.38 g, 1.03 mmol, 57% yield) as orange solid. m/z (ESI, +ve ion): 368 $(M+H)^+$.

Step 3: 5-(4-(3-Amino-6-chloropyridazin-4-yl)piperazin-1-yl)thiophene-2-carboxylic acid. To a stirred suspension of ethyl 5-(4-(3-amino-6-chloropyridazin-4-yl)piperazin-1-yl) thiophene-2-carboxylate (88 mg, 0.24 mmol) in EtOH (5 mL) was added 5N sodium hydroxide solution (1.0 mL, 53.3 mmol) in water (2 mL). The resulting mixture was stirred at 70° C. for 2 h. After concentration of the reaction mixture, the residue was dissolved in $H_2O$, neutralized with 1N HCl. The resulting precipitate was collected by filtration and washed with heptane to afford the title compound as orange solid (68 mg, 0.24 mmol, 100%) which was used directly in the subsequent step. m/z (ESI, +ve ion): 340 $(M+H)^+$.

Step 4: (2S,4R)-1-((S)-2-(5-(4-(3-Amino-6-chloropyridazin-4-yl)piperazin-1-yl)thiophene-2-carboxamido)-3,3-dimethylbutanoyl)-4-hydroxy-N—((S)-1-(4-(4-methylthiazol-5-yl)phenyl)ethyl)pyrrolidine-2-carboxamide. A mixture of 5-(4-(3-amino-6-chloropyridazin-4-yl)piperazin-1-yl)thiophene-2-carboxylic acid (34 mg, 0.10 mmol), (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 2, 48 mg, 0.10 mmol), bromotripyrrolidinophosphonium hexafluorophosphate (93 mg, 0.20 mmol), and $Et_3N$ (60 μL, 0.44 mmol) in DCM (2 mL) was stirred at r.t. for 2 h. The reaction mixture was purified by column chromatography on silica gel, eluting with a gradient of 0-10% MeOH in DCM to afford the title compound (33 mg, 0.043 mmol, 43% yield) as white solid. $^1$H NMR (400 MHz, $CDCl_3$) δ ppm 8.67 (s, 1H), 7.44-7.51 (m, 1H), 7.34-7.42 (m, 4H), 6.78 (s, 1H), 6.40 (d, J=8.5 Hz, 1H), 6.08 (d, J=4.1 Hz, 1H), 5.09 (t, J=7.3 Hz, 1H), 4.84 (s, 2H), 4.64-4.80 (m, 2H), 4.54 (br s, 1H), 4.16 (br d, J=11.4 Hz, 1H), 3.63 (dd, J=11.4, 3.3 Hz, 1H), 3.33-3.41 (m, 4H), 3.18-3.22 (m, 4H), 2.53 (s, 3H), 2.13-2.20 (m, 1H), 2.06 (br dd, J=13.3, 7.9 Hz, 1H), 1.49 (d, J=7.0 Hz, 3H), 1.10 (s, 9H). m/z (ESI, +ve ion): 766 $(M+H)^+$.

Step 5: (2S,4R)-1-((S)-2-(5-(4-(3-Amino-6-(2-hydroxyphenyl)pyridazin-4-yl)piperazin-1-yl)thiophene-2-carboxamido)-3,3-dimethylbutanoyl)-4-hydroxy-N—((S)-1-(4-(4-methylthiazol-5-yl)phenyl)ethyl)pyrrolidine-2-carboxamide (Example 6). (2S,4R)-1-((S)-2-(5-(4-(3-Amino-6-chloropyridazin-4-yl)piperazin-1-yl)thiophene-2-carboxamido)-3,3-dimethylbutanoyl)-4-hydroxy-N—((S)-1-(4-(4-methylthiazol-5-yl)phenyl)ethyl)pyrrolidine-2-carboxamide (33 mg, 0.043 mmol), 2-hydroxyphenylboronic acid (18 mg, 0.13 mmol), X-Phos Pd G3 (3.6 mg, 4.3 μmol), and sodium carbonate (11 mg, 0.11 mmol) were flushed with nitrogen and treated with 1,4-dioxane (2 mL) and water (1 mL) and the reaction mixture was heated at 100° C. for 2 h. The reaction mixture was concentrated under reduced pressure (rotary evaporator) and the crude residue was purified by column chromatography on silica gel, eluting with a gradient of 0-10% MeOH in DCM to afford the title compound (Example 6, 3.3 mg, 4.0 μmol, 9.3% yield) as white solid. $^1$H NMR (400 MHz, $CDCl_3$) δ ppm 8.64-8.70 (m, 1H), 7.50-7.64 (m, 2H), 7.32-7.44 (m, 7H), 7.30-7.32 (m, 1H), 7.07 (br d, J=8.9 Hz, 1H), 6.90-6.96 (m, 1H), 6.38-6.45 (m, 1H), 6.05-6.12 (m, 1H). 5.05-5.14 (m, 1H), 4.63-4.80 (m, 2H), 4.55 (br s, 1H), 4.10-4.20 (m, 1H), 3.59-3.76 (m, 2H), 3.23-3.52 (m, 8H), 2.52 (s, 3H), 2.18 (s, 1H), 2.03-2.14 (m, 1H), 1.49 (br d, J=6.2 Hz, 3H), 1.10 (br s, 9H). m/z (ESI, +ve ion): 824 $(M+H)^+$.

(2S,4R)-1-((S)-2-(3-(4-(3-Amino-6-(2-hydroxyphenyl)pyridazin-4-yl)piperazin-1-yl)benzamido)-3,3-dimethylbutanoyl)-4-hydroxy-N—((S)-1-(4-(4-methylthiazol-5-yl)phenyl)ethyl)pyrrolidine-2-carboxamide (Example 7)

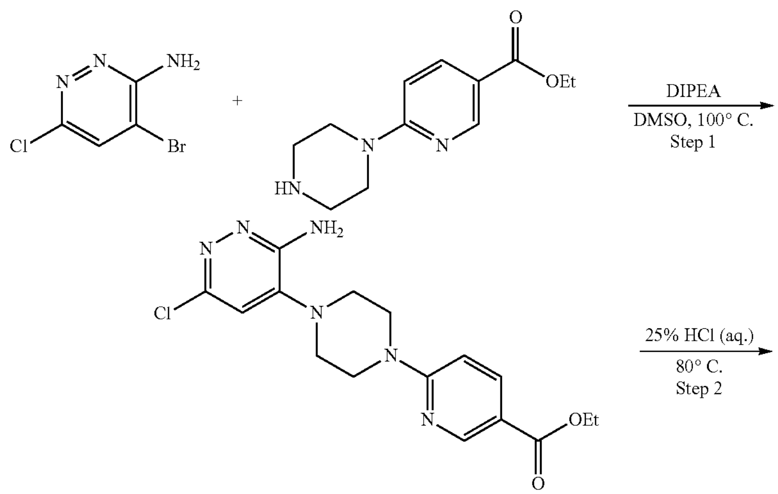

-continued

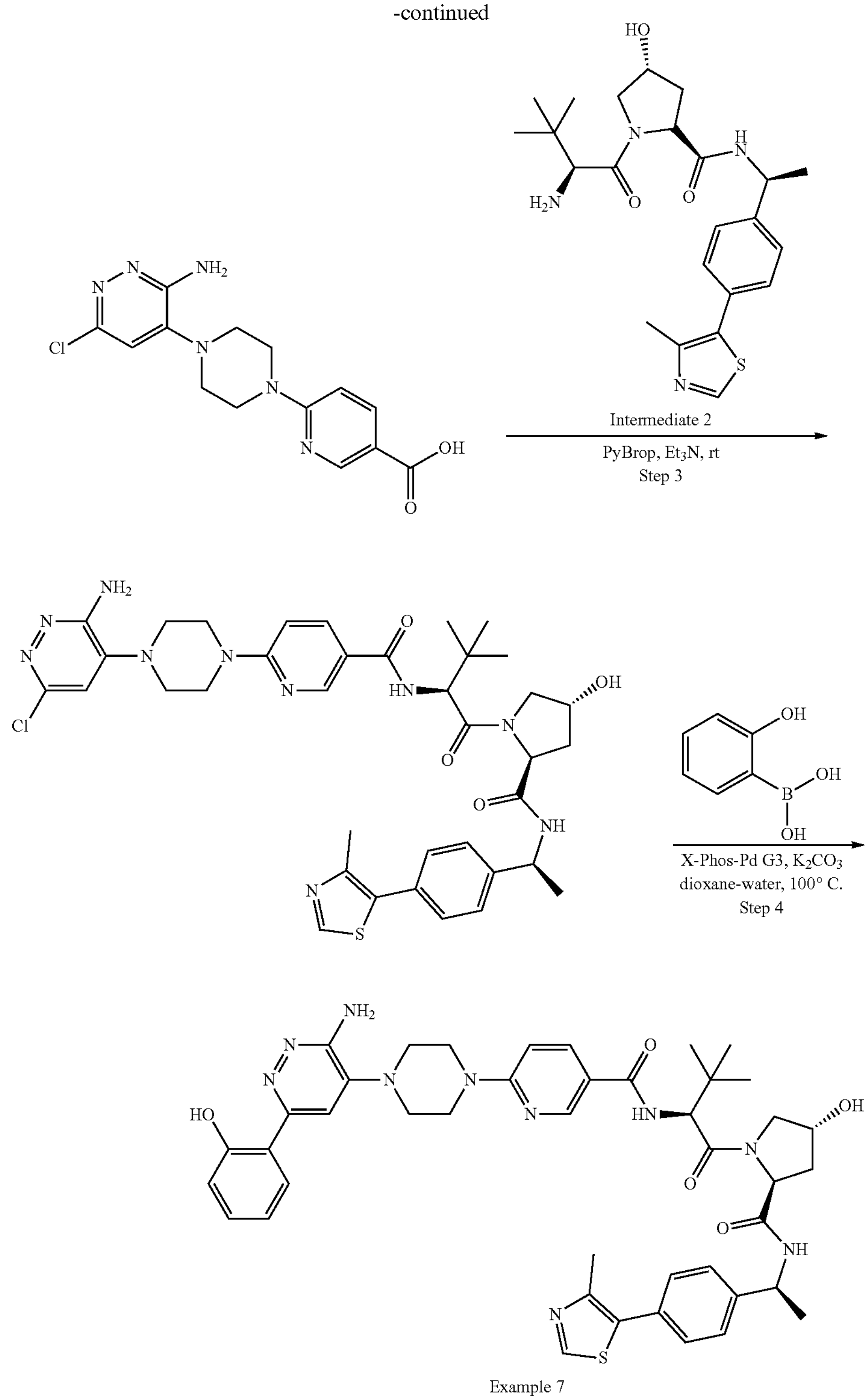

Example 7

Step 1: Ethyl 6-(4-(3-amino-6-chloropyridazin-4-yl)piperazin-1-yl)nicotinate. To a solution of 1-(5-ethoxycarbonyl-pyridin-2-yl)piperazine (2.19 g, 9.30 mmol) in DMSO (3 mL) was added 3-amino-4-bromo-6-chloropyridazine (2.33 g, 11.2 mmol), followed by DIPEA (4.87 mL, 27.9 mmol) dropwise. The reaction mixture was stirred at 100° C. for 18 h. The reaction mixture was diluted with water and the resulting precipitate was collected by filtration, washed with water and EtOAc and dried to afford ethyl 6-(4-(3-amino-6-chloropyridazin-4-yl)piperazin-1-yl)nicotinate (2.23 g, 6.14 mmol, 66% yield) as tan solid. $^1H$ NMR (400 MHz, DMSO-$d_6$) δ ppm 8.67 (d, J=2.28 Hz, 1H), 7.97 (dd, J=9.12, 2.28 Hz, 1H), 6.95 (d, J=8.17 Hz, 1H), 6.94 (s, 1H), 6.27 (s, 2H), 4.26 (q, J=7.05 Hz, 2H), 3.80-3.90 (m, 4H), 3.03-3.14 (m, 4H), 1.29 (t, J=7.15 Hz, 3H). m/z (ESI, +ve ion): 363.02 $(M+H)^+$.

Step 2: 6-(4-(3-Amino-6-chloropyridazin-4-yl)piperazin-1-yl)nicotinic acid. The suspension of ethyl 6-(4-(3-amino-6-chloropyridazin-4-yl)piperazin-1-yl)nicotinate (1.23 g, 3.38 mmol) in 25% aqueous hydrochloric acid (4.1 mL, 33.8 mmol) was stirred at 80° C. for 18 h. The reaction mixture was neutralized with 5N aqueous NaOH to pH 6-7. The resulting precipitate was collected by filtration, dried in a vacuum oven to give 6-(4-(3-amino-6-chloropyridazin-4-yl)piperazin-1-yl)nicotinic acid (0.62 g, 1.85 mmol, 55% yield) as tan solid. The filtrate was extracted with EtOAc (product stayed in aqueous layer). The aqueous solution was lyophilized to provide another 0.54 g of product as a light-tan solid (combined yield 100%). $^1$H NMR (400 MHz, DMSO-$d_6$) δ ppm 8.62 (d, J=1.87 Hz, 1H), 7.97 (dd, J=8.71, 2.07 Hz, 1H), 6.95 (s, 1H), 6.78 (d, J=8.91 Hz, 1H), 6.23 (s, 2H), 3.66-3.77 (m, 4H), 3.01-3.14 (m, 4H). m/z (ESI, +ve ion): 335.0 $(M+H)^+$.

Step 3: 6-(4-(3-Amino-6-chloropyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)nicotinamide. A mixture of 6-(4-(3-amino-6-chloropyridazin-4-yl)piperazin-1-yl)nicotinic acid (0.10 g, 0.30 mmol), TEA (0.13 mL, 0.90 mmol), (2S,4R)-1-(0)-2-amino-3,3-dimethylbutanoyl)-4-hydroxy-N-((5)-1-(4-(4-methylthiazol-5-yl)phenyl)ethyl)pyrrolidine-2-carboxamide (Intermediate 2, 0.33 g, 0.75 mmol), and bromotri(1-pyrrolidinyl)phosphonium hexafluorophosphate (0.15 g, 0.33 mmol) in DCM (1 mL) was stirred at r.t. for 1 h. The reaction mixture concentrated under reduced pressure (rotary evaporator) and purified by column chromatography on silica gel eluting with 0-100% EtOAc/EtOH (3:1) in heptane affording 2-(4-(3-amino-6-(4-(3-amino-6-chloropyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl) nicotinamide (67 mg, 0.088 mmol, 30% yield) as off-white solid. m/z (ESI, +ve ion): 761.1 $(M+H)^+$.

Step 4: 6-(4-(3-Amino-6-(2-hydroxyphenyl)pyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)nicotinamide (Example 7). The mixture of 6-(4-(3-amino-6-chloropyridazin-4-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl) nicotinamide (71 mg, 0.093 mmol), 2-hydroxybenzeneboronic acid (26 mg, 0.19 mmol), X-Phos Pd G3 (7.9 mg, 9.3 μmol) and anhydrous potassium carbonate (32 mg, 0.23 mmol) were flushed with nitrogen and treated with 1,4-dioxane (350 μL) and water (120 μL). The reaction mixture was then heated at 100° C. for 20 h. Additional boronic acid (12 mg), X-Phos Pd G3 (4 mg) and dioxane (0.3 mL) were added and the reaction mixture stirred at 100° C. for another 6 h. The reaction mixture was partitioned between EtOAc and brine and the aqueous layer was back-extracted with EtOAc (3×) and the combined organics was dried ($Na_2SO_4$) and concentrated under reduced pressure (rotary evaporator). The crude material was purified by column chromatography on silica gel eluting with a gradient of 0-80% EtOAc/EtOH (3:1) in heptane, to provide 6-(4-(3-amino-6-(2-hydroxyphenyl)pyridazin-4-yl) piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)nicotinamide (Example 7, 17 mg, 0.020 mmol, 22% yield) as tan solid. $^1$H NMR (400 MHz, $CDCl_3$) δ 8.62-8.70 (m, 2H), 7.93 (dd, J=2.49, 8.91 Hz, 1H), 7.59 (dd, J=1.24, 8.09 Hz, 1H), 7.34-7.46 (m, 6H), 7.28-7.33 (m, 1H), 7.06 (dd, J=0.93, 8.19 Hz, 1H), 6.88-6.96 (m, 1H), 6.67 (dd, J=8.81, 18.14 Hz, 2H), 5.10 (t, J=7.15 Hz, 1H), 4.87 (s, 2H), 4.70-4.81 (m, 2H), 4.56 (br s, 1H), 4.22 (br d, J=11.40 Hz, 1H), 3.80-3.92 (m, 4H), 3.65 (dd, J=3.63, 11.51 Hz, 1H), 3.21-3.30 (m, 4H), 2.55-2.64 (m, 1H), 2.53 (s, 3H), 2.09 (br dd, J=7.98, 13.99 Hz, 1H), 1.49 (d, J=6.84 Hz, 3H), 1.13 (s, 9H). m/z (ESI, +ve ion): 819.3 $(M+H)^+$.

(2S,4R)-1-((S)-2-(2-(2-(4-(3-Amino-6-(2-hydroxyphenyl)pyridazin-4-yl)piperazin-1-yl)pyridin-4-yl)acetamido)-3,3-dimethylbutanoyl)-4-hydroxy-N—((S)-1-(4-(4-methylthiazol-5-yl)phenyl)ethyl)pyrrolidine-2-carboxamide (Example 8)

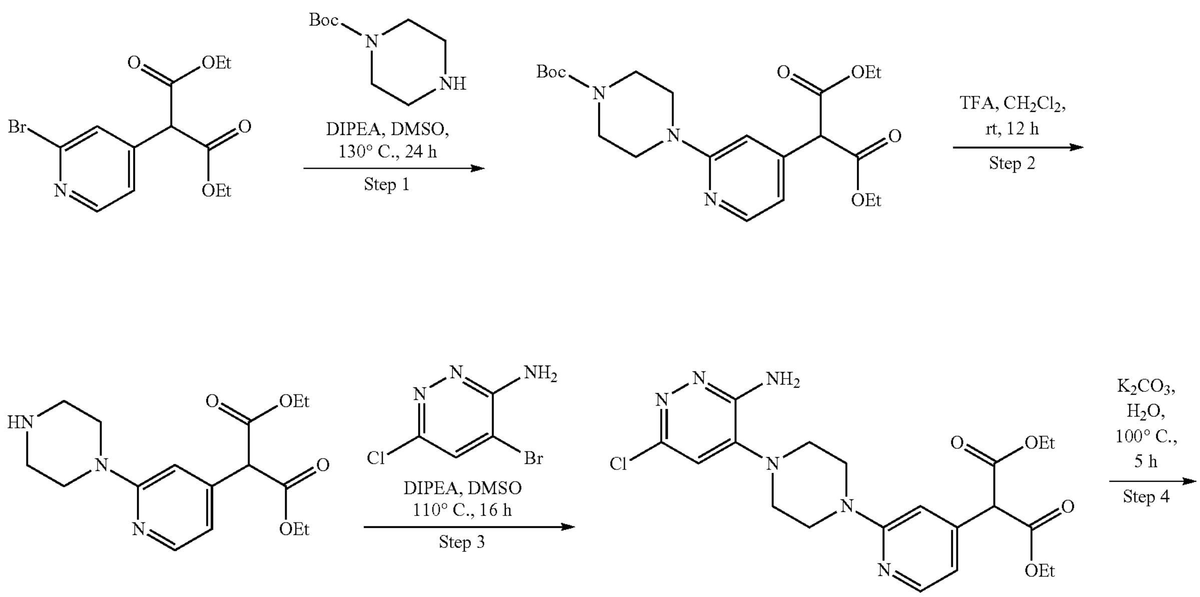

-continued

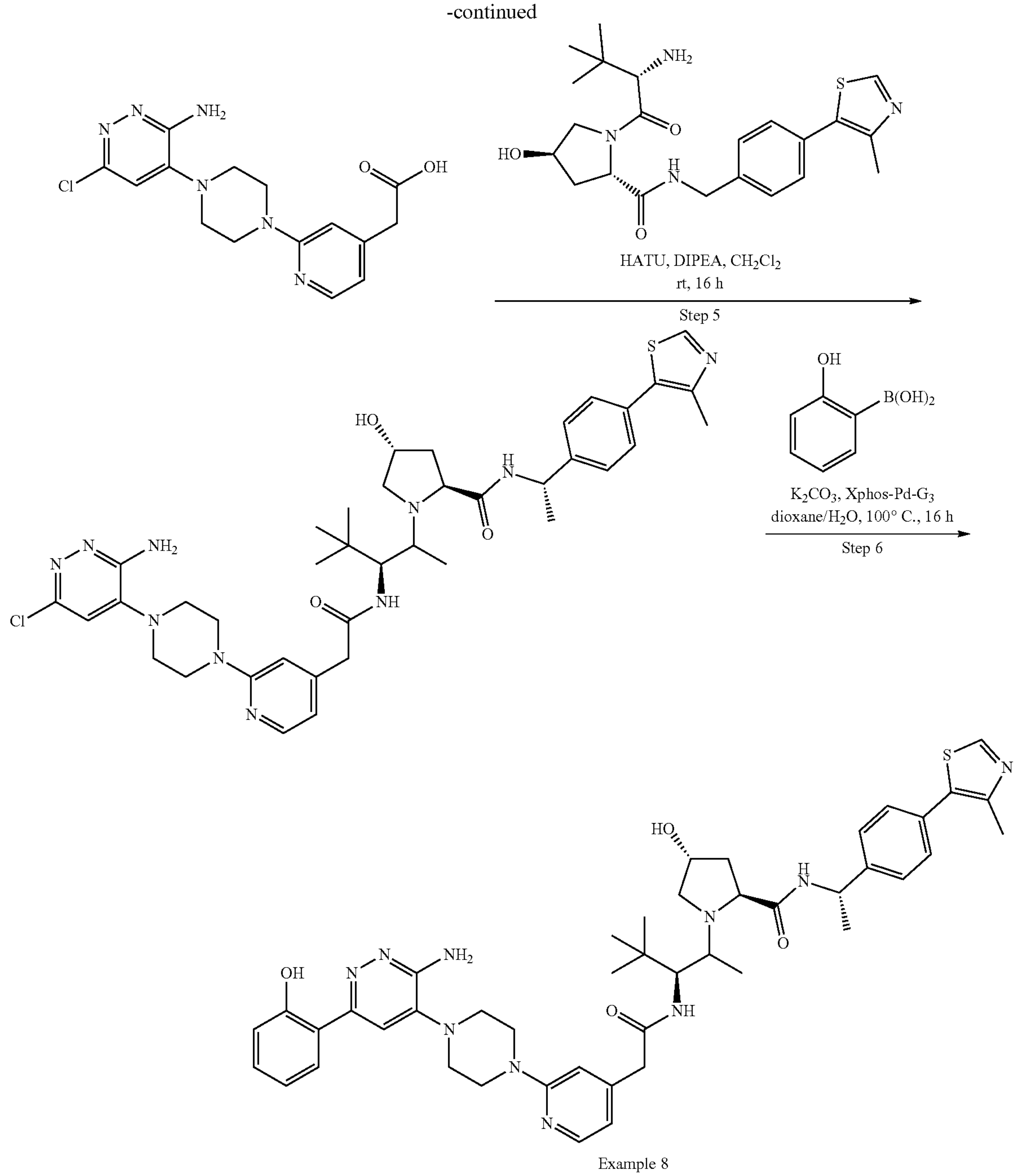

Example 8

Step 1: Diethyl 2-(2-(4-(tert-butoxycarbonyl)piperazin-1-yl)pyridin-4-yl)malonate. A solution of diethyl 2-(2-bromopyridin-4-yl)malonate (1.00 g, 3.16 mmol), tert-butyl piperazine-1-carboxylate (1.18 g, 6.33 mmol, Chempure) and DIPEA (1.66 mL, 9.49 mmol) in DMSO (10 mL) was stirred at 130° C. for 24 h. The reaction mixture was diluted with ice-cold water and extracted with ethyl acetate. The combined organic extracts were washed with brine, dried over $Na_2SO_4$, concentrated under reduced pressure (rotary evaporator) and purified by column chromatography on silica gel using 0-30% EtOAc in hexane, to afford diethyl 2-(2-(4-(tert-butoxycarbonyl) piperazin-1-yl)pyridin-4-yl) malonate (0.33 g, 0.78 mmol, 25% yield) as light-yellow oil. $^1H$ NMR (400 MHz, DMSO-$d_6$): δ ppm 8.08 (d, J=5.1 Hz, 1H), 6.78 (s, 1H), 6.61 (d, J=5.2 Hz, 1H), 5.22 (s, 1H), 4.08-4.14 (m, 4H), 3.83-3.78 (m, 4H), 3.44-3.38 (m, 4H), 1.35-1.44 (s, 9H), 1.17 (t, J=7.1 Hz, 6H). m/z (ESI): 422.2 $(M+H)^+$.

Step 2: Diethyl 2-(2-(piperazin-1-yl)pyridin-4-yl)malonate. To a solution of diethyl 2-(2-(4-(tert-butoxycarbonyl) piperazin-1-yl)pyridin-4-yl)malonate (0.33 g, 0.78 mmol) in DCM (10 mL) was added TFA (0.5 mL, 6.49 mmol) at 0° C. and the reaction mixture was stirred at r.t. for 12 h. The solvent was evaporated to afford diethyl 2-(2-(piperazin-1-yl)pyridin-4-yl)malonate (0.25 g, 0.78 mmol, 99% yield) as light yellow gummy oil. m/z (ESI): 322.1 $(M+H)^+$.

Step 3: Diethyl 2-(2-(4-(3-amino-6-chloropyridazin-4-yl) piperazin-1-yl)pyridin-4-yl)malonate. A solution of diethyl 2-(2-(piperazin-1-yl)pyridin-4-yl)malonate (0.25 g, 0.78 mmol), 4-bromo-6-chloropyridazin-3-amine (0.16 g, 0.78 mmol) and DIPEA (0.41 mL, 2.33 mmol) in DMSO (5 mL) was stirred at 110° C. for 16 h. The reaction mixture was diluted with ice-cold water and extracted with ethyl acetate. The organic extract was dried over anhydrous $Na_2SO_4$, concentrated under reduced pressure (rotary evaporator) and purified by column chromatography on silica gel, eluting with 0-10% MeOH in DCM, to provide diethyl 2-(2-(4-(3-amino-6-chloropyridazin-4-yl)piperazin-1-yl)pyridin-4-yl) malonate (0.15 g, 0.33 mmol, 43% yield) as light brown gummy oil, $^1$H NMR (300 MHz, DMSO-$d_6$): δ ppm 8.10 (dd, J=17.7, 5.1 Hz, 1H), 6.95 (s, 1H), 6.80 (s, 1H), 6.56-6.72 (m, 1H), 6.24 (s, 2H), 3.97-4.24 (m, 3H), 3.59-3.72 (m, 6H), 3.09 (t, J=5.1 Hz, 4H), 1.07-1.25 (m, 6H). m/z (ESI): 449.1 $(M+H)^+$.

Step 4: 2-(2-(4-(3-Amino-6-chloropyridazin-4-yl)piperazin-1-yl)pyridin-4-yl)acetic acid. To a solution of diethyl 2-(2-(4-(3-amino-6-chloropyridazin-4-yl)piperazin-1-yl) pyridin-4-yl)malonate (0.15 g, 0.33 mmol) in water (1 mL) was added $K_2CO_3$ (92 mg, 0.67 mmol) and the reaction mixture was stirred at 100° C. for 5 h. The pH was adjusted to pH 7 using 1.5N HCl and the precipitated solids were collected by filtration and dried to afford 2-(2-(4-(3-amino-6-chloropyridazin-4-yl)piperazin-1-yl)pyridin-4-yl)acetic acid (0.080 g, 0.23 mmol, 69% yield) as off-white solid. $^1$H NMR (300 MHz, DMSO-do): δ ppm 12.50 (s, 1H), 8.05 (d, J=5.3 Hz, 1H), 6.98 (s, 1H), 6.88 (s, 1H), 6.65 (d, J=5.3 Hz, 1H), 6.38 (s, 2H), 3.69 (s, 4H), 3.56 (s, 2H), 3.11 (s, 4H). m/z (ESI): 349.1 $(M+H)^+$.

Step 5: (2S,4R)-1-((S)-2-(2-(2-(4-(3-Amino-6-chloropyridazin-4-yl)piperazin-1-yl)pyridin-4-yl)acetamido)-3,3-dimethylbutanoyl)-4-hydroxy-N—((S)-1-(4-(4-methylthiazol-5-yl)phenyl)ethyl)pyrrolidine-2-carboxamide. To a solution of 2-(2-(4-(3-amino-6-chloropyridazin-4-yl)piperazin-1-yl)pyridin-4-yl)acetic acid (0.080 g, 0.23 mmol), DIPEA (0.12 mL, 0.69 mmol) in DCM (5 mL) were added HATU (0.13 g, 0.34 mmol) at 0° C. followed by (2S,4R)-1-((S)-2-amino-3,3-dimethylbutanoyl)-4-hydroxy-N—((R)-1-(4-(4-methylthiazol-5-yl)phenyl)ethyl)pyrrolidine-2-carboxamide hydrochloride (Intermediate 2, 0.13 g, 0.28 mmol). The reaction mixture was stirred for at r.t. for 16 h then the reaction mixture was diluted with water and extracted with DCM. The organic extract was dried over anhydrous $Na_2SO_4$, concentrated under reduced pressure (rotary evaporator) and purified by column chromatography on silica gel eluting with 0-15% MeOH in DCM, to afford (2S,4R)-1-((S)-2-(2-(2-(4-(3-amino-6-chloropyridazin-4-yl) piperazin-1-yl)pyridin-4-yl)acetamido)-3,3-dimethylbutanoyl)-4-hydroxy N—((R)-1-(4-(4-methylthiazol-5-yl)phenyl)ethyl)pyrrolidine-2-carboxamide (0.11 g, 0.14 mmol, 59% yield) as light yellow solid. m/z (ESI): 775.3 $(M+H)^+$.

Step 6: (2S,4R)-1-((S)-2-(2-(2-(4-(3-Amino-6-(2-hydroxyphenyl)pyridazin-4-yl)piperazin-1-yl)pyridin-4-yl)acetamido)-3,3-dimethylbutanoyl)-4-hydroxy-N—((S)-1-(4-(4-methylthiazol-5-yl)phenyl)ethyl)pyrrolidine-2-carboxamide (Example 8). A solution of (2S,4R)-1-((S)-2-(2-(2-(4-(3-amino-6-chloropyridazin-4-yl)piperazin-1-yl) pyridin-4-yl)acetamido)-3,3-dimethylbutanoyl)-4-hydroxy-N—((R)-1-(4-(4-methylthiazol-5-yl)phenyl)ethyl) pyrrolidine-2-carboxamide (0.10 g, 0.13 mmol), (2-hydroxyphenyl)boronic acid (21 mg, 0.16 mmol, Sigma Aldrich) and $K_2CO_3$ (36 mg, 0.26 mmol) in 1,4-dioxane (2 mL):water (0.4 mL) was degassed with nitrogen. Then X-Phos Pd G3 (5 mg, 6.45 μmol, Strem Chemicals) was added to the reaction mixture and it was stirred at 100° C. for 16 h. The reaction mixture was diluted with ice-cold water and extracted with EtOAc and the organic extract was washed with brine, dried over anhydrous $Na_2SO_4$, concentrated under reduced pressure (rotary evaporator) and purified by column chromatography on silica gel using 0-10% MeOH in DCM, to provide (2S,4R)-1-((S)-2-(2-(2-(4-(3-amino-6-(2-hydroxyphenyl)pyridazin-4-yl)piperazin-1-yl) pyridin-4-yl)acetamido)-3,3-dimethylbutanoyl)-4-hydroxy-N—((R)-1-(4-(4-methylthiazol-5-yl)phenyl)ethyl) pyrrolidine-2-carboxamide (Example 8, 44 mg, 0.053 mmol, 41% yield) as off-white solid. $^1$H NMR (400 MHz, DMSO-$d_6$): δ ppm δ 14.22 (s, 1H), 8.98 (s, 1H), 8.38 (d, J=7.8 Hz, 1H), 8.16 (d, J=9.2 Hz, 1H), 8.04 (d, J=5.1 Hz, 1H), 7.99-7.83 (m, 1H), 7.57 (s, 1H), 7.43 (d, J=8.1 Hz, 2H), 7.37 (d, J=8.1 Hz, 2H), 7.30-7.17 (m, 2H), 6.96-6.84 (m, 2H), 6.60 (d, J=5.2 Hz, 1H), 6.40 (s, 2H), 5.10 (d, J=3.5 Hz, 1H), 4.91 (p, J=7.3 Hz, 1H), 4.51 (d, J=9.1 Hz, 1H), 4.43 (t, J=8.1 Hz, 1H), 4.27 (d, J=5.9 Hz, 1H), 3.79-3.66 (m, 4H), 3.64-3.53 (m, 3H), 3.43 (d, J=13.7 Hz, 1H), 3.19 (t, J=4.9 Hz, 3H), 2.45 (s, 3H), 2.02 (dd, J=13.1, 8.1 Hz, 1H), 1.79 (ddd, J=13.1, 8.7, 4.5 Hz, 1H), 1.37 (d, J=7.0 Hz, 3H), 0.93 (d, J=8.9 Hz, 9H). m/z (ESI): 833.3 $(M+H)^+$.

(2S,4R)-1-((S)-2-(3-(2-(4-(3-Amino-6-(2-hydroxyphenyl)pyridazin-4-yl)piperazin-1-yl)pyridin-4-yl) propanamido)-3,3-dimethylbutanoyl)-4-hydroxy-N—((S)-1-(4-(4-methylthiazol-5-yl)phenyl)ethyl) pyrrolidine-2-carboxamide (Example 9)

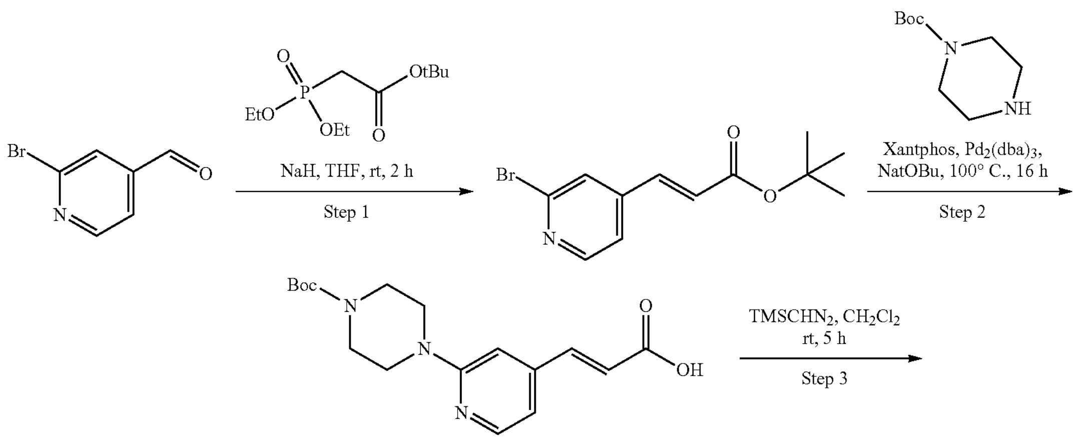

-continued
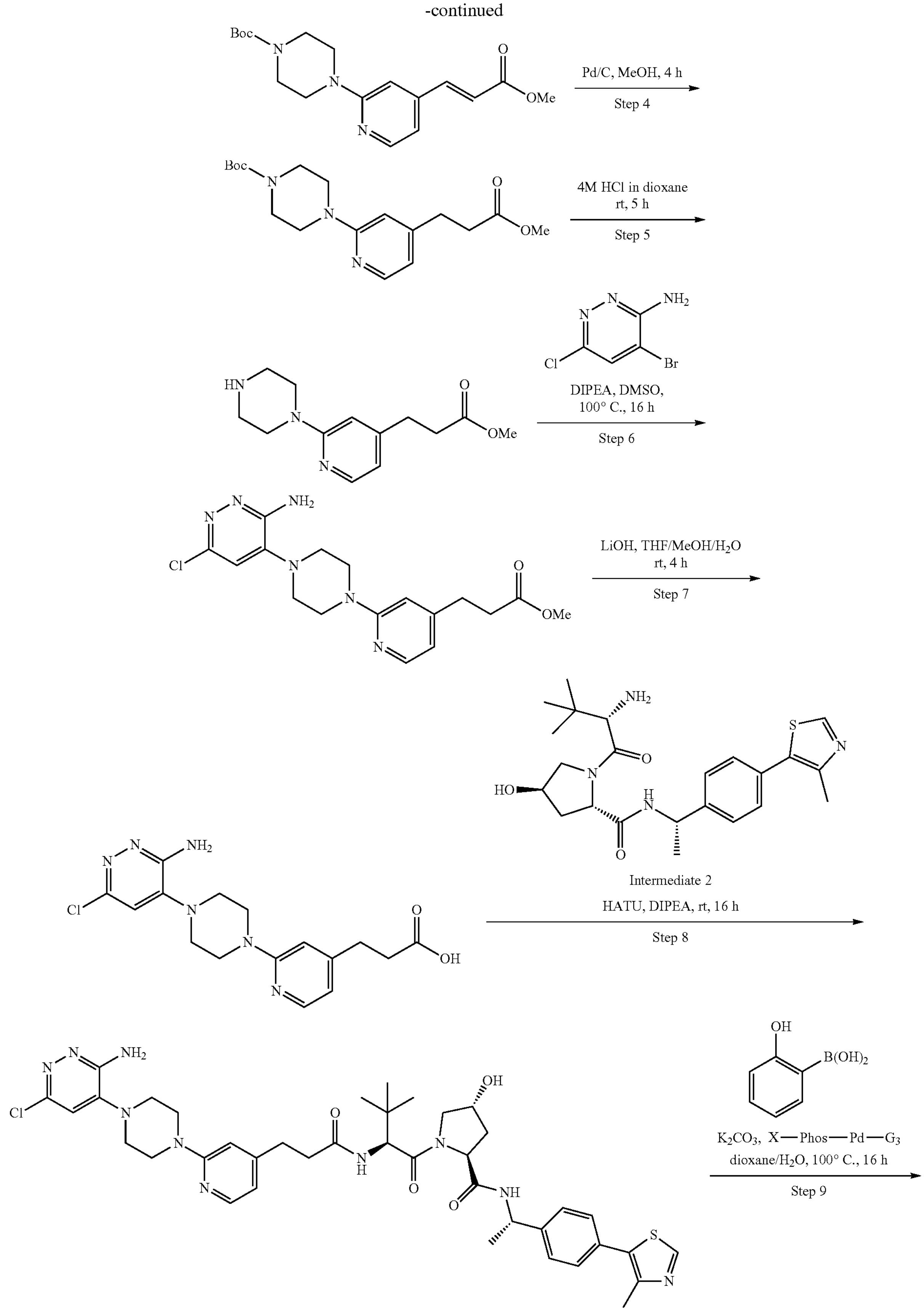

-continued

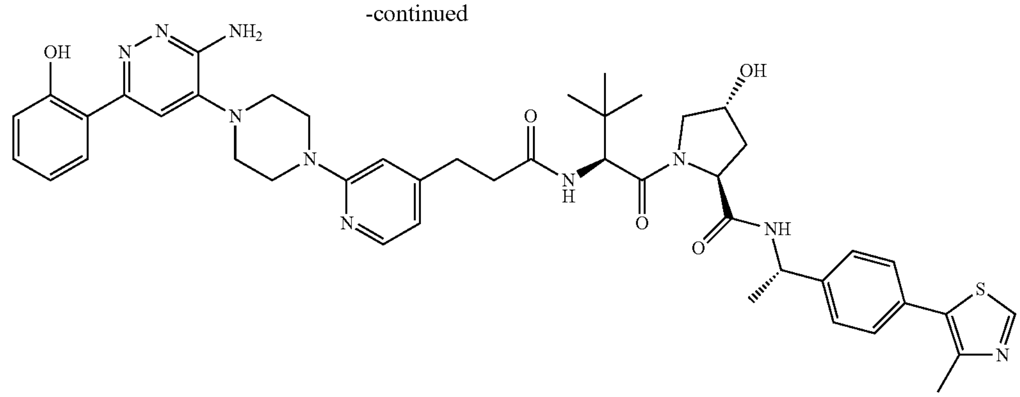

Example 9

Step 1: tert-Butyl (E)-3-(2-bromopyridin-4-yl)acrylate. To a suspension of NaH (0.77 g, 32.0 mmol) in THF (50 mL) was added tert-butyl 2-(diethoxyphosphoryl) acetate (8.14 g, 32.3 mmol, Combi Blocks) at 0° C. After 10 min 2-bromoisonicotinaldehyde (5.00 g, 26.9 mmol, Combi Blocks) was added dropwise and stirred at r.t. for 2 h. The reaction mixture was quenched with ice-cold water and extracted with EtOAc. The organic extract was washed with brine, dried over anhydrous $Na_2SO_4$, concentrated under reduced pressure (rotary evaporator) and purified by column chromatography on silica gel eluting with 10-13% EtOAc in hexane, to provide tert-butyl (E)-3-(2-bromopyridin-4-yl) acrylate (5.80 g, 20.41 mmol, 76% yield) as white solid. $^1$H NMR (400 MHz, DMSO-$d_6$): δ ppm 8.41 (d, J=5.1 Hz, 1H), 7.98-8.02 (m, 1H), 7.76 (dd, J=5.1, 1.5 Hz, 1H), 7.50 (d, J=16.1 Hz, 1H), 6.87 (d, J=16.1 Hz, 1H), 1.49 (s, 9H). m/z (ESI): 284 and 284.0 and 286.0 $(M+H)^+$.

Step 2: (E)-3-(2-(4-(tert-Butoxycarbonyl)piperazin-1-yl) pyridin-4-yl)acrylic acid. A solution of tert-butyl (E)-3-(2-bromopyridin-4-yl)acrylate (1.00 g, 3.52 mmol), tert-butyl piperazine-1-carboxylate (0.79 g, 4.22 mmol, Chempure) and sodium tert-butoxide (0.68 g, 7.04 mmol) in 1,4-dioxane (10 mL) was degassed with nitrogen for 2 min. Then Xantphos (0.20 g, 0.35 mmol, Arbor Chemicals) and $Pd_2(dba)_3$ (0.32 g, 0.35 mmol, Chempure) were added to the reaction mixture and it was stirred at 100° C. for 16 h. The reaction mixture was diluted with water and extracted with EtOAc and the organic extract was dried over anhydrous $Na_2SO_4$, concentrated under reduced pressure (rotary evaporator) to provide (E)-3-(2-(4 (tert-butoxycarbonyl)piperazin-1-yl)pyridin-4-yl)acrylic acid as yellow solid (1.4 g). $^1$H NMR (400 MHz, DMSO-$d_6$): δ ppm 8.10 (d, J=5.1 Hz, 1H), 7.28 (d, J=15.9 Hz, 1H), 7.02 (s, 1H), 6.88 (d, J=5.2 Hz, 1H), 6.69 (d, J=15.9 Hz, 1H), 3.54-3.50 (m, 4H), 3.44-3.40 (m, 4H), 1.32-1.52 (s, 9H). m/z (ESI): 334.2 $(M+H)^+$.

Step 3: tert-Butyl (E)-4-(4-(3-methoxy-3-oxoprop-1-en-1-yl)pyridin-2-yl)piperazine-1-carboxylate. To a solution of (E)-3-(2-(4-(tert-butoxycarbonyl)piperazin-1-yl)pyridin-4-yl)acrylic acid (1.00 g, 3.00 mmol) in DCM (10 mL) was added dropwise TMS-diazomethane in diethyl ether (6.00 mL, 12.00 mmol) at 0° C. and the reaction mixture was stirred at r.t. for 5 h. The reaction mixture was diluted with water and extracted with DCM. The organic extract was dried over anhydrous $Na_2SO_4$, concentrated under reduced pressure (rotary evaporator) and purified by column chromatography on silica gel eluting with 20-25% EtOAc in petroleum ether to afford tert-butyl (E)-4-(4-(3-methoxy-3-oxoprop-1-en-1-yl)pyridin-2-yl)piperazine-1-carboxylate (0.50 g, 1.44 mmol, 48% yield) as orange oil. m/z (ESI): 348.2 $(M+H)^+$.

Step 4: tert-Butyl 4-(4-(3-methoxy-3-oxopropyl)pyridin-2-yl)piperazine-1-carboxylate. A solution of tert-butyl (E)-4-(4-(3-methoxy-3-oxoprop-1-en-1-yl)pyridin-2-yl)piperazine-1-carboxylate (0.60 g, 1.73 mmol) and Pd/C (0.15 g, 0.14 mmol) in MeOH (10 mL) was stirred under an atmosphere of hydrogen (1 atm) for 4 h. The reaction mixture was filtered through a pad of celite and washed with MeOH. The reaction mixture was concentrated under reduced pressure (rotary evaporator) to afford tert-butyl 4-(4-(3-methoxy-3-oxopropyl)pyridin-2-yl)piperazine-1-carboxylate (0.50 g, 83% yield) as light-yellow oil which was taken to the subsequent step without purification. m/z (ESI): 350.2 (M+H).

Step 5: Methyl 3-(2-(piperazin-1-yl)pyridin-4-yl)propanoate. To a solution of tert-butyl 4-(4-(3-methoxy-3-oxopropyl)pyridin-2-yl)piperazine-1-carboxylate (0.53 g, 1.52 mmol) in 1,4-dioxane (2 mL) was added 4 M HCl in dioxane (1 mL) at 0° C. and stirred at r.t. for 2 h. The reaction mixture was concentrated under reduced pressure (rotary evaporator) to afford methyl 3-(2-(piperazin-1-yl)pyridin-4-yl)propanoate hydrochloride (0.43 g, 1.51 mmol, 99% yield) as white solid which was taken to the subsequent step without further purification.

Step 6: Methyl 3-(2-(4-(3-amino-6-chloropyridazin-4-yl) piperazin-1-yl)pyridin-4-yl)propanoate. To a solution of 4-bromo-6-chloropyridazin-3-amine (0.33 g, 1.58 mmol, Combi Blocks) and methyl 3-(2-(piperazin-1-yl)pyridin-4-yl)propanoate hydrochloride (0.45 g, 1.58 mmol) in DMSO (3 mL) was added DIPEA (1.38 mL, 7.92 mmol) and stirred at 100° C. for 16 h. The reaction mixture was diluted with water and extracted with EtOAc and the organic extract was dried over anhydrous $Na_2SO_4$ and concentrated under reduced pressure (rotary evaporator) and purified by column chromatography on silica gel eluting with 10-11% MeOH in DCM, to provide methyl 3-(2-(4-(3-amino-6-chloropyridazin-4-yl)piperazin-1-yl)pyridin-4-yl)propanoate (0.15 g, 0.40 mmol, 27% yield) as light-yellow solid. $^1$H NMR (300 MHz, DMSO-$d_6$): δ ppm 8.02 (d, J=5.1 Hz, 1H), 6.95 (s, 1H), 6.76 (s, 1H), 6.57 (d, J=5.3 Hz, 1H), 6.24 (s, 2H), 3.69-3.65 (m, 4H), 3.60 (s, 3H), 2.78 (t, J=7.5 Hz, 2H), 2.61-2.72 (m, 4H), 2.56 (d, J=8.3 Hz, 2H). m/z (ESI): 377.1 $(M+H)^+$.

Step 7: 3-(2-(4-(3-Amino-6-chloropyridazin-4-yl)piperazin-1-yl)pyridin-4-yl)propanoic acid. To a solution of methyl 3-(2-(4-(3-amino-6-chloropyridazin-4-yl)piperazin-1-yl)pyridin-4-yl)propanoate (0.15 g, 0.40 mmol) in MeOH (1 mL), THE (1 mL) and water (0.5 mL) was added LiOH monohydrate (50 mg, 1.19 mmol). The reaction mixture was stirred at r.t. for 4 h. The reaction mixture was concentrated under reduced pressure (rotary evaporator), diluted with water and acidified using 1N HCl (to pH 6). The precipitated solid was collected by filtration and dried to provide 3-(2-(4-(3-amino-6-chloropyridazin-4-yl)piperazin-1-yl)pyridin-4-yl)propanoic acid (0.12 g, 0.33 mmol, 83% yield) as white solid. $^1$H NMR (300 MHz, DMSO-$d_6$): δ ppm 12.19 (s, 1H), 8.02 (d, J=5.2 Hz, 1H), 6.96 (s, 1H), 6.80 (s, 1H), 6.60 (d, J=5.2 Hz, 1H), 6.28 (s, 2H), 3.70-3.66 (s, 4H), 3.08 (t. J=4.8 Hz, 4H), 2.77 (d, J=7.6 Hz, 2H), 2.58 (d, J=7.4 Hz, 2H). m/z (ESI): 363.1 $(M+H)^+$.

Step 8: (2S,4R)-1-((S)-2-(3-(2-(4-(3-Amino-6-chloropyridazin-4-yl)piperazin-1-yl)pyridin-4-yl)propanamido)-3,3-dimethylbutanoyl)-4-hydroxy-N—((S)-1-(4-(4-methylthiazol-5-yl)phenyl)ethyl)pyrrolidine-2-carboxamide. To a solution of 3-(2-(4-(3-amino-6-chloropyridazin-4-yl)piperazin-1-yl)pyridin-4-yl)propanoic acid (0.12 g, 0.33 mmol) in DCM (3 mL) were added HATU (0.19 g, 0.50 mmol) followed by DIPEA (0.23 mL, 1.32 mmol) at 0° C., after 15 min was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 2, 0.16 g, 0.33 mmol). The reaction mixture was stirred at r.t. for 18 h then the reaction mixture was diluted with water and extracted with DCM. The organic extract was dried over anhydrous $Na_2SO_4$, concentrated under reduced pressure (rotary evaporator) and purified by column chromatography on silica gel eluting with 10-11% MeOH in DCM, to provide (2S,4R)-1-((S)-2-(3-(2-(4-(3-amino-6-chloropyridazin-4-yl)piperazin-1-yl)pyridin-4-yl)propanamido)-3,3-dimethylbutanoyl)-4-hydroxy-N—((S)-1-(4-(4-methylthiazol-5-yl)phenyl)ethyl)pyrrolidine-2-carboxamide (0.20 g, 0.25 mmol, 77% yield) as yellow solid. $^1$H NMR (300 MHz, DMSO-$d_6$): δ ppm 8.99 (s, 1H), 8.38 (d, J=7.8 Hz, 1H), 8.00 (d, J=5.0 Hz, 1H), 7.90 (d, J=9.3 Hz, 1H), 7.44 (d, J=8.4 Hz, 2H), 7.38 (d, J=8.2 Hz, 2H), 6.95 (s, 1H), 6.75 (s, 1H), 6.56 (d, J=5.1 Hz, 1H), 6.24 (s, 2H), 5.12 (d, J=3.4 Hz, 1H), 4.87-4.97 (m, 1H), 4.53 (d, J=9.3 Hz, 1H), 4.43 (t, J=8.1 Hz, 1H), 4.29 (s, 1H), 4.10 (q, J=5.3 Hz, 1H), 3.64 (d, J=17.8 Hz, 6H), 3.17 (d, J=5.2 Hz, 2H), 3.09-3.05 (m, 4H), 2.62 (dd, J=20.7, 13.2 Hz, 1H), 2.46 (s, 3H), 2.01 (d, J=9.3 Hz, 1H), 1.37 (d, J=6.9 Hz, 3H), 0.90 (s, 9H). m/z (ESI): 790.3 $(M+H)^+$.

Step 9: (2S,4R)-1-((S)-2-(3-(2-(4-(3-Amino-6-(2-hydroxyphenyl)pyridazin-4-yl)piperazin-1-yl)pyridin-4-yl)propanamido)-3,3-dimethylbutanoyl)-4-hydroxy-N—((S)-1-(4-(4-methylthiazol-5-yl)phenyl)ethyl)pyrrolidine-2-carboxamide (Example 9). A solution of (2S,4R)-1-((S)-2-(3-(2-(4-(3-amino-6-chloropyridazin-4-yl)piperazin-1-yl)pyridin-4-yl)propanamido)-3,3-dimethylbutanoyl)-4-hydroxy-N—((S)-1-(4-(4-methylthiazol-5-yl)phenyl)ethyl)pyrrolidine-2-carboxamide (0.20 g, 0.25 mmol), (2-hydroxyphenyl)boronic acid (0.042 g, 0.30 mmol, Combi Blocks) and $K_2CO_3$ (0.070 g, 0.51 mmol) in dioxane (5 mL) and $H_2O$ (1 mL) was degassed with nitrogen then treated with X-Phos Pd G-3 (9.8 mg, 0.013 mmol, Aldrich). The reaction mixture was stirred at 100° C. for 18 h, diluted with water and extracted with EtOAc. The organic extract was dried over anhydrous $Na_2SO_4$, concentrated under reduced pressure (rotary evaporator) and purified by column chromatography on silica gel eluting with 10-11% MeOH in DCM to afford (2S,4R)-1-((S)-2-(3-(2-(4-(3-amino-6-(2-hydroxyphenyl)pyridazin-4-yl)piperazin-1-yl)pyridin-4-yl)propanamido)-3,3-dimethylbutanoyl)-4-hydroxy-N—((S)-1-(4-(4-methylthiazol-5-yl)phenyl)ethyl)pyrrolidine-2-carboxamide (Example 9, 0.15 g, 0.18 mmol, 70% yield) as white solid. $^1$H NMR (400 MHz, DMSO-$d_6$): δ ppm 14.22 (s, 1H), 8.98 (s, 1H), 8.37 (d, J=7.8 Hz, 1H), 8.02 (d, J=5.1 Hz, 1H), 7.92 (t, J=9.5 Hz, 2H), 7.55 (d, J=5.2 Hz, 1H), 7.31-7.48 (m, 4H), 7.24 (t, J=7.6 Hz, 1H), 6.81-6.96 (m, 2H), 6.77 (s, 1H), 6.57 (d, J=5.4 Hz, 1H), 6.39 (s, 2H), 5.12 (d, J=3.5 Hz, 1H), 4.90 (d, J=7.3 Hz, 1H), 4.53 (d, J=9.3 Hz, 1H), 4.42 (t, J=8.1 Hz, 1H), 4.28 (s, 1H), 3.71 (d, J=6.0 Hz, 4H), 3.60 (s, 2H), 3.18 (d, J=5.9 Hz, 4H), 2.75 (d, J=7.2 Hz, 1H), 2.63 (d, J=7.5 Hz, 1H), 2.45 (s, 3H), 2.00 (d, J=9.6 Hz, 1H), 1.77 (d, J=13.5 Hz, 1H), 1.36 (d, J=6.9 Hz, 3H), 0.89 (s, 9H). m/z (ESI): 847.3 $(M+H)^+$.

6-(4-(6-Amino-3-(2-hydroxyphenyl)-1,2,4-triazin-5-yl)piperazin-1-yl)-N—((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)picolinamide (Example 10)

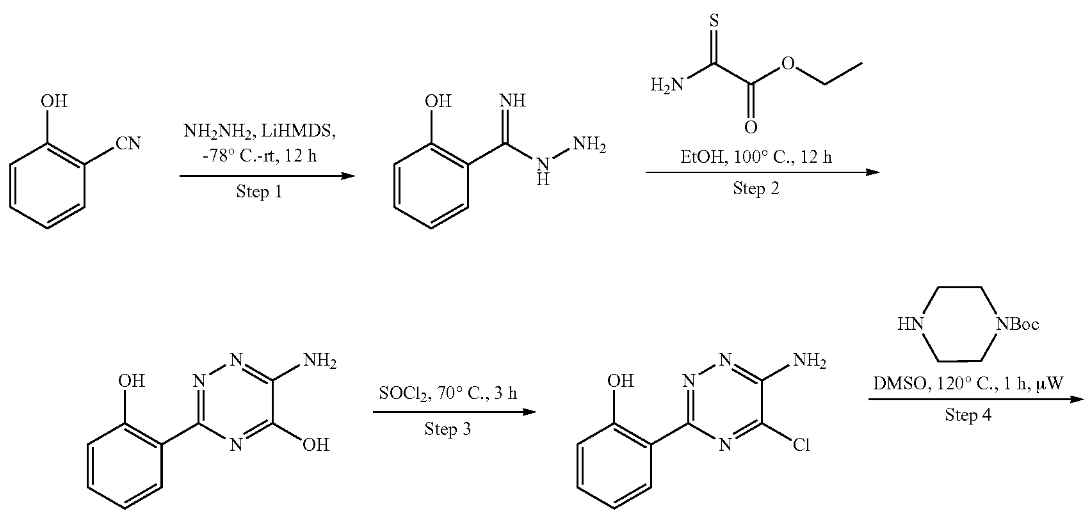

-continued

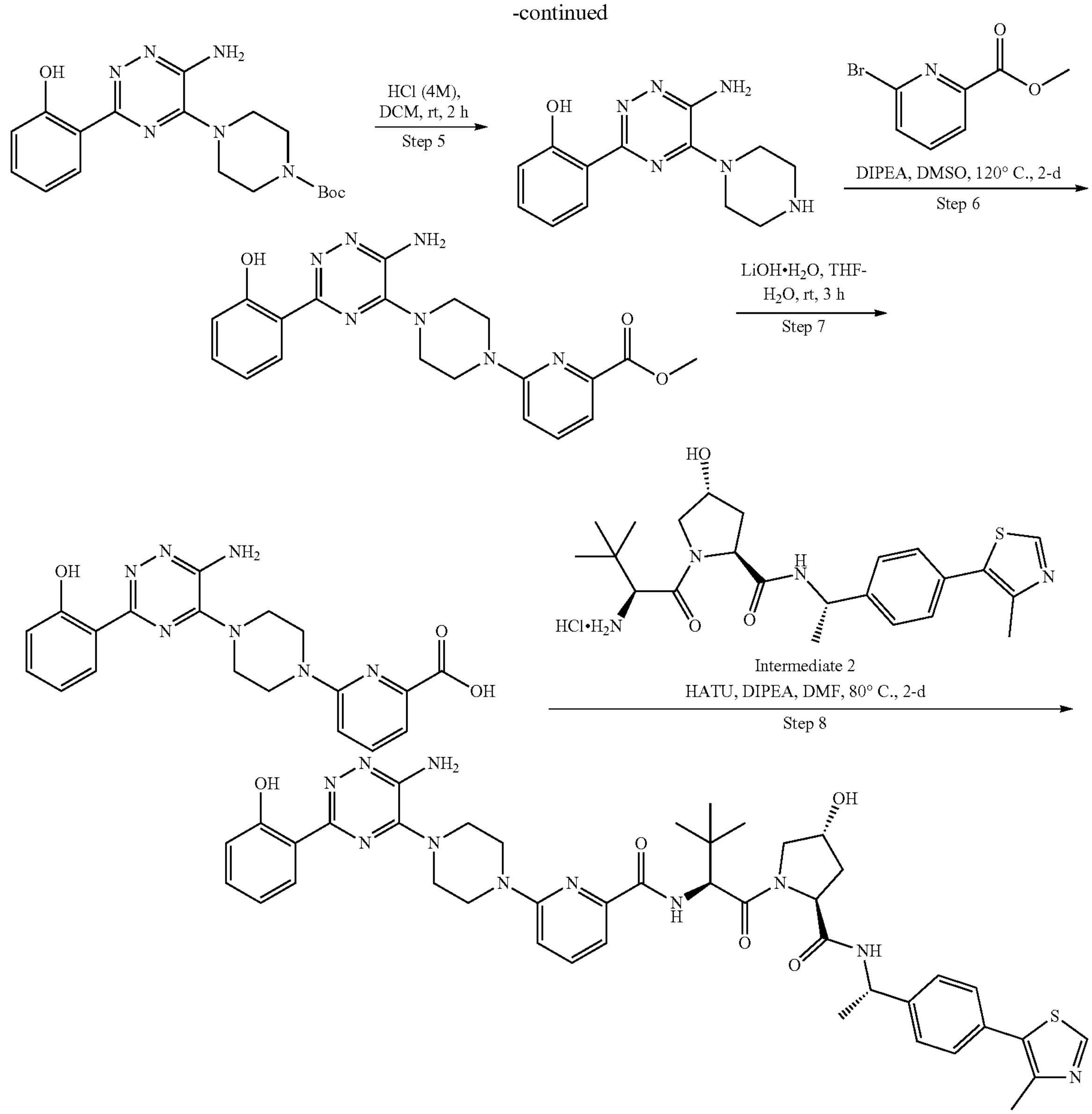

Example 10

Step 1: 2-Hydroxybenzimidohydrazide. To a solution of hydrazine (54.6 mL, 54.6 mmol, Sigma Aldrich) in THF was added 1.0 M LiHMDS in THF (126 mL, 126 mmol, Spectrochem) at −78° C. After 30 min, 2-hydroxybenzonitrile (5.00 g, 42.0 mmol, Combi Blocks) in THF was added to the reaction mixture and stirred at r.t. for 12 h. The reaction mixture was quenched with water and extracted with EtOAc. The combined organic layers were dried over sodium sulfate and concentrated to afford crude 2-hydroxybenzimidohydrazide (5.00 g, 24.81 mmol, 59% yield) as colorless liquid. m/z (ESI): 152.1 $(M+H)^+$.

Step 2: 6-Amino-3-(2-hydroxyphenyl)-1,2,4-triazin-5-ol. A mixture of ethyl 2-amino-2-thioxoacetate (4.29 g, 32.2 mmol, Sigma Aldrich) and 2-hydroxybenzimidohydrazide (5.00 g, 24.81 mmol) in EtOH was stirred at 100° C. for 12 h. The reaction mixture was concentrated, diluted with diethyl ether and stirred at 0° C. The suspension was filtered and washed with cold ethanol to afford 6-amino-3-(2-hydroxyphenyl)-1,2,4-triazin-5-ol (2.00 g, 9.75 mmol, 39% yield) as pale yellow solid. $^1H$ NMR (DMSO-$d_6$, 400 MHz): δ ppm 13.32 (br s, 2H), 7.95 (d, J=8.0 Hz, 1H), 7.38 (t, J=7.8 Hz, 1H), 6.80-7.07 (m, 4H). m/z (ESI): 205.1 $(M+H)^+$.

Step 3: 2-(6-Amino-5-chloro-1,2,4-triazin-3-yl)phenol. A mixture of 6-amino-3-(2-hydroxyphenyl)-1,2,4-triazin-5-ol (2.00 g, 9.79 mmol) and $SOCl_2$ (20 mL, 274 mmol, Spectrochem) was stirred at 70° C. for 3 h. The reaction mixture was concentrated under reduced pressure (rotary evaporator) to afford 2-(6-amino-5-chloro-1,2,4-triazin-3-yl)phenol (2.10 g, 9.43 mmol, 96% yield) as pale yellow solid. $^1H$ NMR (DMSO-$d_6$, 400 MHz): δ ppm 10.65 (br s, 1H), 6.97-7.84 (m, 5H), 6.92 (t, J=7.6 Hz, 1H). m/z (ESI): 223.0 $(M+H)^+$.

Step 4: tert-Butyl 4-(6-amino-3-(2-hydroxyphenyl)-1,2,4-triazin-5-yl)piperazine-1-carboxylate. A mixture of 2-(6-amino-5-chloro-1,2,4-triazin-3-yl)phenol (2.00 g, 8.98 mmol), tert-butyl piperazine-1-carboxylate (3.35 g, 17.97 mmol, Spectrochem), DIPEA (7.85 mL, 44.9 mmol, Spectrochem) in DMSO was stirred at 120° C. for 1 h in microwave. The reaction mixture was diluted with water and extracted with EtOAc. The combined organic layers were dried over sodium sulfate, filtered, concentrated under reduced pressure (rotary evaporator) and purified by column chromatography on silica gel eluting with 40-80% EtOAc in petroleum ether to afford tert-butyl 4-(6-amino-3-(2-hydroxyphenyl)-1,2,4-triazin-5-yl)piperazine-1-carboxylate (0.95 g, 1.35 mmol, 15% yield) as brown solid. m/z (ESI): 373.1 $(M+H)^+$.

Step 5: 2-(6-Amino-5-(piperazin-1-yl)-1,2,4-triazin-3-yl) phenol. A mixture of tert-butyl 4-(6-amino-3-(2-hydroxyphenyl)-1,2,4-triazin-5-yl)piperazine-1-carboxylate (0.95 g, 2.55 mmol) and HCl (4.0 M in dioxane, 638 μL, 2.55 mmol) in DCM was stirred at r.t. for 2 h. The reaction mixture was concentrated under reduced pressure (rotary evaporator) to afford 2-(6-amino-5-(piperazin-1-yl)-1,2,4-triazin-3-yl)phenol hydrochloride (0.87 g, 1.78 mmol, 70% yield) as brown solid. m/z (ESI): 273.1 $(M+H)^+$.

Step 6: Methyl 6-(4-(6-amino-3-(2-hydroxyphenyl)-1,2,4-triazin-5-yl)piperazin-1-yl)picolinate. A mixture of 2-(6-amino-5-(piperazin-1-yl)-1,2,4-triazin-3-yl)phenol hydrochloride (0.85 g, 1.73 mmol), methyl 6-bromopicolinate (0.38 g, 1.73 mmol, Combi Blocks) and DIPEA (0.91 mL, 5.20 mmol) in DMSO was stirred at 120° C. for 48 h. The reaction mixture was cooled to r.t., diluted with cold water and extracted with EtOAc. The combined organic layers were dried over sodium sulfate, filtered, concentrated under reduced pressure (rotary evaporator) and purified by column chromatography on silica gel eluting with 5-15% EtOAc in petroleum ether to afford methyl 6-(4-(6-amino-3-(2-hydroxyphenyl)-1,2,4-triazin-5-yl)piperazin-1-yl)picolinate (0.12 g, 0.22 mmol, 13% yield) as pale yellow solid. m/z (ESI): 408.1 $(M+H)^+$.

Step 7: 6-(4-(6-Amino-3-(2-hydroxyphenyl)-1,2,4-triazin-5-yl)piperazin-1-yl)picolinic acid. A mixture of methyl 6-(4-(6-amino-3-(2-hydroxyphenyl)-1,2,4-triazin-5-yl)piperazin-1-yl)picolinate (0.12 g, 0.21 mmol), and LiOH monohydrate (7.6 mg, 0.32 mmol, Spectrochem) in THF and water was stirred at r.t. for 3 h. The reaction mixture was concentrated, diluted with ice-water and the pH was adjusted to pH 5-6 using 1.5N HCl. The resulting precipitate was collected by filtration and dried to afford 6-(4-(6-amino-3-(2-hydroxyphenyl)-1,2,4-triazin-5-yl)piperazin-1-yl)picolinic acid (80 mg, 0.17 mmol, 79% yield) as pale yellow solid. $^1$H NMR (DMSO-$d_6$, 400 MHz): δ ppm 13.39 (s, 1H), 8.16 (d, J=8.0 Hz, 1H), 7.73 (t, J=8.0 Hz, 1H), 7.23-7.44 (m, 2H), 7.12 (d, J=8.4 Hz, 1H), 6.92 (t, J=8.7 Hz, 2H), 6.61 (s, 2H), 3.79 (br s, 8H). m/z (ESI): 394.1 $(M+H)^+$.

Step 8: 6-(4-(6-Amino-3-(2-hydroxyphenyl)-1,2,4-triazin-5-yl)piperazin-1-yl)-N—((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl) picolinamide (Example 10). To a mixture of 6-(4-(6-amino-3-(2-hydroxyphenyl)-1,2,4-triazin-5-yl)piperazin-1-yl) picolinic acid (60 mg, 0.15 mmol). HATU (87 mg, 0.23 mmol, Spectrochem); and DIPEA (53 μL, 0.31 mmol) in DMF was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 2, 73 mg, 0.15 mmol) and stirred at 80° C. for 48 h. The reaction mixture was diluted with cold water and extracted with EtOAc. The combined organic layer was dried over sodium sulfate, filtered, concentrated under reduced pressure (rotary evaporator) and purified by preparative HPLC to afford 6-(4-(6-amino-3-(2-hydroxyphenyl)-1,2,4-triazin-5-yl)piperazin-1-yl)-N—((S)-1-((2S,4R)-4-hydroxy-2-(((S)-1-(4-(4-methylthiazol-5-yl)phenyl)ethyl) carbamoyl)pyrrolidin-1-yl)-3,3-dimethyl-1-oxobutan-2-yl) picolinamide (Example 10, 20 mg, 0.024 mmol, 16% yield) as pale yellow solid. $^1$H NMR (DMSO-$d_6$, 400 MHz): δ ppm 13.39 (s, 1H), 8.99 (s, 1H), 8.42-8.53 (m, 2H), 8.18 (dd, J=8.1, 1.8 Hz, 1H), 7.79 (t, J=7.9 Hz, 1H), 7.27-7.51 (m, 6H), 7.19 (d, J=8.5 Hz, 1H), 6.89-6.99 (m, 2H), 6.65 (s, 2H), 5.15 (d, J=3.5 Hz, 1H), 4.86-4.96 (m, 1H), 4.69 (d, J=9.8 Hz; 1H), 4.49 (t, J=8.2 Hz, 1H), 4.30 (br s, 1H), 3.72-3.92 (br m, 8H), 3.66 (br s; 2H), 2.46 (s, 3H), 2.05-2.16 (m, 1H), 1.72-1.82 (m, 1H), 1.40 (d, J=7.0 Hz, 3H), 1.02 (s, 9H). m/z (ESI): 820.3 $(M+H)^+$.

N—((S)-1-((2S,4R)-4-Hydroxy-2-(((S)-1-(4-(4-methylthiazol-5-yl)phenyl)ethyl)carbamoyl)pyrrolidin-1-yl)-3,3-dimethyl-1-oxobutan-2-yl)-2-(4-(6-(2-hydroxyphenyl)pyridazin-4-yl)piperazin-1-yl) isonicotinamide (Example 11)

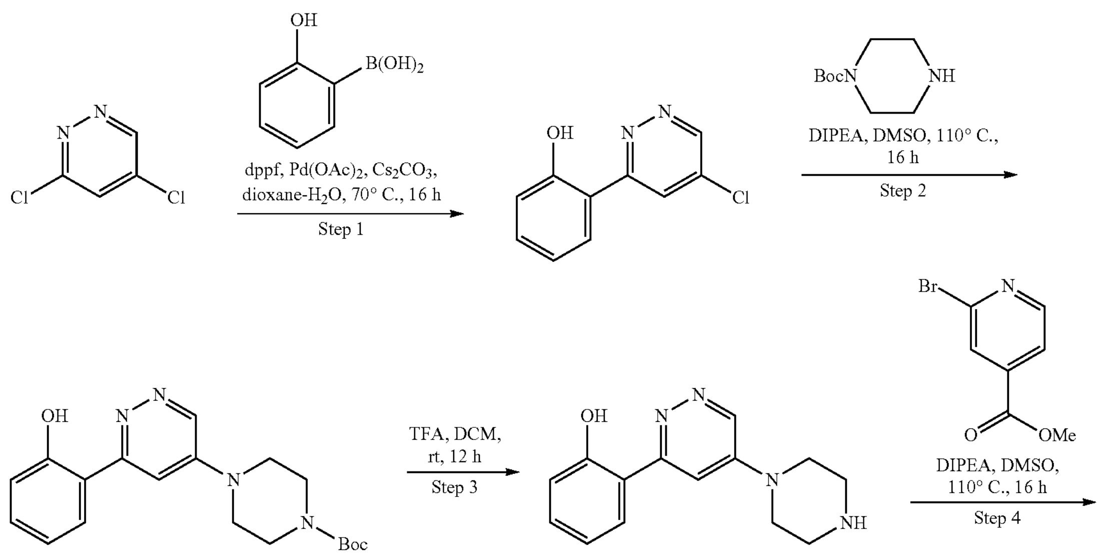

-continued

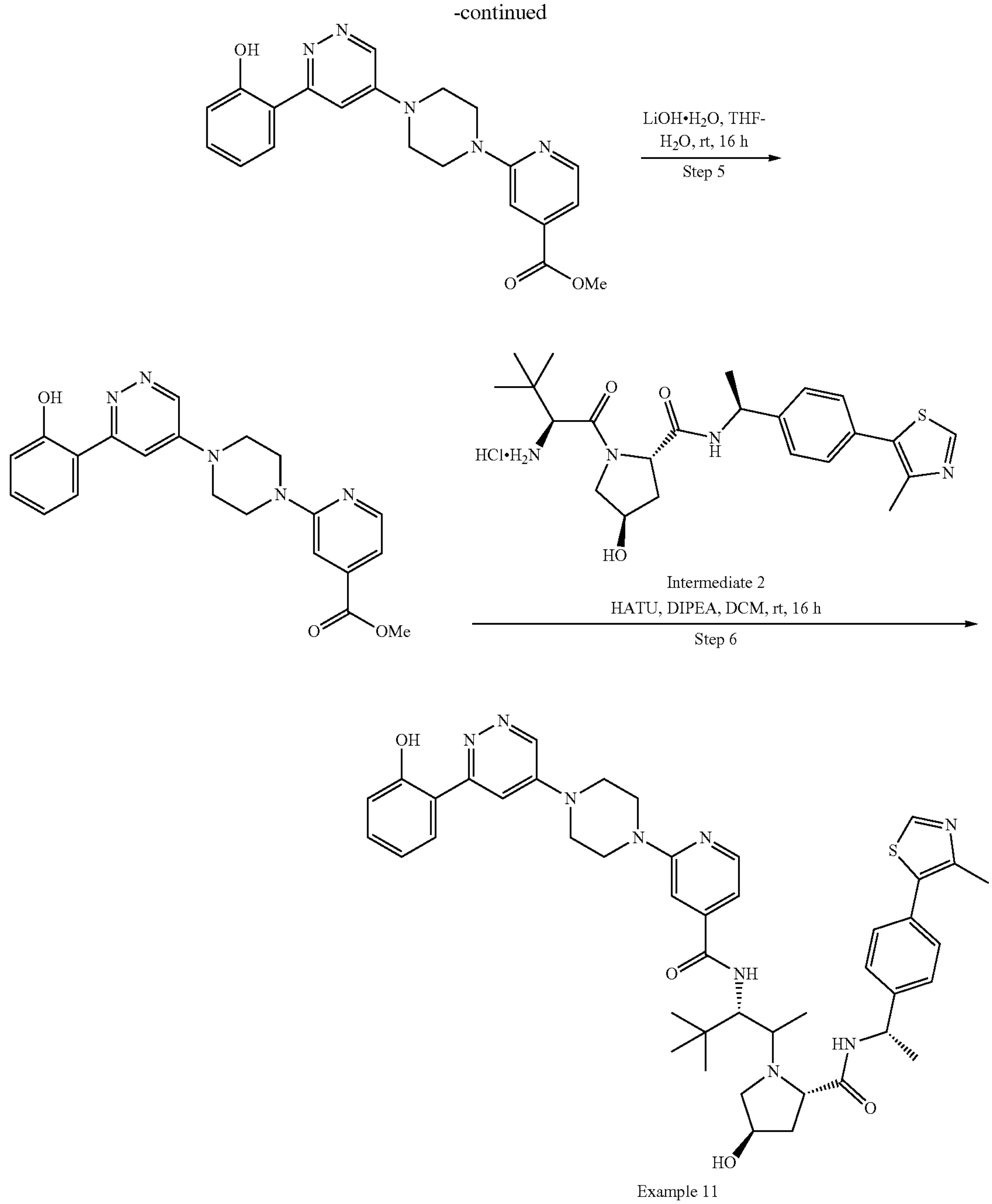

Example 11

Step 1: 2-(5-Chloropyridazin-3-yl)phenol. A mixture of 3,5-dichloropyridazine (2.00 g, 13.43 mmol, Combi Blocks), (2-hydroxyphenyl)boronic acid (1.85 g, 13.43 mmol, Combi Blocks), cesium carbonate (10.94 g, 33.6 mmol, Spectrochem) and bis(diphenylphosphino)ferrocene (0.37 g, 0.67 mmol, Chempure) in 1,4-dioxane and water was treated with palladium(II) acetate (0.15 g, 0.67 mmol, Hindustan Platanium) and stirred at 70° C. for 16 h. The reaction mixture was cooled to r.t., filtered through a celite pad and the filtrate was diluted with water and extracted with EtOAc. The combined organic layers were washed with brine, dried over sodium sulfate, filtered, concentrated under reduced pressure (rotary evaporator) and purified by column chromatography on silica gel using 0-20% EtOAc in petroleum ether, to provide 2-(5-chloropyridazin-3-yl)phenol (0.80 g, 2.09 mmol, 16% yield) as off-white gummy solid. m/z (ESI): 207.1 $(M+H)^+$.

Step 2: tert-Butyl 4-(6-(2-hydroxyphenyl)pyridazin-4-yl) piperazine-1-carboxylate. A mixture of 2-(5-chloropyridazin-3-yl)phenol (0.60 g, 1.57 mmol), DIPEA (1.37 mL, 7.84 mmol) and tert-butyl piperazine-1-carboxylate (1.46 g, 7.84 mmol, Chempure) in DMSO was stirred at 110° C. for 16 h. The reaction mixture was cooled to r.t., diluted with ice-cold water and extracted with ethyl acetate. The combined organic extracts were washed with brine, dried over sodium sulfate, filtered, concentrated under reduced pressure (rotary evaporator) and purified by column chromatography on silica gel eluting with 0-60% EtOAc in petroleum ether, to provide tert-butyl 4-(6-(2-hydroxyphenyl)pyridazin-4-yl)piperazine-1-carboxylate (0.34 g, 0.95 mmol, 61% yield) as light-yellow solid. $^1$H NMR (DMSO-$d_6$, 400 MHz): δ ppm 14.53 (s, 1H), 8.94 (d, J=2.8 Hz, 1H), 8.10 (dd, J=8.4, 1.7 Hz, 1H), 7.56 (d, J=3.0 Hz, 1H), 7.26-7.43 (m, 1H), 6.86-7.00 (m, 2H), 3.60-3.70 (m, 4H), 3.40-3.58 (m, 4H), 1.44 (s, 9H). m/z (ESI): 357.1 $(M+H)^+$.

Step 3: 2-(5-(Piperazin-1-yl)pyridazin-3-yl)phenol. A mixture of tert-butyl 4-(6-(2-hydroxyphenyl)pyridazin-4-yl) piperazine-1-carboxylate (0.34 g, 0.95 mmol) and TFA (1.0 mL, 13 mmol) in DCM was stirred at r.t. for 12 h. The reaction mixture was concentrated and co-evaporated with diethyl ether to give 2-(5-(piperazin-1-yl)pyridazin-3-yl) phenol, 2,2,2-trifluoroacetate salt (0.35 g, 0.95 mmol, 99% yield) as off-white solid. $^1$H NMR (DMSO-$d_6$, 300 MHz): δ ppm 8.97-9.23 (m, 3H), 7.71-7.80 (m, 1H), 7.62 (br s, 1H), 7.44 (t, J=7.7 Hz, 1H), 6.93-7.11 (m, 2H), 3.98 (br s, 4H), 3.31 (br s, 4H). m/z (ESI): 257.2 $(M+H)^+$.

Step 4: Methyl 2-(4-(6-(2-hydroxyphenyl)pyridazin-4-yl) piperazin-1-yl)isonicotinate. A mixture of 2-(5-(piperazin-1-yl)pyridazin-3-yl)phenol, 2,2,2-trifluoroacetate salt (0.35 g, 0.95 mmol), DIPEA (0.66 mL, 3.79 mmol) and methyl 2-bromoisonicotinate (0.31 g, 1.42 mmol, Combi Blocks) in DMSO was stirred at 110° C. for 16 h. The reaction mixture was cooled to r.t., diluted with ice-cold water and extracted with ethyl acetate. The combined organic extracts were washed with brine, dried over sodium sulfate, filtered, concentrated and purified by column chromatography on silica gel using 0-80% EtOAc in petroleum ether, to provide methyl 2-(4-(6-(2-hydroxyphenyl)pyridazin-4-yl)piperazin-1-yl)isonicotinate (0.080 g, 0.20 mmol, 22% yield) as light-yellow solid. $^1$H NMR (DMSO-$d_6$, 300 MHz): δ ppm 14.56 (s, 1H), 8.98 (d, J=2.8 Hz, 1H), 8.33 (d, J=5.1 Hz, 1H), 8.04-8.17 (m, 1H), 7.59 (d, J=2.9 Hz, 1H), 7.30-7.41 (m, 1H), 7.28 (s, 1H), 7.10 (d, J=5.1 Hz, 1H), 6.93 (d, J=7.7 Hz, 2H), 3.88 (s, 3H), 3.78 (s, 8H). m/z (ESI): 392.1 $(M+H)^+$.

Step 5: 2-(4-(6-(2-Hydroxyphenyl)pyridazin-4-yl)piperazin-1-yl)isonicotinic acid.

A mixture of methyl 2-(4-(6-(2-hydroxyphenyl)pyridazin-4-yl)piperazin-1-yl)isonicotinate (0.080 g, 0.20 mmol) and LiOH monohydrate (0.024 g, 1.02 mmol) in THF and water was stirred at r.t. for 16 h. The reaction mixture was concentrated under reduced pressure (rotary evaporator), diluted with ice-water and the pH was adjusted to pH 5-6 using 1.5N HCl. The precipitated solid was filtered and dried to afford 2-(4-(6-(2-hydroxyphenyl)pyridazin-4-yl)piperazin-1-yl)isonicotinic acid (35 mg, 0.093 mmol, 45% yield) as brown solid. $^1$H NMR (DMSO-$d_6$, 400 MHz): δ ppm 9.01 (d, J=3.1 Hz, 1H), 8.31 (d, J=5.1 Hz, 1H), 7.76 (br s, 1H), 7.57 (d, J=3.1 Hz, 1H), 7.44 (t, J=7.8 Hz, 1H), 7.27 (s, 1H), 6.83-7.18 (m, 3H), 3.94 (br s, 4H), 3.73-3.87 (in, 4H). m/z (ESI): 378.1 $(M+H)^+$.

Step 6: N—((S)-1-((2S,4R)-4-Hydroxy-2-(((S)-1-(4-(4-methylthiazol-5-yl)phenyl)ethyl)carbamoyl)pyrrolidin-1-yl)-3,3-dimethyl-1-oxobutan-2-yl)-2-(4-(6-(2-hydroxyphenyl)pyridazin-4-yl)piperazin-1-yl)isonicotinamide (Example 11)

To a mixture of 2-(4-(6-(2-hydroxyphenyl)pyridazin-4-yl) piperazin-1-yl)isonicotinic acid (35 mg, 0.093 mmol), DIPEA (49 μL, 0.28 mmol) and HATU (53 mg, 0.14 mmol, Spectrochem) in DCM was added (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (Intermediate 2, 54 mg, 0.11 mmol) and stirred at r.t. for 16 h. The reaction mixture was diluted with ice-cold water and extracted with DCM. The combined organic extracts were dried over sodium sulfate, filtered, concentrated under reduced pressure (rotary evaporator) and purified by column chromatography on silica gel eluting with 0-10% MeOH in DCM, to provide N—((S)-1-((2S,4R)-4-hydroxy-2-(((5)-1-(4-(4-methylthiazol-5-yl)phenyl)ethyl)carbamoyl)pyrrolidin-1-yl)-3,3-dimethyl-1-oxobutan-2-yl)-2-(4-(6-(2-hydroxyphenyl)pyridazin-4-yl)piperazin-1-yl)isonicotinamide (Example 11, 20 mg, 0.025 mmol, 27% yield) as off-white solid. $^1$H NMR (DMSO-$d_6$, 400 MHz): δ ppm 14.60 (s, 1H), 8.94-9.05 (m, 2H), 8.44 (d, J=7.7 Hz, 1H), 8.35 (d, J=9.1 Hz, 1H), 8.25 (d, J=5.2 Hz, 1H), 8.14 (d, J=8.0 Hz, 1H), 7.62 (s, 1H), 7.31-7.53 (m, 5H), 7.25 (s, 1H), 7.06 (d, J=5.3 Hz, 1H), 6.95 (t, J=7.6 Hz, 2H), 5.16 (d, J=3.5 Hz, 1H), 4.89-5.03 (m, 1H), 4.80 (d, J=9.0 Hz, 1H), 4.46 (t, J=8.2 Hz, 1H), 4.32 (br s, 1H), 3.80 (br s, 8H), 3.68 (br s, 2H), 2.47 (s, 3H), 1.98-2.12 (m, 1H), 1.75-1.87 (m, 1H), 1.39 (d, J=7.0 Hz, 3H), 1.05 (s, 9H). m/z (ESI): 804.3 $(M+H)^+$.

Evaluation of Literature Compounds

Comparative Example 1: (2S,4R)-1-((S)-2-(2-(4-(3-Amino-6-(2-hydroxyphenyl)pyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

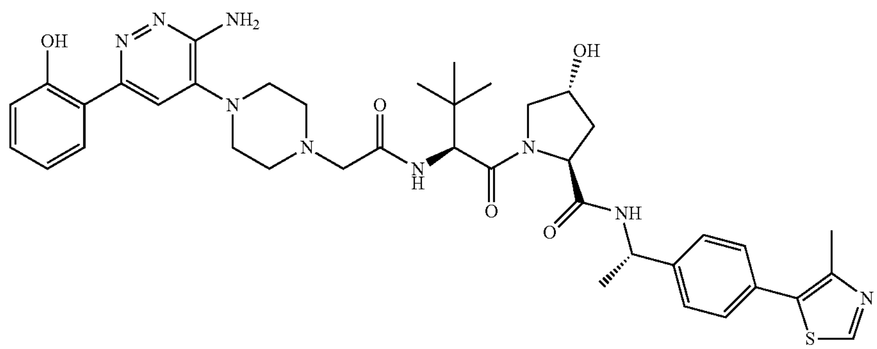 [SMILES: Cc1ncsc1-c1ccc([C@H](C)NC(=O)[C@@H]2C[C@@H](O)CN2C(=O)[C@@H](NC(=O)CN2CCN(c3cc(-c4ccccc4O)nnc3N)CC2)C(C)(C)C)cc1]

The title compound was isolated as off-white solid according to the synthetic procedure provided in WO 2019/207538 (Example 43)

Comparative Example 2: (2S,4R)-1-((S)-2-(2-(4-(3-Amino-6-(3-fluoro-2-hydroxyphenyl)pyridazin-4-yl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide

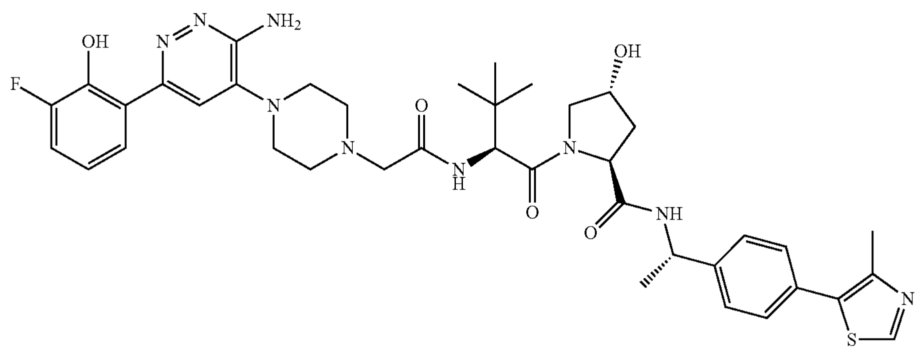 [SMILES: Cc1ncsc1-c1ccc([C@H](C)NC(=O)[C@@H]2C[C@@H](O)CN2C(=O)[C@@H](NC(=O)CN2CCN(c3cc(-c4cccc(F)c4O)nnc3N)CC2)C(C)(C)C)cc1]

The title compound was isolated as light yellow solid according to the synthetic procedure provided in WO 2019/207538 (Example 90).

Biological Activity

Assay Protocols:

SMARCA2 and SMARCA4 MSD Assays in A375 Cells:

Cell Culture:

A375 cells (ATCC® CRL-1619™) were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, cells were seeded in 96-well cell culture plates (Corning 3904) at a density of $2.5\times10^5$ cells/well (90 uL/well) and incubated at 37° C., 5% $CO_2$. A 1:3 compound dose-response titration was diluted in growth media (1:20), added to appropriate wells of a cell culture plate (1:10) and then assay plates were incubated at 37° C., 5% $CO_2$. After 2 h of compound treatment, cells were lysed in MSD lysis buffer (MSD R60TX-2) containing protease (Roche 04693116001) and phosphatase (Roche 04906837001) inhibitors.

Protein Detection:

MSD standard bind plates (MSD L15XA-3) were coated with 40 uL of 2 ug/mL SMARCA2 (Active Motif 39805) or SMARCA4 (Millipore MABE121) capture antibody overnight at 4° C. Plates were then incubated on a plate shaker with 150 uL per well 3% BSA (MSD R93BA-4) for 1 hour, 25 uL per well of cell lysates for 1 hour, 25 ul per well of SMARCA2 (0.25 ug/mL Cell Signaling 119665) or SMARCA4 (1 ug/mL Active Motif 38907) detection antibody for 1 hour then 25 uL per well of 0.5 ug/mL Sulfo-tagged rabbit (SMARCA2, MSD R32AB-5) or Sulfo-tagged rat (SMARCA4, MSD R32AH-5) for 1 hour. Plates were washed with 300 μL per well MSD wash buffer (MSD R61TX-1) between each step. Following the last incubation, plates were washed with MSD wash buffer then 150 uL of MSD read buffer (MSD R92TC-2) was added to each well. Plates were immediately read on a MSD plate reader (MSD Sector Imager 6000) and data was analyzed using a 4-parameter logistic model to calculate $IC_{50}$ values.

TABLE 1

SMARCA2/4 Degradation 2 h in A375 Cells ($IC_{50}$ IP, $IC_{50}$ min value).

| Ex.# | A375 SMARCA2 MSD $IC_{50}$ IP (uM), ($IC_{50}$ min value) | A375 SMARCA4 MSD $IC_{50}$ IP (uM), ($IC_{50}$ min value) |
|---|---|---|
| 1 | 0.11 (0%) | 0.11 (21%) |
| 2 | 0.12 (5%) | 0.20 (40%) |
| 3 | 0.043 (0%) | 0.083 (10%) |
| 4 | 0.022 (1%) | 0.052 (42%) |
| 5 | 0.15 (5%) | 0.23 (23%) |
| 6 | 0.19 (49%) | N/C (86%) |
| 7 | N/C | N/C |
| 8 | N/C | N/C |
| 9 | N/C | N/C |
| 10 | 0.25 (20%) | 0.76 (26%) |
| 11 | 0.35 (39%) | N/C (83%) |
| Comp. Ex. 1 | 0.25 (4%) | 0.84 (16%) |
| Comp. Ex. 2 | 0.42 (5%) | N/C (30%) |

N/C = no curve.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions,
What is claimed is:
1. A compound selected from the group consisting of:
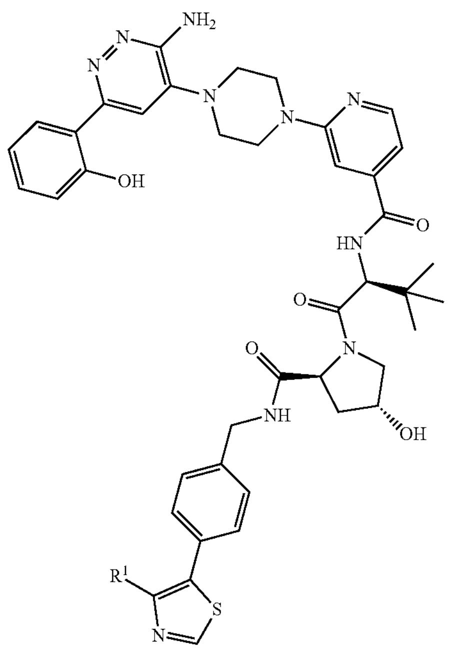
,
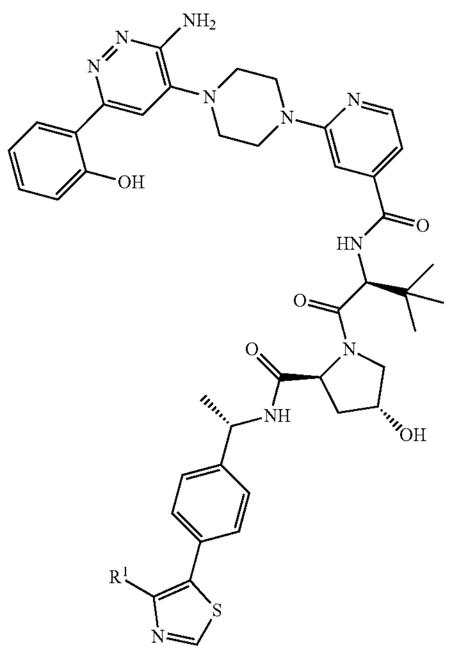
,
-continued
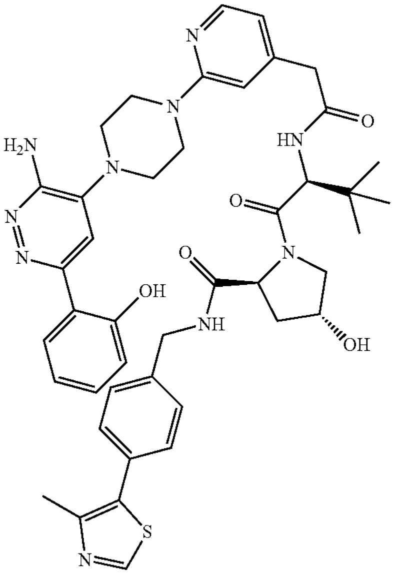
,
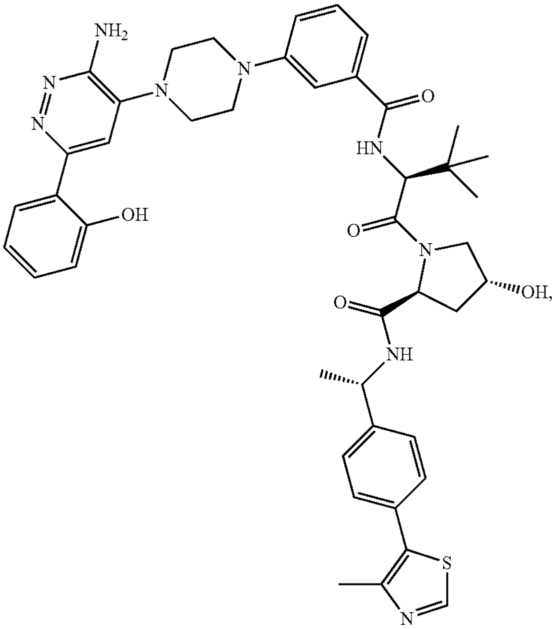
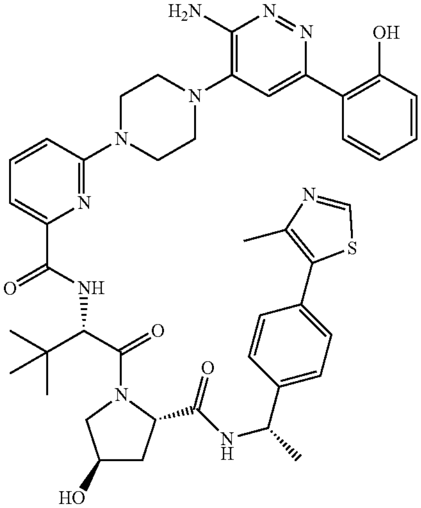
, -continued

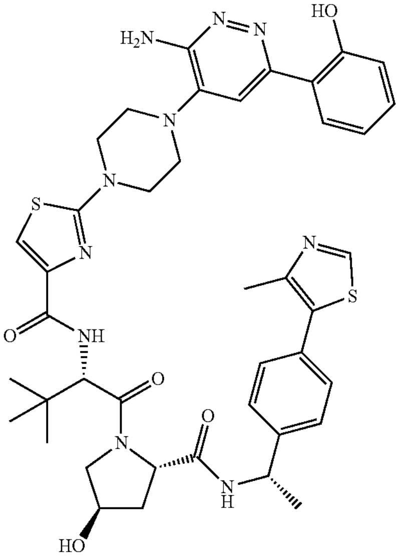

,

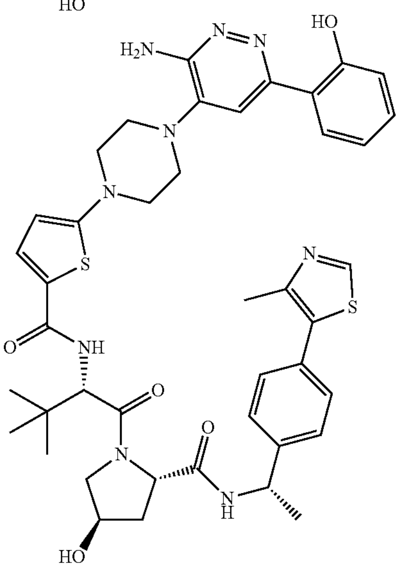

,

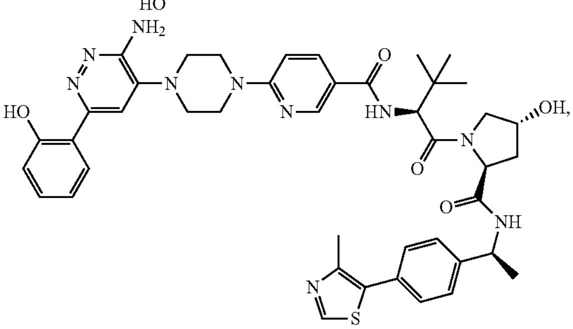

-continued

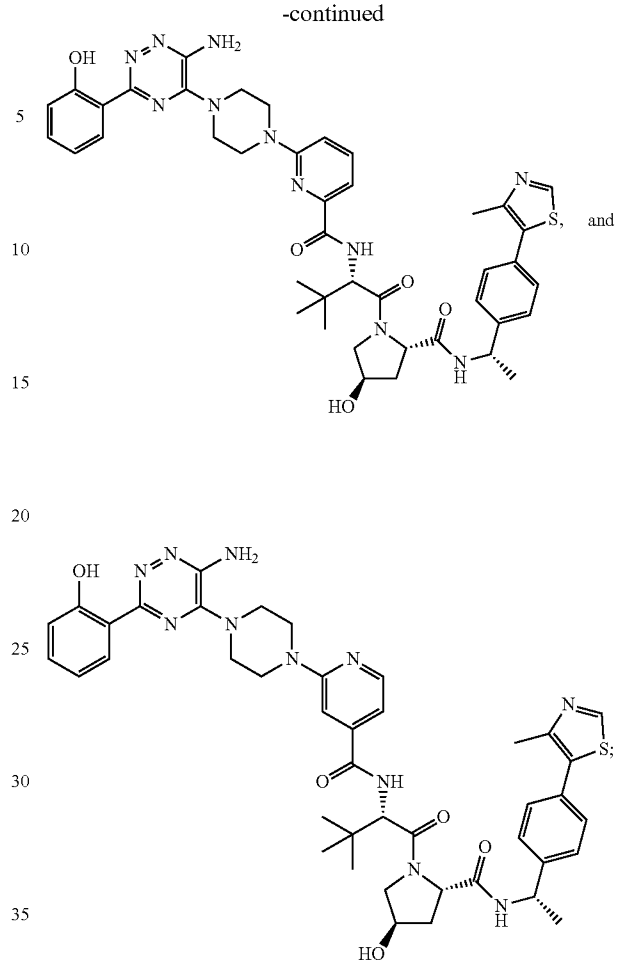

and or a pharmaceutically acceptable salt thereof, wherein $R^1$ is hydrogen, halogen, $C_1$-$C_6$alkyl, hydroxy$C_1$-$C_6$alkyl, or $C_3$-$C_6$cycloalkyl.

2. The compound of claim 1, in a form of a pharmaceutically acceptable salt.

3. A pharmaceutical composition comprising a pharmaceutically acceptable excipient, carrier or adjuvant and at least one compound of claim 1.

4. A method for modulating SMARCA2 and/or SMARCA4 activity in a mammal which method comprises administering to the mammal an amount of at least one compound of claim 1 or a pharmaceutical salt thereof or a pharmaceutical composition thereof to modulate SMARCA2 and/or SMARCA4 activity in the mammal.

* * * * *